(12) United States Patent
Feng et al.

(10) Patent No.: US 10,975,049 B2
(45) Date of Patent: Apr. 13, 2021

(54) NICOTINYL ALCOHOL ETHER DERIVATIVE, PREPARATION METHOD THEREFOR, AND PHARMACEUTICAL COMPOSITION AND USES THEREOF

(71) Applicants: Institute of Materia Medica, Chinese Academy of Medical Sciences, Beijing (CN); Tianjin Chase Sun Pharmaceutical Co., LTD, Tianjin (CN)

(72) Inventors: Zhiqiang Feng, Beijing (CN); Xiaoguang Chen, Beijing (CN); Yang Yang, Beijing (CN); Yi Zheng, Beijing (CN); Fangfang Lai, Beijing (CN); Ming Ji, Beijing (CN); Chuan Zhou, Beijing (CN); Lijing Zhang, Beijing (CN); Ke Wang, Beijing (CN); Nina Xue, Beijing (CN); Ling Li, Beijing (CN)

(73) Assignees: Institute of Materia Medica, Chinese Academy of Medical Sciences, Beijing (CN); Tianjin Chase Sun Pharmaceutical Co., LTD, Tianjin (CN)

( * ) Notice: Subject to any disclaimer, the term of this patent is extended or adjusted under 35 U.S.C. 154(b) by 98 days.

(21) Appl. No.: 16/303,649

(22) PCT Filed: May 23, 2017

(86) PCT No.: PCT/CN2017/085418
§ 371 (c)(1),
(2) Date: Nov. 20, 2018

(87) PCT Pub. No.: WO2017/202274
PCT Pub. Date: Nov. 30, 2017

(65) Prior Publication Data
US 2020/0055819 A1 Feb. 20, 2020
US 2021/0040037 A9 Feb. 11, 2021

(30) Foreign Application Priority Data

May 23, 2016 (CN) .......................... 201610343960.7

(51) Int. Cl.
*C07D 207/16* (2006.01)
*A61P 35/00* (2006.01)
(Continued)

(52) U.S. Cl.
CPC .......... *C07D 295/155* (2013.01); *A61P 35/00* (2018.01); *C07C 45/61* (2013.01); *C07C 211/29* (2013.01); *C07C 227/12* (2013.01); *C07C 229/36* (2013.01); *C07C 231/12* (2013.01); *C07C 233/36* (2013.01); *C07C 235/34* (2013.01); *C07C 255/54* (2013.01); *C07C 269/02* (2013.01); *C07C 271/64* (2013.01);
(Continued)

(58) Field of Classification Search
CPC .............................. C07D 207/16; A61P 35/00
See application file for complete search history.

(56) References Cited

U.S. PATENT DOCUMENTS

| 4,329,518 A | 5/1982 | Plummer et al. |
| 5,872,137 A | 2/1999 | Sakamoto et al. |

(Continued)

FOREIGN PATENT DOCUMENTS

| CN | 1735408 | 2/2006 |
| CN | 103787902 A | 5/2014 |

(Continued)

OTHER PUBLICATIONS

Das, U.N. (Journal of Inflammation Research, 2010:3, pp. 143-170).*
Hartung, H., et al., "What do we know about the mechanism of action of disease-modifying treatments in MS?" J. Neurol., vol. 251 (suppl. 5), p. V/12-V/29 (2004).*
Wang et al., J. Immunol. 2007, 179, pp. 5958-5965, See Introduction.*
International Search Repot and Written Opinion for PCT/CN2017/085420, dated Aug. 9, 2018.

(Continued)

*Primary Examiner* — Alicia L Otton
(74) *Attorney, Agent, or Firm* — Wolf, Greenfield & Sacks, P.C.

(57) ABSTRACT

The present invention discloses a nicotinyl alcohol ether derivative, a preparation method therefor, and a pharmaceutical composition and uses thereof. Specifically, the invention relates to nicotinyl alcohol ether derivatives represented by formula (I), a pharmaceutically-acceptable salt thereof, a stereoisomer thereof, a preparation method therefor, a pharmaceutical composition containing the one or more compounds, and uses of the compounds in treating diseases related to PD-1/PD-L1 signal channels, such as cancers, infectious diseases and autoimmune diseases.

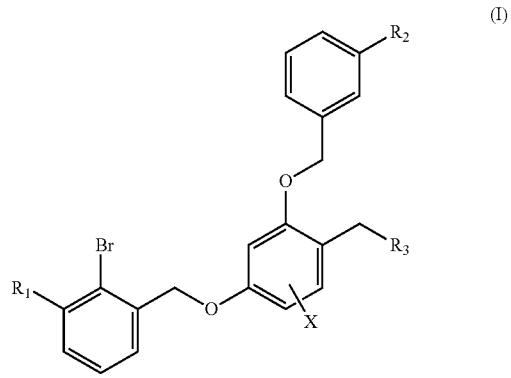

(I)

16 Claims, 8 Drawing Sheets

(51) Int. Cl.

| | | |
|---|---|---|
| C07D 295/155 | (2006.01) | |
| C07C 233/36 | (2006.01) | |
| C07C 255/54 | (2006.01) | |
| C07D 405/12 | (2006.01) | |
| C07C 311/05 | (2006.01) | |
| C07D 319/18 | (2006.01) | |
| C07C 45/61 | (2006.01) | |
| C07C 231/12 | (2006.01) | |
| C07D 401/14 | (2006.01) | |
| C07C 211/29 | (2006.01) | |
| C07C 229/36 | (2006.01) | |
| C07C 235/34 | (2006.01) | |
| C07D 221/00 | (2006.01) | |
| C07D 265/30 | (2006.01) | |
| C07D 407/12 | (2006.01) | |
| C07C 227/12 | (2006.01) | |
| C07C 269/02 | (2006.01) | |
| C07C 271/64 | (2006.01) | |
| C07D 207/08 | (2006.01) | |
| C07D 309/14 | (2006.01) | |
| C07D 319/16 | (2006.01) | |
| A61K 31/36 | (2006.01) | |
| A61K 31/165 | (2006.01) | |
| A61K 31/277 | (2006.01) | |
| A61K 45/06 | (2006.01) | |

(52) U.S. Cl.
CPC .......... *C07C 311/05* (2013.01); *C07D 207/08* (2013.01); *C07D 207/16* (2013.01); *C07D 221/00* (2013.01); *C07D 265/30* (2013.01); *C07D 309/14* (2013.01); *C07D 319/16* (2013.01); *C07D 319/18* (2013.01); *C07D 401/14* (2013.01); *C07D 405/12* (2013.01); *C07D 407/12* (2013.01); *A61K 31/165* (2013.01); *A61K 31/277* (2013.01); *A61K 31/36* (2013.01); *A61K 45/06* (2013.01)

(56) References Cited

U.S. PATENT DOCUMENTS

| | | | |
|---|---|---|---|
| 2015/0291549 | A1 | 10/2015 | Chupak et al. |
| 2019/0233405 | A1 | 8/2019 | Feng et al. |
| 2019/0241531 | A1 | 8/2019 | Feng et al. |
| 2020/0181115 | A1 | 6/2020 | Feng et al. |

FOREIGN PATENT DOCUMENTS

| | | |
|---|---|---|
| RU | 2144526 C1 | 1/2000 |
| RU | 2238266 C2 | 10/2004 |
| WO | WO 00/53572 A1 | 9/2000 |
| WO | WO 2007/106469 | 9/2007 |
| WO | WO 2013/126428 | 8/2013 |
| WO | WO 2015/034820 A1 | 3/2015 |
| WO | WO 2015/160641 A2 | 10/2015 |

OTHER PUBLICATIONS

International Preliminary Report on Patentability for PCT/CN2017/085420, dated Nov. 27, 2018.
International Search Repot and Written Opinion for PCT/CN2017/085417, dated Aug. 2, 2017.
International Preliminary Report on Patentability for PCT/CN2017/085417, dated Nov. 27, 2018.
International Search Repot and Written Opinion for PCT/CN2017/085418, dated Aug. 9, 2017.
International Preliminary Report on Patentability for PCT/CN2017/085418, dated Nov. 27, 2018.
International Search Repot and Written Opinion for PCT/CN2017/085421, dated Aug. 9, 2017.
International Preliminary Report on Patentability for PCT/CN2017/085421, dated Nov. 27, 2018.
Kusuma et al., Synthesis and Evaluation of Novologues as C-Terminal Hsp90 Inhibitors with Cytoprotective Activity against Sensory Neuron Glucotoxicity. J. Med. Chem., 2012;55(12):5797-5812. DOI: 10.1021/jm300544c.
Sasaki et al., Design, synthesis, and biological activity of potent and orally available G protein-coupled receptor 40 agonists. J Med Chem. Mar. 10, 2011;54(5):1365-78. doi: 10.1021/jm101405t. Epub Feb. 14, 2011.
Smith et al., Suzuki and Heck Coupling Reactions Mediated by Palladium Complexes Bearing trans-Spanning Diphosphines. Journal of Organometallic Chemistry Jan. 2005;690(2):477-481.
Yao et al., An efficient multistep ligand-based virtual screening approach for GPR40 agonists. Molecular Diversity Dec. 5, 2013;18(1):183-193.
Belikov, The relationship between the structure of molecules and their effect on the body in: Pharmaceutical Chemistry. Chapter 2.2. 1993. Moscow: Higher School, Eds. pp. 43-47.
Belikov, Pharmaceutical Chemistry. 2007. MEDpress-inform, Eds. pp. 27-29.
Extended European Search Report for Application No. EP 17802122.6 dated Feb. 12, 2020.
Extended European Search Report for Application No. EP 17802123.4 dated Feb. 12, 2020.
[No Author Listed] Expert Scientific Group on Phase One Clinical Trials Final Report. Nov. 30, 2006. pp. C1, C35-C38.
Gura, Systems for Identifying New Drugs Are Often Faulty. Science. Nov. 7, 1997;278(5340):1041-2. doi: 10.1126/science.278.5340.1041.
Kamb, What's Wrong With Our Cancer Models? Nat Rev Drug Discov. Feb. 2005;4(2):161-5. doi: 10.1038/nrd1635.
Leaf, Health Administrator. 2005; 17(1): 172-183.
McMahon, VEGF receptor signaling in tumor angiogenesis. Oncologist. 2000;5 Suppl 1:3-10. doi:10.1634/theoncologist.5-suppl_1-3.
Neidle, Cancer Drug Design and Discovery. Elsevier. 2008:427-431.
Pinedo et al., Translational Research: the Role of VEGF in Tumor Angiogenesis. Oncologist. 2000;5 Suppl 1:1-2.
Tanc et al., 7-Substituted-sulfocoumarins are isoform-selective, potent carbonic anhydrase II inhibitors. Bioorg Med Chem. 2013;21(15):4502-4510. doi:10.1016/j.bmc.2013.05.032.

\* cited by examiner

NICOTINYL ALCOHOL ETHER DERIVATIVE, PREPARATION METHOD THEREFOR, AND PHARMACEUTICAL COMPOSITION AND USES THEREOF

RELATED APPLICATIONS

This application is a national stage filing under 35 U.S.C. § 371 of international PCT application, PCT/CN2017/085418, filed May 23, 2017, and to Chinese Application number 201610343960.7, filed May 23, 2016.

FIELD OF THE INVENTION

The present invention discloses a nicotinyl alcohol ether derivative, a preparation method therefor, and a pharmaceutical composition and uses thereof. Specifically, the invention relates to nicotinyl alcohol ether derivatives represented by formula (I), a pharmaceutically-acceptable salt thereof, a stereoisomer thereof, a preparation method therefor, a pharmaceutical composition containing the one or more compounds, and uses of the compounds in treating diseases related to PD-1/PD-L1 signal channels, such as cancers, infectious diseases and autoimmune diseases.

BACKGROUND OF THE INVENTION

With the deepening of research on cancer immunology, it has been found that the tumor microenvironment can protect tumor cells from being recognized and killed by the human immune system. The immune escape of tumor cells plays a very important role in tumor occurrence and development. In 2013, Science magazine ranked tumor immunotherapy as the first of the top ten breakthroughs, once again making immunotherapy a "focus" in the field of cancer treatment. Activation or inhibition of immune cells is regulated by positive and negative signals, wherein programmed death 1 (PD-1)/PD-1 ligand (PD-L1) is a negative immune regulatory signal that inhibits the immune activity of tumor-specific CD8+ T cells and mediates immune escape.

Tumor cells evade the immune system by the binding of programmed cell death ligand (PD-L1) produced on its surface to the PD-1 protein of T cells. The tumor microenvironment induces high expression of PD-1 molecules in infiltrating T cells, and tumor cells highly express PD-1 ligands PD-L1 and PD-L2, resulting in continuous activation of the PD-1 pathway in the tumor microenvironment. The inhibited T cells cannot find the tumor so that it cannot signal the immune system to attack and kill the tumor cells. The PD-1 antibody against PD-1 or PD-L1 blocks this pathway by preventing the two proteins from binding and partially restores the function of T cells, enabling them to kill tumor cells.

PD-1/PD-L1-based immunotherapy is a new generation high-profile immunotherapy, aiming to use the body's own immune system to fight tumors. It has the potential to treat multiple types of tumors by blocking the PD-1/PD-L1 signaling pathway to induce apoptosis. Recently, a series of surprising studies have confirmed that PD-1/PD-L1 inhibitory antibodies have strong anti-tumor activity against a variety of tumors, which is particularly eye-catching. On Sep. 4, 2014, Keytruda® (pembrolizumab) from Merck, USA, became the first FDA-approved PD-1 monoclonal antibody for the treatment of advanced or unresectable melanoma patients who were unresponsive for other medications. Currently, MSD is investigating the potential of Keytruda in more than 30 different types of cancer, including various types of blood cancer, lung cancer, breast cancer, bladder cancer, stomach cancer, and head and neck cancer. On Dec. 22, 2014, pharmaceutical giant Bristol-Myers Squibb took the lead in obtaining accelerated approval from the US Food and Drug Administration (FDA). Its anti-cancer immunotherapy drug nivolumab was listed under the trade name Opdivo for the treatment of unresectable or metastatic melanoma patients who have not responded to other drugs and it is the second US-listed PD-1 inhibitor after MSD's Keytruda. On Mar. 4, 2015, FDA approved nivolumab for the treatment of metastatic squamous non-small cell lung cancer that progressed during platinum-based chemotherapy or after chemotherapy. According to a Phase Ib KEYNOTE-028 study of the treatment of solid tumors by Keytruda (pembrolizumab) published by MSD, Keytruda treatment achieved a 28% overall response rate (ORR) in 25 patients with pleural mesothelioma (PM). And 48% of patients have stable disease and the disease control rate has reached 76%. Patients with advanced Hodgkin's lymphoma (HL) who had no treatment response to any of the approved drugs were able to achieve complete remission after receiving treatment with MSD's Keytruda and Bristol-Myers' Opdvio. At the 2015 AACR Annual Meeting, Leisha A. Emens, M D, PhD, associate professor of oncology at the Johns Hopkins Kimmel Cancer Center, reported that Roche's PD-L1 monoclonal antibody MPDL3280A has a long-lasting effect in advanced triple-negative breast cancer.

Tumor immunotherapy is considered a revolution in cancer treatment after tumor targeting therapy. However, the monoclonal antibody therapeutic drug has its own defects: it is easily decomposed by proteases, so it is unstable within the body and cannot be taken orally; it is easy to produce immune cross-reaction; the product quality is not easy to control and the production technology is high; a large amount of preparation and purification is difficult, and the cost is high; it is inconvenient to use and it only can be injected or drip. Therefore, small molecule inhibitors of PD-1/PD-L1 interaction are a better choice for tumor immunotherapy.

CONTENTS OF THE INVENTION

Figure 1:
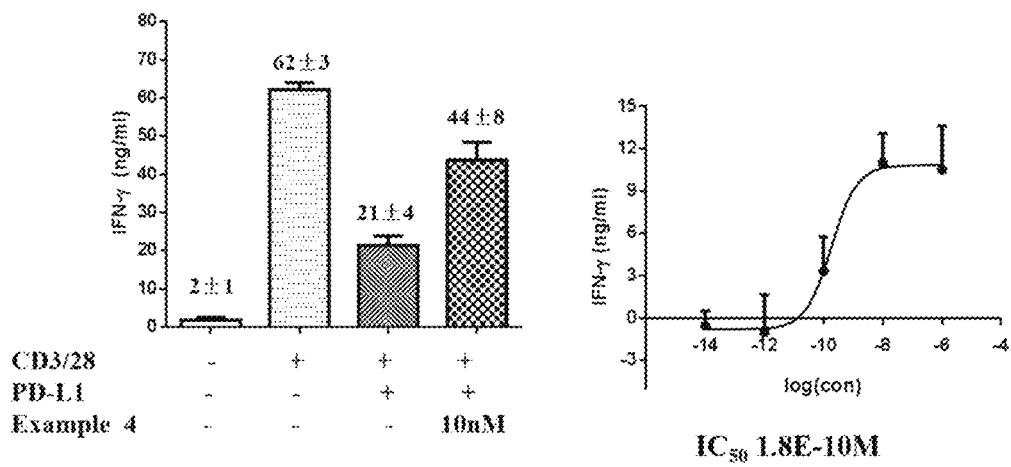
FIG. 1 illustrates the effect of human PD-L1 protein, anti-CD3/ anti-CD28antibody and the Example 4 compound on IFNy.

The technical problem to be solved by the present invention is to provide a nicotinyl alcohol ether derivative with the structural formula (I) which inhibits the interaction of PD-1/PD-L1, and a stereoisomer thereof and a pharmaceutically acceptable salt thereof, and a preparation method therefor and medicament compositions thereof and their use in the prevention or treatment of a disease associated with the PD-1/PD-L1 signaling pathway.

The technical solutions below are provided by the present invention in order to solve the above technical problem.

The first aspect of the technical solution is to provide a nicotinyl alcohol ether derivative represented by formula (I), a stereoisomer thereof and a pharmaceutically-acceptable salt thereof:

wherein:

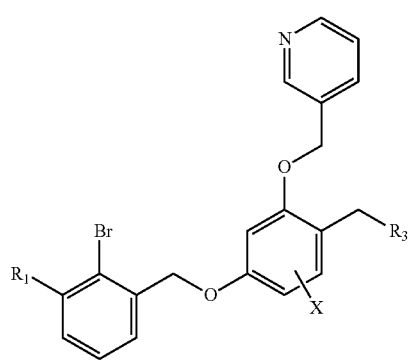
(I)

$R_1$ is selected from

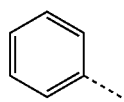

and

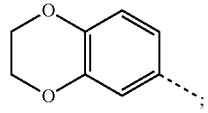

$R_3$ is selected from substituted $C_1$-$C_8$ saturated alkylamino, substituted $C_2$-$C_6$ unsaturated alkylamino, substituted N-containing $C_2$-$C_6$ heterocycle-1-yl, wherein each is mono-, di-, tri-, or tetra-substituted with substituent(s) selected from hydrogen, fluorine, chlorine, bromine, iodine, hydroxy, $C_1$-$C_5$ alkyl, $C_1$-$C_5$ alkoxy, amino, $C_1$-$C_6$ alkylamino, acetylamino, cyano, ureido (—NH(C=O)NH$_2$), guanidino (—NH(C=NH)NH$_2$), ureido amino (—NH—NH(C=O)NH$_2$), guanidino amino (—NH—NH(C=NH)NH$_2$), sulfonylamino (—NHSO$_3$H), sulfamoyl (—SO$_2$NH$_2$), methanesulfonylamino (—NH—SO$_2$CH$_3$), hydroxyformyl (—COOH), $C_1$-$C_8$ alkoxyl carbonyl, sulfydryl, imidazolyl, thiazolyl, oxazolyl, tetrazolyl,

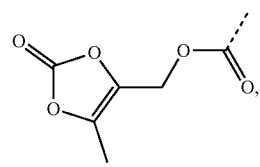

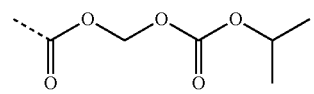

and

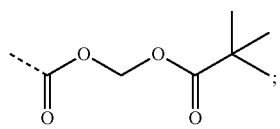

X is selected from hydrogen, fluorine, chlorine, bromine, iodine, $C_1$-$C_4$ alkyl, ethenyl, trifluoromethyl, methoxy.

Preferable are nicotinyl alcohol ether derivatives, stereoisomers thereof and pharmaceutically acceptable salts thereof, wherein the compound is represented by formula (IA):

wherein:

(IA)

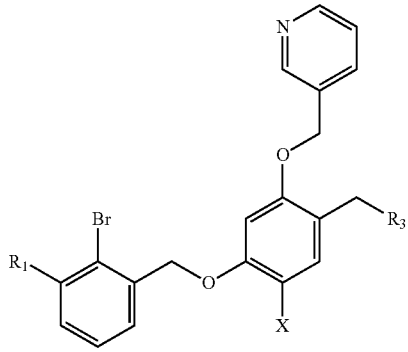

$R_1$ is selected from

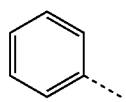

and

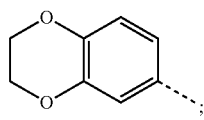

;

$R_3$ is selected from substituted $C_1$-$C_8$ saturated alkylamino, substituted $C_2$-$C_6$ unsaturated alkylamino, substituted N-containing $C_2$-$C_6$ heterocycle-1-yl, wherein each is mono-, di-, tri-, or tetra-substituted with substituent(s) selected from hydrogen, fluorine, chlorine, bromine, iodine, hydroxy, $C_1$-$C_5$ alkyl, $C_1$-$C_5$ alkoxy, amino, $C_1$-$C_6$ alkylamino, acetylamino, cyano, ureido (—NH(C=O)NH$_2$), guanidino (—NH(C=NH)NH$_2$), ureido amino (—NH—NH(C=O)NH$_2$), guanidino amino (—NH—NH(C=NH)NH$_2$), sulfonylamino (—NHSO$_3$H), sulfamoyl (—SO$_2$NH$_2$), methanesulfonylamino (—NH—SO$_2$CH$_3$), hydroxyformyl (—COOH), $C_1$-$C_8$ alkoxyl carbonyl, sulfydryl, imidazolyl, thiazolyl, oxazolyl, tetrazolyl,

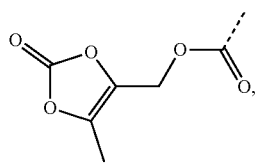

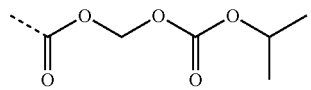

and

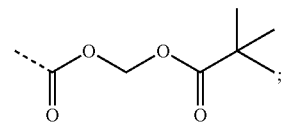

;

X is selected from hydrogen, fluorine, chlorine, bromine, iodine, $C_1$-$C_4$ alkyl, ethenyl, trifluoromethyl, and methoxy.

Preferable are nicotinyl alcohol ether derivatives, stereoisomers thereof and pharmaceutically acceptable salts thereof, wherein the compound is represented by formula (IA-1):

(IA-1)

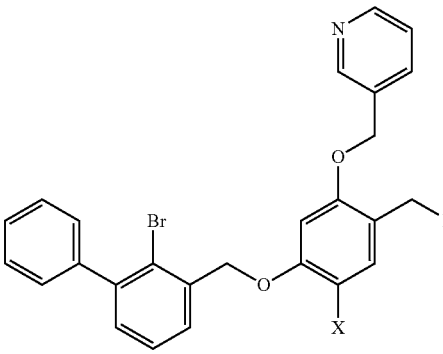

wherein:

$R_3$ is selected from substituted $C_1$-$C_8$ saturated alkylamino, substituted $C_2$-$C_6$ unsaturated alkylamino, substituted N-containing $C_2$-$C_6$ heterocycle-1-yl, wherein each is mono-, di-, tri-, or tetra-substituted with substituent(s) selected from hydrogen, fluorine, chlorine, bromine, iodine, hydroxy, $C_1$-$C_5$ alkyl, $C_1$-$C_5$ alkoxy, amino, $C_1$-$C_6$ alkylamino, acetylamino, cyano, ureido (—NH(C=O)NH$_2$), guanidino (—NH(C=NH)NH$_2$), ureido amino (—NH—NH(C=O)NH$_2$), guanidino amino (—NH—NH(C=NH)NH$_2$), sulfonylamino (—NHSO$_3$H), sulfamoyl (—SO$_2$NH$_2$), methanesulfonylamino (—NH—SO$_2$CH$_3$), hydroxyformyl (—COOH), $C_1$-$C_8$ alkoxyl carbonyl, sulfydryl, imidazolyl, thiazolyl, oxazolyl, tetrazolyl,

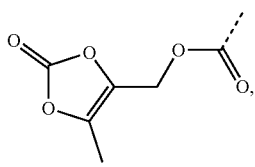

7

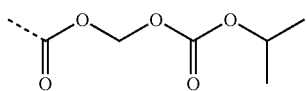

and

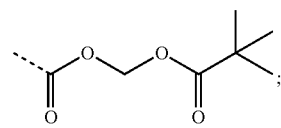

X is selected from hydrogen, fluorine, chlorine, bromine, iodine, $C_1$-$C_4$ alkyl, ethenyl, trifluoromethyl, and methoxy.

Preferable are nicotinyl alcohol ether derivatives, stereoisomers thereof and pharmaceutically acceptable salts thereof, wherein the compound is represented by formula (IA-2):

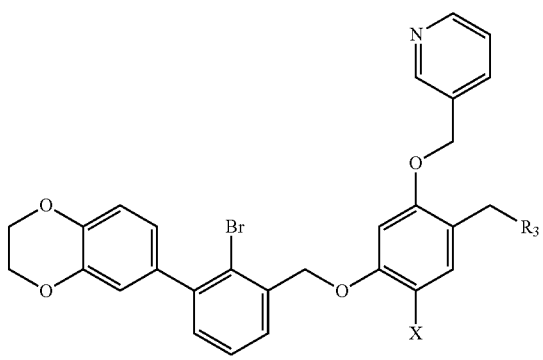

(IA-2)

wherein:

$R_3$ is selected from substituted $C_1$-$C_8$ saturated alkylamino, substituted $C_2$-$C_6$ unsaturated alkylamino, substituted N-containing $C_2$-$C_6$ heterocycle-1-yl, wherein each is mono-, di-, tri-, or tetra-substituted with substituent(s) selected from hydrogen, fluorine, chlorine, bromine, iodine, hydroxy, $C_1$-$C_5$ alkyl, $C_1$-$C_5$ alkoxy, amino, $C_1$-$C_6$ alkylamino, acetylamino, cyano, ureido (—NH(C=O)NH$_2$), guanidine (—NH(C=NH)NH$_2$), ureido amino (—NH—NH(C=O)NH$_2$), guanidino amino (—NH—NH(C=NH)NH$_2$), sulfonylamino (—NHSO$_3$H), sulfamoyl (—SO$_2$NH$_2$), methanesulfonylamino (—NH—SO$_2$CH$_3$), hydroxyformyl (—COOH), $C_1$-$C_8$ alkoxyl carbonyl, sulfydryl, imidazolyl, thiazolyl, oxazolyl, tetrazolyl,

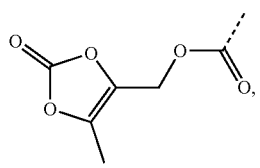

8

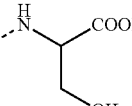

and

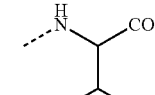

X is selected from hydrogen, fluorine, chlorine, bromine, iodine, $C_1$-$C_4$ alkyl, ethenyl, trifluoromethyl, and methoxy.

Preferable are nicotinyl alcohol ether derivatives, stereoisomers thereof and pharmaceutically acceptable salts thereof, wherein the compound is represented in the above formulae, wherein $R_3$ is selected from:

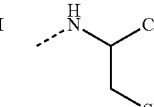 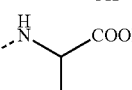 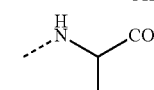

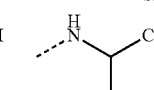 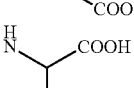 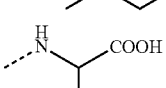

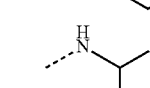  

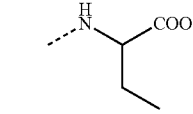 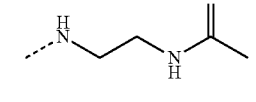 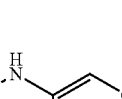

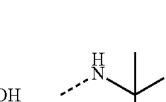 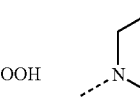

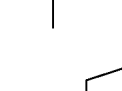  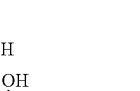

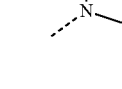 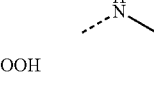 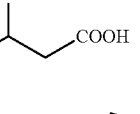

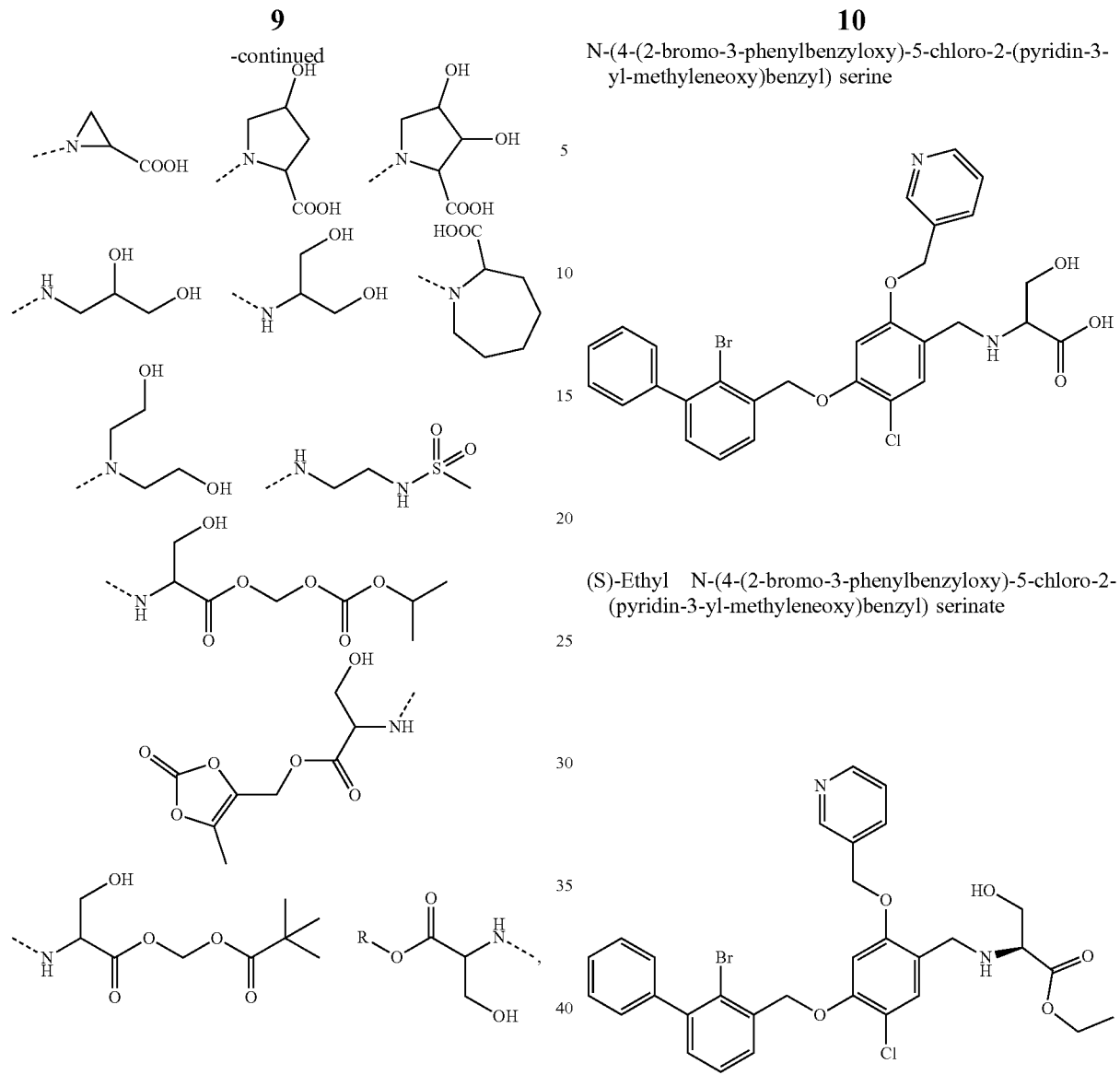

wherein R is selected from methyl, ethyl, propyl, isopropyl, butyl, pentyl, hexyl, heptyl, octyl; and X is selected from hydrogen, fluorine, chlorine, bromine, methyl, ethenyl, and trifluoromethyl.

Most preferable compounds are selected from the following: Ethyl N-(4-(2-bromo-3-phenylbenzyloxy)-5-chloro-2-(pyridin-3-yl-methyleneoxy)benzyl) serinate dihydrochloride N-(4-(2-bromo-3-phenylbenzyloxy)-5-chloro-2-(pyridin-3-yl-methyleneoxy)benzyl) serine (S)-Ethyl N-(4-(2-bromo-3-phenylbenzyloxy)-5-chloro-2-(pyridin-3-yl-methyleneoxy)benzyl) serinate (S)—N-(4-(2-bromo-3-phenylbenzyloxy)-5-chloro-2-(pyridin-3-yl-methyleneoxy) benzyl) serine

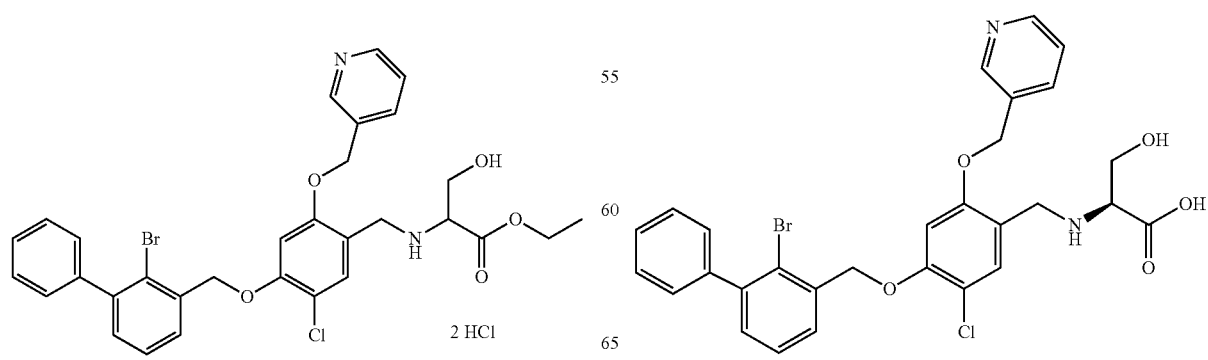

(S)-Ethyl N-(4-(2-bromo-3-phenylbenzyloxy)-5-chloro-2-(pyridin-3-yl-methyleneoxy)benzyl) serinate dihydrochloride (R)—N-(4-(2-bromo-3-phenylbenzyloxy)-5-chloro-2-(pyridin-3-yl-methyleneoxy) benzyl) serine

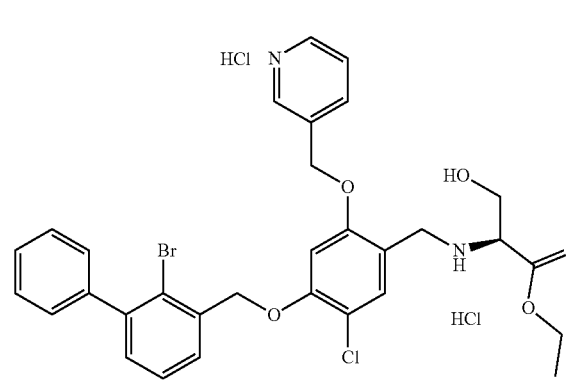

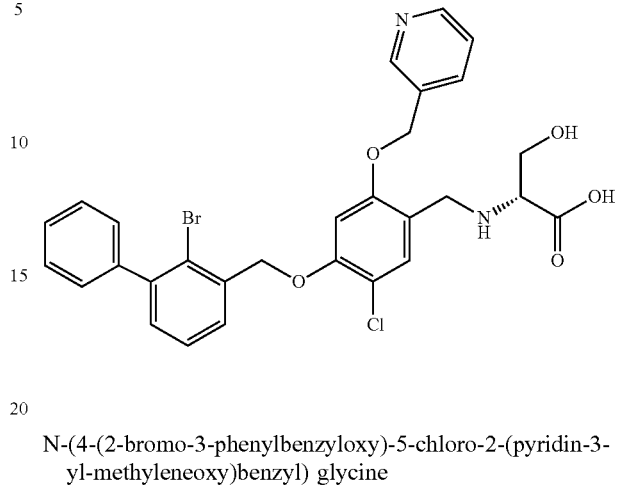

(S)-isopropyl N-(4-(2-bromo-3-phenylbenzyloxy)-5-chloro-2-(pyridin-3-yl-methyleneoxy)benzyl) serinate dihydrochloride N-(4-(2-bromo-3-phenylbenzyloxy)-5-chloro-2-(pyridin-3-yl-methyleneoxy)benzyl) glycine

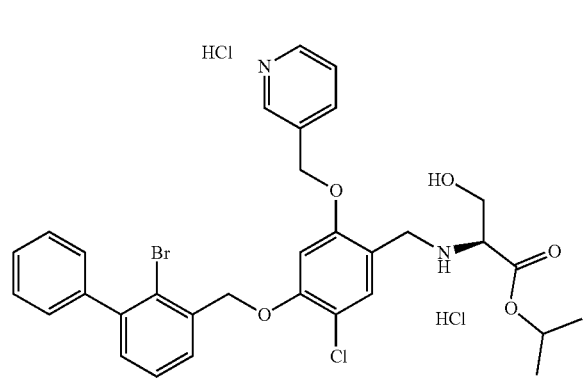 [SMILES: CC(C)OC(=O)[C@H](CO)NCc1cc(Cl)c(OCc2cccc(-c3ccccc3)c2Br)cc1OCc1cccnc1 ; Cl ; Cl]

(R)-Ethyl N-(4-(2-bromo-3-phenylbenzyloxy)-5-chloro-2-(pyridin-3-yl-methyleneoxy)benzyl) serinate N-(4-(2-bromo-3-phenylbenzyloxy)-5-chloro-2-(pyridin-3-yl-methyleneoxy)benzyl) valine

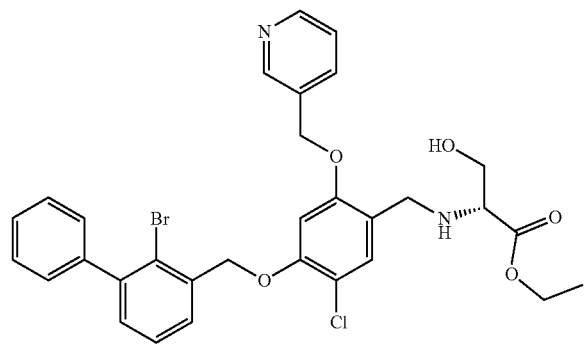 [SMILES: CCOC(=O)[C@@H](CO)NCc1cc(Cl)c(OCc2cccc(-c3ccccc3)c2Br)cc1OCc1cccnc1]

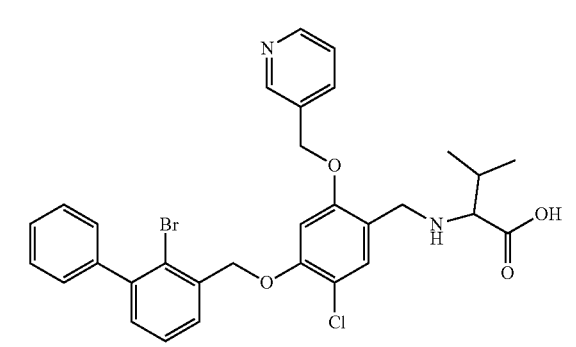 [SMILES: CC(C)C(NCc1cc(Cl)c(OCc2cccc(-c3ccccc3)c2Br)cc1OCc1cccnc1)C(=O)O]

(E)-3-(4-(2-bromo-3-phenylbenzyloxy)-5-chloro-2-(pyridin-3-yl-methyleneoxy) benzylamino) but-2-enenitrile N-(2-acetylaminoethyl)-4-(2-bromo-3-phenylbenzyloxy)-5-chloro-2-(pyridin-3-yl-methyleneoxy) benzylamine

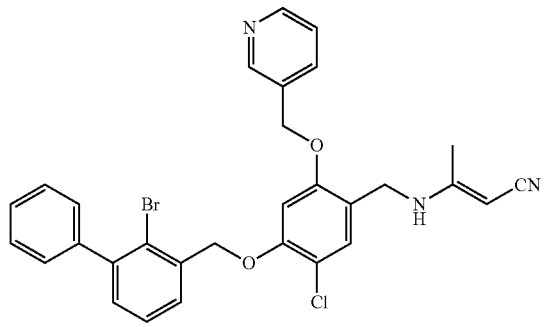 [SMILES: C/C(=C\C#N)NCc1cc(Cl)c(OCc2cccc(-c3ccccc3)c2Br)cc1OCc1cccnc1]

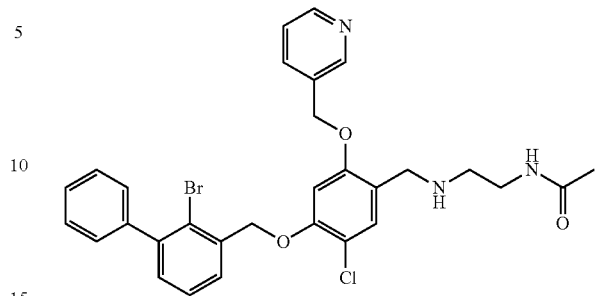

(E)-3-(4-(2-bromo-3-phenylbenzyloxy)-5-chloro-2-(pyridin-3-yl-methyleneoxy) benzylamino) but-2-enoic acid N,N-bis(hydroxyethyl)-4-(2-bromo-3-phenylbenzyloxy)-5-chloro-2-(pyridin-3-yl-methyleneoxy) benzylamine

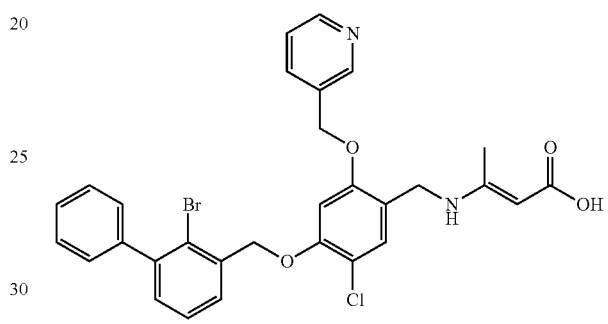

2-(4-(2-bromo-3-phenylbenzyloxy)-5-chloro-2-(pyridin-3-yl-methyleneoxy) benzylamino) ethanesulfonic acid

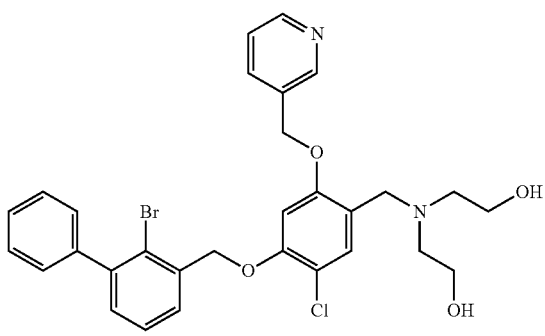 [SMILES: OCCN(CCO)Cc1cc(Cl)c(OCc2cccc(-c3ccccc3)c2Br)cc1OCc1cccnc1]

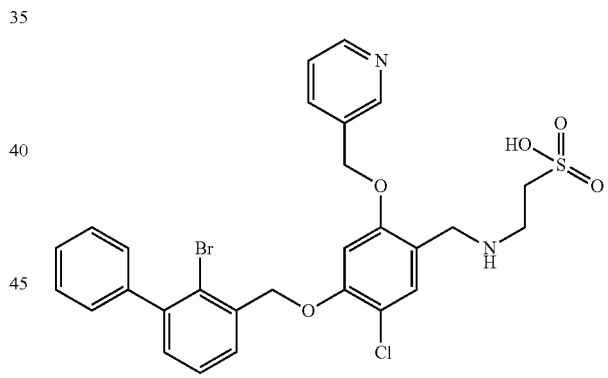

N-(2-methanesulfonamidoethyl)-4-(2-bromo-3-phenylbenzyloxy)-5-chloro-2-(pyridin-3-yl-methyleneoxy) benzylamine N-(4-(2-bromo-3-phenylbenzyloxy)-5-chloro-2-(pyridin-3-yl-methyleneoxy)benzyl) leucine

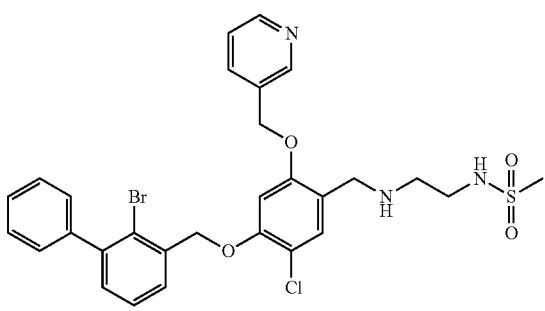 [SMILES: CS(=O)(=O)NCCNCc1cc(Cl)c(OCc2cccc(-c3ccccc3)c2Br)cc1OCc1cccnc1]

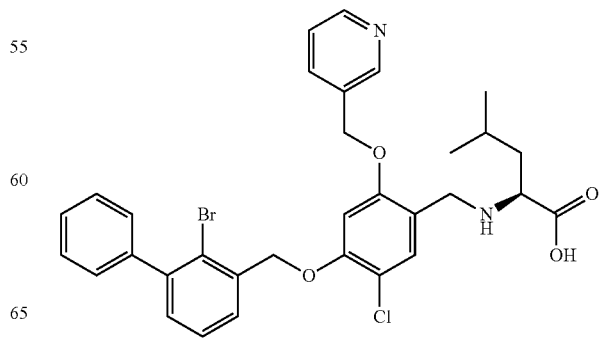

15

N-(4-(2-bromo-3-phenylbenzyloxy)-5-chloro-2-(pyridin-3-yl-methyleneoxy)benzyl) tyrosine

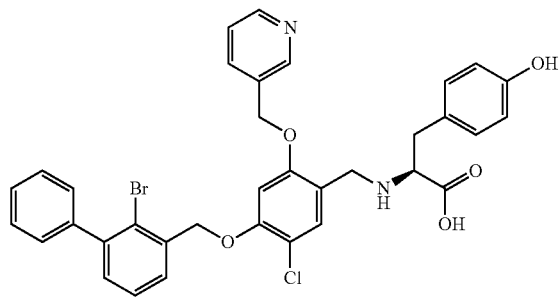 [SMILES: O=C(O)[C@H](Cc1ccc(O)cc1)NCc1cc(Cl)c(OCc2cccc(-c3ccccc3)c2Br)cc1OCc1cccnc1]

N-(4-(2-bromo-3-phenylbenzyloxy)-5-chloro-2-(pyridin-3-yl-methyleneoxy)benzyl) isoleucine

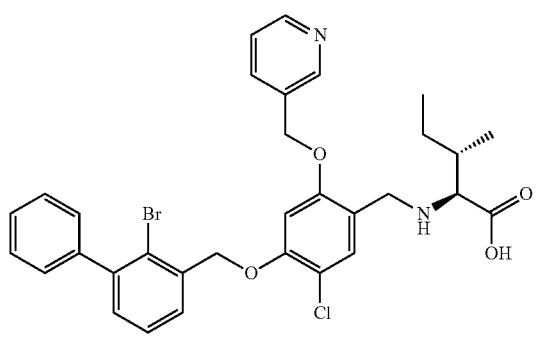 [SMILES: CC[C@H](C)[C@H](NCc1cc(Cl)c(OCc2cccc(-c3ccccc3)c2Br)cc1OCc1cccnc1)C(=O)O]

N-(4-(2-bromo-3-phenylbenzyloxy)-5-chloro-2-(pyridin-3-yl-methyleneoxy)benzyl) asparagine

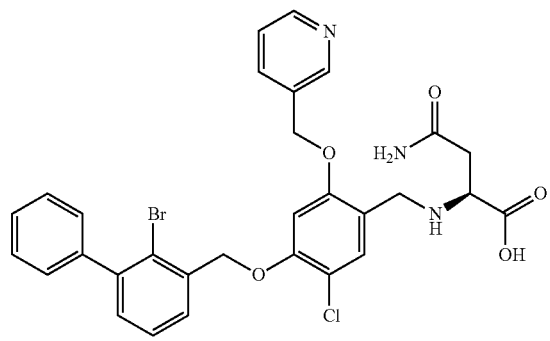 [SMILES: NC(=O)C[C@H](NCc1cc(Cl)c(OCc2cccc(-c3ccccc3)c2Br)cc1OCc1cccnc1)C(=O)O]

16

N-(hydroxyethyl)-4-(2-bromo-3-phenylbenzyloxy)-5-chloro-2-(pyridin-3-yl-methyleneoxy) benzylamine

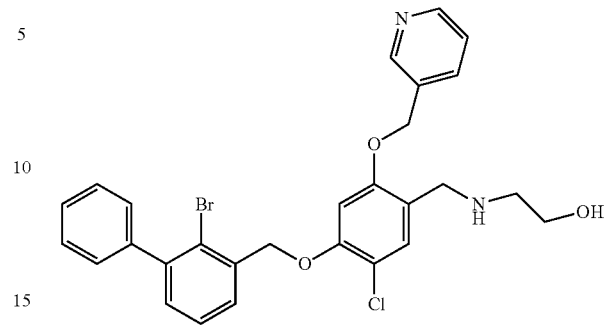

N-(4-(2-bromo-3-phenylbenzyloxy)-5-chloro-2-(pyridin-3-yl-methyleneoxy)benzyl) alanine

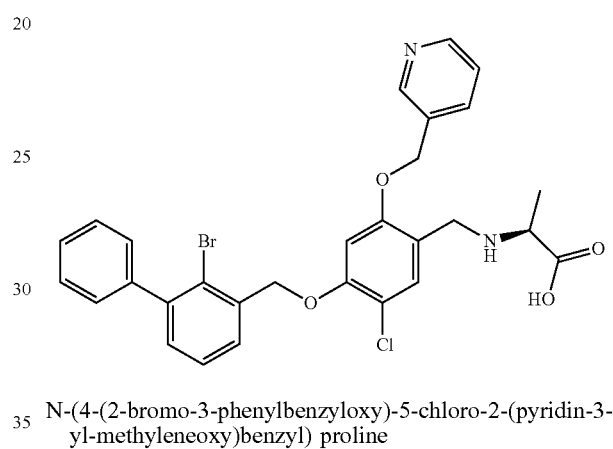

N-(4-(2-bromo-3-phenylbenzyloxy)-5-chloro-2-(pyridin-3-yl-methyleneoxy)benzyl) proline

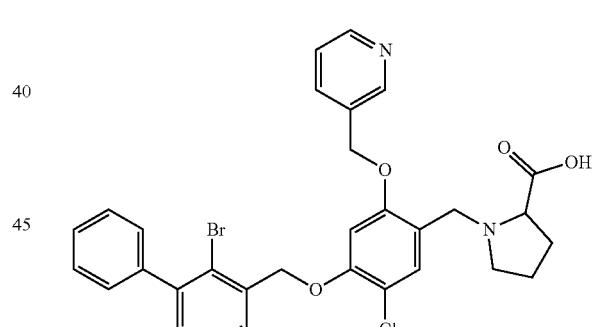

(S)-Sodium N-(4-(2-bromo-3-phenylbenzyloxy)-5-chloro-2-(pyridin-3-yl-methyleneoxy)benzyl) serinate

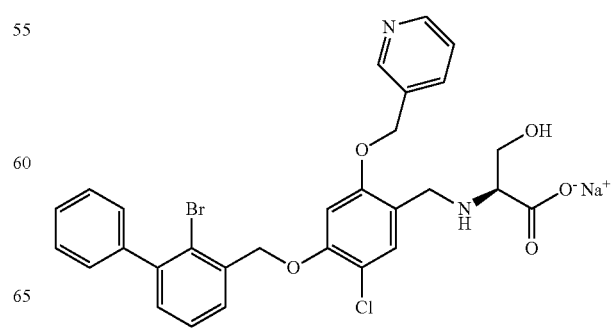

(S)-Calcium N-(4-(2-bromo-3-phenylbenzyloxy)-5-chloro-2-(pyridin-3-yl-methyleneoxy)benzyl) serinate

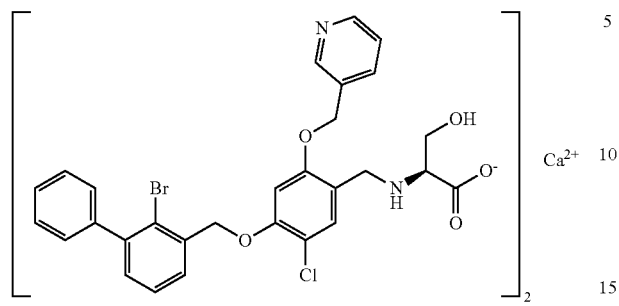

(S)-(5-methyl-2-oxo-1,3-dioxol-4-yl)methyl N-(4-(2-bromo-3-phenylbenzyloxy)-5-chloro-2-(pyridin-3-yl-methyleneoxy)benzyl) serinate

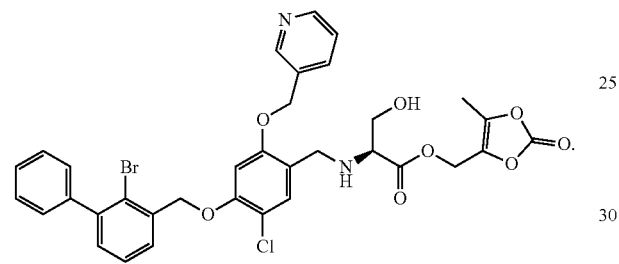

The nicotinyl alcohol ether derivative of the above formulae, a stereoisomer thereof and a pharmaceutically acceptable salt thereof, are characterized in that, the pharmaceutically acceptable salt comprises a salt formed with an inorganic acid, a salt formed with an organic acid salt, alkali metal ion salt, alkaline earth metal ion salt or a salt formed with organic base which provides a physiologically acceptable cation, and an ammonium salt.

Said inorganic acid is selected from hydrochloric acid, hydrobromic acid, phosphoric acid or sulfuric acid; said organic acid is selected from methanesulfonic acid, p-toluenesulfonic acid, trifluoroacetic acid, citric acid, maleic acid, tartaric acid, fumaric acid, citric acid or lactic acid; said alkali metal ion is selected from lithium ion, sodium ion, potassium ion; said alkaline earth metal ion is selected from calcium ion, magnesium ion; said organic base, which provides physiologically acceptable cation, is selected from methylamine, dimethylamine, trimethylamine, piperidine, morpholine or tris(2-hydroxyethyl)amine.

The second aspect of the present invention provides a method for preparing the compounds of the first aspect.

For the preparation of the compounds of the formula (I), according to its structure, the preparation method is divided into five steps.

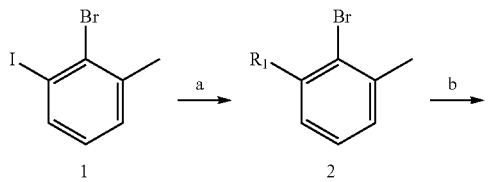

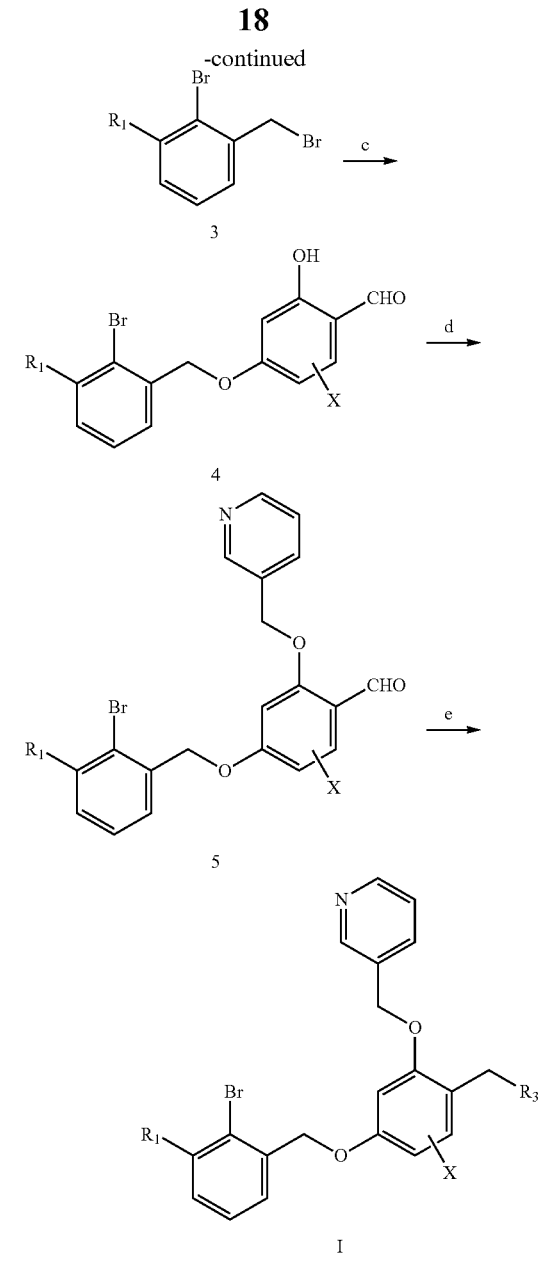

(a) 2-bromo-3-iodotoluene 1 and benzene boronic acid or substituted benzene boronic acid or boric acid ester of benzene or substituted benzene as starting materials are reacted via suzuki coupling reaction to obtain Intermediate compound 2;
(b) intermediate 2 as a starting material is subjected to bromination of the methyl group by a bromination reagent to give the bromo intermediate 3;
(c) intermediate 3 as a starting material is reacted with 2,4-dihydroxy-X-substituted benzaldehyde under basic conditions to obtain benzyl aryl ether intermediate 4;
(d) intermediate 4 as a starting material is reacted with pyridin-3-yl-methylene halide under basic conditions to give intermediate compound 5;
(e) an aldehyde group-containing intermediate compound 5 as a starting material is condensed with an amino group- or an imino group-containing HR₃ and the resultant product is reduced to obtain the target compound I.

$R_1$, $R_3$ and X each is defined as described in the first aspect.

In addition, the starting materials and intermediates in the above reaction are obtained easily, and the each step reaction can be performed easily according to the reported literature or by a skilled worker in the art by a conventional method in organic synthesis. The compound of formula I may exist in solvated or unsolvated forms, and crystallization from different solvents may result in different solvates. The pharmaceutically acceptable salts of the formula (I) include different acid addition salts, such as the acid addition salts of the following inorganic or organic acids: hydrochloric acid, hydrobromic acid, phosphoric acid, sulfuric acid, methanesulfonic acid, p-toluenesulfonic acid, Trifluoroacetic acid, citric acid, maleic acid, tartaric acid, fumaric acid, citric acid, lactic acid. The pharmaceutically acceptable salts of formula I also include various alkali metal salts such as lithium, sodium, potassium salts; various alkaline-earth metal salts such as calcium, magnesium salts and ammonium salts; and various organic base salts which provide physiologically acceptable cations, such as methylamine, dimethylamine, trimethylamine, piperidine, morpholine salts and tris(2-hydroxyethyl)amine salts. All of these salts within the scope of the invention can be prepared by conventional methods. During the preparation of the compounds of the formula (I) and their solvates or salts, polycrystalline or eutectic may occur under different crystallization conditions.

The third aspect of the present invention provides a pharmaceutical composition comprising which includes the nicotinyl alcohol ether derivative of the first aspect of the present invention and a stereoisomer thereof, and the pharmaceutically acceptable salt as an active ingredient and a pharmaceutically acceptable carrier or excipient.

The invention further relates to a pharmaceutical composition comprising a compound of the invention as an active ingredient. The pharmaceutical composition can be prepared according to methods well known in the art. Any dosage form suitable for human or animal use can be prepared by combining a compound of the invention with one or more pharmaceutically acceptable excipients and/or adjuvants in solid or liquid. The content of the compound of the present invention in its pharmaceutical composition is usually from 0.1 to 95% by weight.

The compound of the present invention or the pharmaceutical composition containing the same can be administered in a unit dosage form, via enteral or parenteral route, such as oral, intravenous, intramuscular, subcutaneous, nasal, oral mucosa, eye, lung and the respiratory tract, skin, vagina, rectum, etc.

The dosage form can be a liquid dosage form, a solid dosage form or a semi-solid dosage form. Liquid dosage forms can be solution (including true solution and colloidal solution), emulsion (including o/w type, w/o type and double emulsion), suspension, injection (including water injection, powder injection and infusion), eye drops, nasal drops, lotions, liniments, etc.; solid dosage forms may be tablets (including ordinary tablets, enteric tablets, lozenges, dispersible tablets, chewable tablets, effervescent tablets, orally disintegrating tablets), capsules (including hard capsules, soft capsules, enteric capsules), granules, powders, pellets, dropping pills, suppositories, films, patches, gas (powder) sprays, sprays, etc.; semi-solid dosage forms can be ointments, gel, paste, etc.

The compounds of the present invention can be formulated into common preparations, as well as sustained release preparations, controlled release preparations, targeted preparations, and various microparticle delivery systems.

In order to form tablets of the compound of the present invention into, various excipients known in the art, including diluents, binders, wetting agents, disintegrating agents, lubricants, and glidants, can be used widely. The diluent may be starch, dextrin, sucrose, glucose, lactose, mannitol, sorbitol, xylitol, microcrystalline cellulose, calcium sulfate, calcium hydrogen phosphate, calcium carbonate, etc.; the wetting agent may be water, ethanol, or isopropanol, etc.; the binder may be starch syrup, dextrin, syrup, honey, glucose solution, microcrystalline cellulose, acacia mucilage, gelatine, sodium carboxymethyl cellulose, methyl cellulose, hydroxypropylmethyl cellulose, ethyl cellulose, acrylic resin, carbomer, polyvinylpyrrolidone, polyethylene glycol, etc.; disintegrants can be dry starch, microcrystalline cellulose, low-substituted hydroxypropyl cellulose, cross-linked poly vinyl pyrrolidone, croscarmellose sodium, sodium carboxymethyl starch, sodium hydrogencarbonate and citric acid, polyoxyethylene sorbitan fatty acid ester, sodium dodecyl sulfonate, etc.; lubricant and glidant may be talc, silica, stearate, tartaric acid, liquid paraffin, polyethylene glycol, etc.

Tablets may also be further formulated into coated tablets such as sugar coated tablets, film-coated tablets, enteric coated tablets, or bilayer tablets and multilayer tablets.

In order to prepare the dose unit as a capsule, the active ingredient compound of the present invention may be mixed with a diluent, a glidant, and the mixture may be directly placed in a hard capsule or a soft capsule. The active ingredient can also be formulated into a granule or pellet with a diluent, a binder, a disintegrant, and then placed in a hard or soft capsule. Various diluents, binders, wetting agents, disintegrating agents and glidants for preparing the tablets of the compound of the invention can also be used to prepare the capsules of the compound of the invention.

In order to prepare the compound of the present invention as an injection, water, ethanol, isopropanol, propylene glycol or their mixture may be used as a solvent. In addition, an appropriate amount of a solubilizing agent, a co-solvent, a pH adjusting agent, and an osmotic pressure adjusting agent which are commonly used in the art can be added. The solubilizing agent or co-solvent may be poloxamer, lecithin, hydroxypropyl-β-cyclodextrin, etc.; the pH adjusting agent may be phosphate, acetate, hydrochloric acid, sodium hydroxide, etc.; osmotic pressure regulating agent may be sodium chloride, mannitol, glucose, phosphate, acetate, etc. For preparing a lyophilized powder injection, mannitol, glucose and so on may also be added as a proppant.

In addition, coloring agents, preservatives, perfumes, flavoring agents or other additives may also be added to the pharmaceutical preparations as needed.

The compound or pharmaceutical composition of the present invention can be administered by any known administration method for the purpose of administration and enhancing the therapeutic effect.

The dosage of the compound or the pharmaceutical composition of the present invention can be administered in a wide range depending on the nature and severity of the disease to be prevented or treated, the individual condition of the patient or animal, the route of administration and the dosage form, etc. In general, a suitable daily dose of the compound of the invention will range from 0.001 to 150 mg/kg body weight, preferably from 0.01 to 100 mg/kg body weight. The above dosages may be administered in a single dosage unit or in divided dose units depending on the clinical experience of the physician and the dosage regimen including the use of other therapeutic means.

The compounds or compositions of the invention may be administered alone or in combination with other therapeutic or symptomatic agents. When the compound of the present invention synergizes with other therapeutic agents, its dosage should be adjusted according to the actual situation.

The fourth aspect of the present invention provides a nicotinyl alcohol ether derivative, or a stereoisomer thereof, or a pharmaceutically acceptable salt thereof, which are used for the preparation of a medicament useful for preventing and/or treating a disease associated with the PD-1/PD-L1 signaling pathway.

The disease associated with the PD-1/PD-L1 signaling pathway is selected from cancer, infectious diseases, and autoimmune diseases. The cancer is selected from skin cancer, lung cancer, urinary tumor, hematological tumor, breast cancer, glioma, digestive system tumor, reproductive system tumor, lymphoma, nervous system tumor, brain tumor, head and neck cancer. The infectious disease is selected from bacterial infection and viral infection. The autoimmune disease is selected from organ-specific autoimmune disease, systemic autoimmune disease, wherein the organ-specific autoimmune disease includes chronic lymphocytic thyroiditis, hyperthyroidism, insulin-dependent diabetes mellitus, myasthenia gravis, ulcerative colitis, malignant anemia with chronic atrophic gastritis, pulmonary hemorrhagic nephritis syndrome, primary biliary cirrhosis, multiple cerebrospinal sclerosis, and acute idiopathic polyneuritis. And the systemic autoimmune diseases include rheumatoid arthritis, systemic lupus erythematosus, systemic vasculitis, scleroderma, pemphigus, dermatomyositis, mixed connective tissue disease, autoimmune hemolytic anemia.

Beneficial Technical Effects

The compounds of the present invention have high inhibitory activity on PD-1/PD-L1 interaction, much higher than the reported compounds. They have strong ability of binding PD-L1 protein, and the kD value of affinity can reach 2.025E-11, even stronger than the reported antibodies of PD-L1. These compounds also have the ability to relieve the inhibition of IFN-γ by PD-L1, whose $IC_{50}$ value can reach $1.8 \times 10^{-10}$ mol/L level. The pharmacodynamic studies in vivo show that the compounds can significantly inhibit the growth of subcutaneous tumors in both tumor volume and weight. The number of lymphocytes in blood and spleen of mice can be increased obviously.

EXAMPLES

The invention is further illustrated by the following examples; however, the invention is not limited by the illustrative examples set herein below.

Measuring instrument: Nuclear magnetic resonance spectroscopy was carried out by using a Vaariaan Mercury 300 nuclear magnetic resonance apparatus. Mass spectrometry was performed by using ZAD-2F mass spectrometer and VG300 mass spectrometer.

Example 1

Ethyl N-(4-(2-bromo-3-phenylbenzyloxy)-5-chloro-2-(pyridin-3-yl-methyleneoxy)benzyl) serinate dihydrochloride

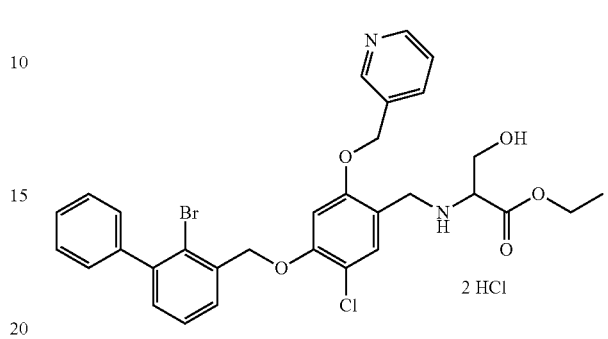

2-Bromo-3-methyl-1,1'-biphenyl

To a 100 ml flask were added 2-bromo-3-iodotoluene (700 mg) and dioxane/water (volume ratio 5/1) with stirring. The solution was bubbled with argon for 10 min to remove dissolved oxygen. Then, phenylboronic acid (350 mg), cesium carbonate (1800 mg), and triphenylphosphine palladium (80 mg) were sequentially added. The mixture was stirred for 12 h at 80-100° C. under argon protection. The reaction was stopped. After cooling to room temperature, the mixture was filtered with diatomaceous earth. The filtrate was concentrated under reduced pressure and extracted with water and ethyl acetate for three times. The organic phase was combined, washed with saturated brine, and dried over anhydrous sodium sulfate. The organic layer was filtered and evaporated under reduced pressure to dryness to afford 2-bromo-3-methyl-1,1'-biphenyl as colorless oil (480 mg). $^1$H NMR (400 MHz, DMSO-$d_6$), δ 7.49-7.29 (m, 7H, Ar—H), 7.14 (d, 1H, Ar—H), 2.42 (s, 3H, Ar—$CH_3$). MS (FAB): 248 (M+1).

2-Bromo-3-(bromomethyl)-1,1'-biphenyl

2-Bromo-3-methyl-1,1'-biphenyl (450 mg) as a starting material was weighed and was dissolved in 40 ml of $CCl_4$ in a 100 ml flask. To this solution was added NBS (360 mg) while stirring. And the mixture was warmed to 80° C. and refluxed. Then benzoyl peroxide (8 mg) was added, and after 2 h, benzoyl peroxide (8 mg) was added again, and the reaction was continued for another 2 h. The reaction was stopped. After cooling to room temperature, the mixture was quenched with water, extracted with dichloromethane and water. The organic phase was washed with saturated brine, and dried over anhydrous sodium sulfate. The organic layer was filtered and evaporated under reduced pressure to dryness to afford 2-bromo-3-(bromomethyl)-1,1'-biphenyl as yellow oil (380 mg), which was used for the next step without further purification.

4-(2-bromo-3-phenylbenzyloxy)-5-chloro-2-hydroxybenzaldehyde 5-chloro-2, 4-dihydroxybenzaldehyde (160 mg) was weighed and dissolved in 12 ml of anhydrous acetonitrile in a 50 ml flask, and sodium hydrogen carbonate (200 mg) was added. After stirring at room temperature for 40 min, 2-bromo-3-phenylbenzyl bromide (380 mg, dissolved in 16 ml of DMF) was slowly added dropwise to the reaction mixture via a constant pressure dropping funnel, and heated to reflux until the reaction was completed. After cooling to room temperature, the mixture was extracted with water and ethyl acetate. The organic phase was washed with saturated brine, and dried over anhydrous sodium sulfate, then filtrated and evaporated under reduced pressure to dryness. The crude residue was purified by silica gel column chromatography to afford 4-(2-bromo-3-phenylbenzyloxy)-5-chloro-2-hydroxy benzaldehyde (300 mg) as a white solid. $^1$H NMR (400 MHz, DMSO-$d_6$) δ 10.99 (s, 1H, —OH), 10.03 (s, 1H, —CHO), 7.64 (d, 1H, Ar—H), 7.57 (d, 1H, Ar—H), 7.45 (m, 4H, Ar—H), 7.37 (d, 2H, Ar—H), 6.67 (d, 1H, Ar—H), 6.59 (s, 1H, Ar—H), 5.25 (s, 2H, —CH$_2$—). MS (FAB): 418 (M+1).

4-(2-bromo-3-phenylbenzyloxy)-5-chloro-2-(pyridin-3-yl-methyleneoxy) benzaldehyde 4-(2-bromo-3-phenylbenzyloxy)-5-chloro-2-hydroxybenzaldehyde (100 mg) was dissolved in 6 ml of DMF in a 50 ml flask, and then cesium carbonate (127.53 mg) was added. After stirring at room temperature for 15 min, a solution of 3-bromomethylenepyridine (76.65 mg) in DMF (4 ml) was added dropwise. After the mixture was stirred at 80° C. for 2 h, the reaction was stopped. After cooling to room temperature, the mixture was extracted with water and ethyl acetate. The organic phase was washed with saturated brine, and dried over anhydrous sodium sulfate, then filtrated and evaporated under reduced pressure to dryness. The crude residue was purified by silica gel column chromatography to afford a white solid (70 mg). $^1$H NMR (400 MHz, DMSO-$d_6$) δ 10.26 (s, 1H, —CHO), 8.00 (s, 1H, Ar—H), 7.83 (dd, 2H, Ar—H), 7.72 (d, 1H, Ar—H), 7.61 (t, 2H, Ar—H), 7.55-7.23 (m, 6H, Ar—H), 6.95 (s, 1H, Ar—H), 6.81 (d, 1H, Ar—H), 5.35 (s, 2H, —CH$_2$—), 5.30 (s, 2H, —CH$_2$—). MS (FAB): 510 (M+1).

Ethyl N-(4-(2-bromo-3-phenylbenzyloxy)-5-chloro-2-(pyridin-3-yl-methyleneoxy)benzyl) serinate dihydrochloride 4-(2-bromo-3-phenylbenzyloxy)-5-chloro-2-(pyridin-3-yl-methyleneoxy)benzalde hyde (80 mg) was dissolved in 5 ml of DMF, and then racemic ethyl ester of serine (59 mg) and acetic acid glacial (57 mg) were added. After stirring at room temperature for 20 min, sodium cyanoborohydride (25 mg) was added and the mixture was stirred at 25° C. for 14 h. The reaction was stopped. The mixture was extracted with water and ethyl acetate. The organic phase was washed with saturated brine, and dried over anhydrous sodium sulfate, then filtrated and evaporated under reduced pressure to dryness. The residue was dissolved in ethanol, heated to reflux until the reaction was complete. The mixture was evaporated to dryness. The crude residue was purified by silica gel column chromatography to afford ethyl N-(4-(2-bromo-3-phenylbenzyloxy)-5-chloro-2-(pyridin-3-yl-methyleneoxy)benzyl) serinate (60 mg) as yellow oil. The product was then reacted with a solution of hydrogen chloride in ethanol to afford N-(4-(2-bromo-3-phenylbenzyloxy)-5-chloro-2-(pyridin-3-yl-methyleneoxy)benzyl) serinate dihydrochloride as a white solid. $^1$H NMR (400 MHz, DMSO-$d_6$) δ 9.65 (s, 1H, —HCl), 9.41 (s, 1H, —HCl), 9.06 (s, 1H, —ArH), 8.88-8.76 (m, 1H, —ArH), 8.56 (d, J=7.9 Hz, 1H, —ArH), 8.01-7.86 (m, 1H, —ArH), 7.64 (d, J=13.4 Hz, 2H, —ArH), 7.56-7.30 (m, 7H, —ArH), 7.12 (s, 1H, —ArH), 5.42 (s, 2H, —CH$_2$—), 5.32 (s, 2H, —CH$_2$—), 4.18 (s, 2H, —CH$_2$—), 4.13-4.07 (m, 1H, —CH—), 4.04 (m, 2H, —CH$_2$—), 3.94 (dd, 1H, —CH$_2$—), 3.82 (dd, 1H, —CH$_2$—), 1.15 (t, J=7.1 Hz, 3H, —CH$_3$). MS (FAB): 626 (M).

Example 2

N-(4-(2-bromo-3-phenylbenzyloxy)-5-chloro-2-(pyridin-3-yl-methyleneoxy)benzyl) serine

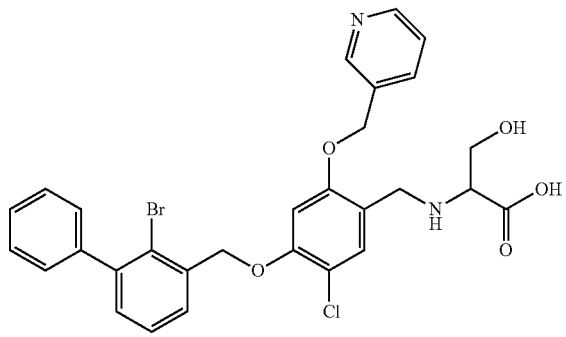

Ethyl N-(4-(2-bromo-3-phenylbenzyloxy)-5-chloro-2-(pyridin-3-yl-methyleneoxy)benzyl) serinate as pale yellow oil (60 mg) was dissolved in methanol/H$_2$O (4 ml/1 ml), and then lithium hydroxide monohydrate (20 mg) was added. After stirring at room temperature for 2 h, a few drops of acetic acid were added to the mixture in an ice bath to adjust the pH to acidity. The mixture was filtrated under reduced pressure to afford N-(4-(2-bromo-3-phenylbenzyloxy)-5-chloro-2-(pyridin-3-yl-methyleneoxy)benzyl) serine (45 mg) as a white solid. $^1$H NMR (400 MHz, DMSO-$d_6$) δ 8.73 (s, 1H, —ArH), 8.55 (d, 1H, —ArH), 7.97 (d, 1H, —ArH), 7.65 (d, 1H, —ArH), 7.54-7.51 (m, 2H, —ArH), 7.47 (d, 2H, —ArH), 7.44 (dl H, —ArH), 7.42-7.40 (m, 2H, —ArH), 7.39-7.36 (m, 2H, —ArH), 7.11 (s, 1H, —ArH), 5.32 (s, 2H, —CH$_2$—), 5.28 (m, 2H, —CH$_2$—), 3.94 (s, 2H, —CH$_2$—), 3.69 (dd, 1H, —CH$_2$—), 3.62 (dd, 1H, —CH$_2$—), 3.16 (t, 1H, —CH—). MS (FAB): 599 (M+1).

Example 3

(S)-Ethyl N-(4-(2-bromo-3-phenylbenzyloxy)-5-chloro-2-(pyridin-3-yl-methyleneoxy)benzyl) serinate

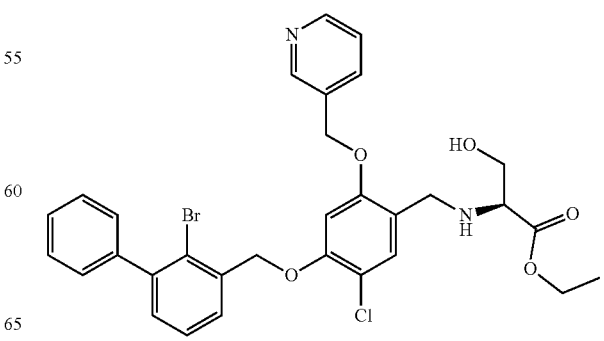

The procedure was the same as in Example 1, except that ethyl ester of L-serine was used in place of racemic ethyl ester of serine to afford (S)-Ethyl N-(4-(2-bromo-3-phenylbenzyloxy)-5-chloro-2-(pyridin-3-yl-methyleneoxy)benzyl) serinate as a white solid. $^1$H NMR (400 MHz, DMSO-$d_6$) δ 8.68 (d, J=2.1 Hz, 1H, —ArH), 8.55 (dd, J=4.8, 1.7 Hz, 1H, —ArH), 7.88 (d, J=7.9 Hz, 1H, —ArH), 7.65 (dd, J=7.6, 1.7 Hz, 1H, —ArH), 7.54-7.45 (m, 3H, —ArH), 7.45-7.35 (m, 6H, —ArH), 7.06 (s, 1H, —ArH), 5.30 (s, 2H, —CH$_2$—), 5.24 (s, 2H, —CH$_2$—), 4.81 (t, J=5.8 Hz, 1H, —CH—), 3.99 (q, J=7.1 Hz, 2H, —CH$_2$—), 3.74-3.57 (m, 2H, —CH$_2$—), 3.54 (t, J=5.6 Hz, 2H, —CH$_2$—), 1.12 (t, J=7.1 Hz, 3H, —CH$_3$). MS (FAB): 626 (M).

Example 4

(S)—N-(4-(2-bromo-3-phenylbenzyloxy)-5-chloro-2-(pyridin-3-yl-methyleneoxy)benzyl) serine

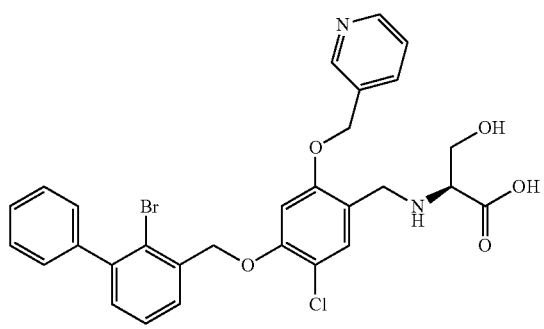 [SMILES: O=C(O)[C@H](CO)NCc1cc(Cl)c(OCc2cccc(-c3ccccc3)c2Br)cc1OCc1cccnc1]

The procedure was the same as in Example 2, except that (S)-Ethyl N-(4-(2-bromo-3-phenylbenzyloxy)-5-chloro-2-(pyridin-3-yl-methyleneoxy)benzyl) serinate was used in place of racemic Ethyl N-(4-(2-bromo-3-phenylbenzyloxy)-5-chloro-2-(pyridin-3-yl-methyleneoxy)benzyl) serinate to afford (S)—N-(4-(2-bromo-3-phenylbenzyloxy)-5-chloro-2-(pyridin-3-yl-methyleneoxy)benzyl) serine as a white solid. $^1$H NMR (400 MHz, DMSO-$d_6$) δ 8.73 (s, 1H, —ArH), 8.55 (d, J=4.7 Hz, 1H, —ArH), 7.97 (d, J=7.9 Hz, 1H, —ArH), 7.65 (d, J=8.7 Hz, 1H, —ArH), 7.54-7.51 (m, 2H, —ArH), 7.47 (d, J=7.7 Hz, 2H, —ArH), 7.44 (d, J=1.7 Hz, 1H, —ArH), 7.42-7.40 (m, 2H, —ArH), 7.39-7.36 (m, 2H, —ArH), 7.11 (s, 1H, —ArH), 5.32 (s, 2H, —CH$_2$—), 5.28 (m, 2H, —CH$_2$—), 3.94 (s, 2H, —CH$_2$—), 3.69 (dd, J=11.1, 4.7 Hz, 1H, —CH$_2$—), 3.62 (dd, J=11.1, 6.2 Hz, 1H, —CH$_2$—), 3.16 (t, J=5.4 Hz, 1H, —CH—). MS (FAB): 599 (M+1). [α]$^{27}_D$=−1.84 (C=0.434, DMSO).

Example 5

(S)-Ethyl N-(4-(2-bromo-3-phenylbenzyloxy)-5-chloro-2-(pyridin-3-yl-methyleneoxy)benzyl) serinate dihydrochloride

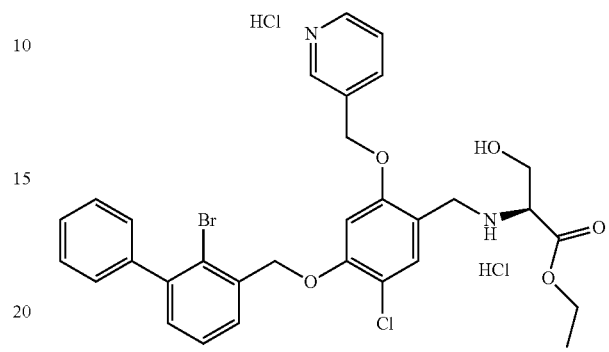

(S)—N-(4-(2-bromo-3-phenylbenzyloxy)-5-chloro-2-(pyridin-3-yl-methyleneoxy) benzyl) serine (598 mg) and 60 ml of anhydrous ethanol were placed in a 100 ml round-bottom flask. To the mixture were added 6 ml of dichlorosulfoxide and two drops of DMF with stirring in an ice water bath. And after the mixture was stirred at room temperature for 2 h it was heated to reflux until the reaction was completed. The mixture was concentrated under reduced pressure to remove the solvent and afford (S)-ethyl N-(4-(2-bromo-3-phenylbenzyloxy)-5-chloro-2-(pyridin-3-yl-methyleneoxy)benzyl) serinate dihydrochloride as a white solid. $^1$H NMR (400 MHz, DMSO-$d_6$) δ 9.65 (s, 1H, —HCl), 9.41 (s, 1H, —HCl), 9.06 (s, 1H, —ArH), 8.88-8.76 (m, 1H, —ArH), 8.56 (d, J=7.9 Hz, 1H, —ArH), 8.01-7.86 (m, 1H, —ArH), 7.64 (d, J=13.4 Hz, 2H, —ArH), 7.56-7.30 (m, 7H, —ArH), 7.12 (s, 1H, —ArH), 5.42 (s, 2H, —CH$_2$—), 5.32 (s, 2H, —CH$_2$—), 4.18 (s, 2H, —CH$_2$—), 4.13-4.07 (m, 1H, —CH—), 4.04 (m, 2H, —CH$_2$—), 3.94 (dd, J=12.1, 2.9 Hz, 1H, —CH$_2$—), 3.82 (dd, J=12.1, 3.8 Hz, 1H, —CH$_2$—), 1.15 (t, J=7.1 Hz, 3H, —CH$_3$). MS (FAB): 626 (M). [α]$^{27}_D$=−1.90 (C=0.422, ethanol).

Example 6

(S)-isopropyl N-(4-(2-bromo-3-phenylbenzyloxy)-5-chloro-2-(pyridin-3-yl-methyleneoxy)benzyl) serinate dihydrochloride

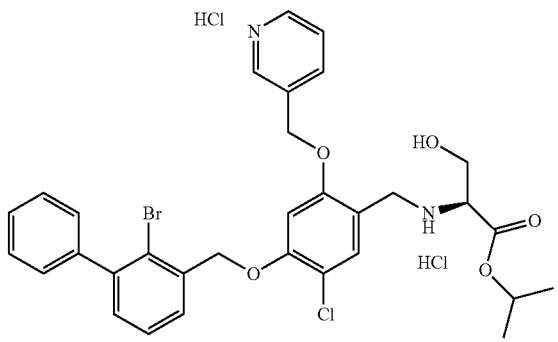 [SMILES: CC(C)OC(=O)[C@H](CO)NCc1cc(Cl)c(OCc2cccc(-c3ccccc3)c2Br)cc1OCc1cccnc1 ; Cl ; Cl]

(S)—N-(4-(2-bromo-3-phenylbenzyloxy)-5-chloro-2-(pyridin-3-yl-methyleneoxy) benzyl) serine (598 mg) and 60 ml of anhydrous isopropanol were placed in a 100 ml round-bottom flask. To the mixture were added 6 ml of dichlorosulfoxide and two drops of DMF with stirring in an ice water bath. And after the mixture was stirred at room temperature for 2 h it was heated to reflux until the reaction was completed. The mixture was concentrated under reduced pressure to remove the solvent and afford (S)-isopropyl N-(4-(2-bromo-3-phenylbenzyloxy)-5-chloro-2-(pyridin-3-yl-methyleneoxy)benzyl) serinate dihydrochloride as a white solid. $^1$H NMR (400 MHz, DMSO-$d_6$) δ 9.62 (s, 1H, —HCl), 9.40 (s, 1H, —HCl), 9.10 (s, 1H, —ArH), 8.86 (d, 1H, —ArH), 8.59 (d, J=7.6 Hz, 1H, —ArH), 8.01-7.91 (m, 1H, —ArH), 7.73-7.64 (m, 2H, —ArH), 7.57-7.46 (m, 3H, —ArH), 7.46-7.37 (m, 4H, —ArH), 7.16 (s, 1H, —ArH), 5.47 (s, 2H, —CH$_2$—), 5.36 (s, 2H, —CH$_2$—), 4.92 (m1H, —CH—), 4.30-4.15 (m, 2H, —CH$_2$—), 4.05 (s, 1H, —CH—), 3.97 (dd, J=12.0, 3.0 Hz, 1H, —CH$_2$—), 3.84 (dd, J=12.0, 3.8 Hz, 1H, —CH$_2$—), 1.20 (d, J=6.4 Hz, 3H, —CH$_3$), 1.18 (d, J=6.4 Hz, 3H, —CH$_3$). MS (FAB): 640 (M). $[α]^{27}_D$=−5.33 (C=0.075, methanol).

Example 7

(R)-Ethyl N-(4-(2-bromo-3-phenylbenzyloxy)-5-chloro-2-(pyridin-3-yl-methyleneoxy)benzyl) serinate

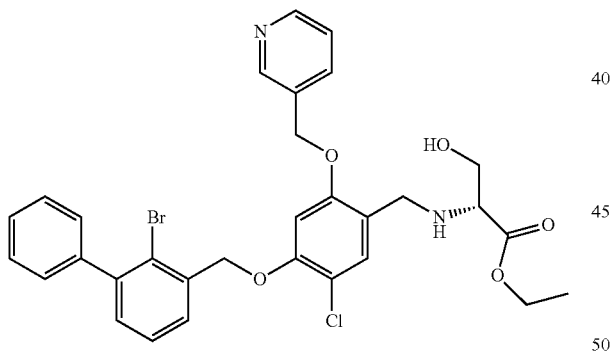

The procedure was the same as in Example 1, except that ethyl ester of D-serine was used in place of racemic ethyl ester of serine to afford (R)-ethyl N-(4-(2-bromo-3-phenylbenzyloxy)-5-chloro-2-(pyridin-3-yl-methyleneoxy)benzyl) serinate as a white solid. $^1$H NMR (400 MHz, DMSO-$d_6$) δ 8.68 (d, 1H, —ArH), 8.55 (dd, 1H, —ArH), 7.88 (d, 1H, —ArH), 7.65 (dd, J=7.6, 1.7 Hz, 1H, —ArH), 7.54-7.45 (m, 3H, —ArH), 7.45-7.35 (m, 6H, —ArH), 7.06 (s, 1H, —ArH), 5.30 (s, 2H, —CH$_2$—), 5.24 (s, 2H, —CH$_2$—), 4.81 (t, J=5.8 Hz, 1H, —CH—), 3.99 (q, J=7.1 Hz, 2H, —CH$_2$—), 3.74-3.57 (m, 2H, —CH$_2$—), 3.54 (t, 2H, —CH$_2$—), 1.12 (t, J=7.1 Hz, 3H, —CH$_3$). MS (FAB): 626 (M).

Example 8

(R)—N-(4-(2-bromo-3-phenylbenzyloxy)-5-chloro-2-(pyridin-3-yl-methyleneoxy) benzyl) serine

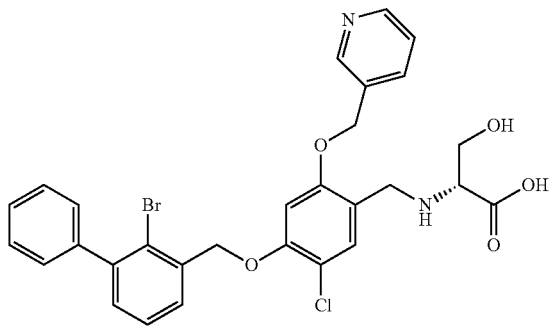 [SMILES: O=C(O)[C@@H](CO)NCc1cc(Cl)c(OCc2cccc(-c3ccccc3)c2Br)cc1OCc1cccnc1]

The procedure was the same as in Example 2, except that (R)-ethyl N-(4-(2-bromo-3-phenylbenzyloxy)-5-chloro-2-(pyridin-3-yl-methyleneoxy)benzyl) serinate was used in place of racemic ethyl N-(4-(2-bromo-3-phenylbenzyloxy)-5-chloro-2-(pyridin-3-yl-methyleneoxy)benzyl) serinate to afford (R)—N-(4-(2-bromo-3-phenylbenzyloxy)-5-chloro-2-(pyridin-3-yl-methyleneoxy) benzyl)serine as a white solid. $^1$H NMR (400 MHz, DMSO-$d_6$) δ 8.73 (s, 1H, —ArH), 8.55 (d, J=4.7 Hz, 1H, —ArH), 7.97 (d, J=7.9 Hz, 1H, —ArH), 7.65 (d, J=8.7 Hz, 1H, —ArH), 7.54-7.51 (m, 2H, —ArH), 7.47 (d, J=7.7 Hz, 2H, —ArH), 7.44 (d, J=1.7 Hz, 1H, —ArH), 7.42-7.40 (m, 2H, —ArH), 7.39-7.36 (m, 2H, —ArH), 7.11 (s, 1H, —ArH), 5.32 (s, 2H, —CH$_2$—), 5.28 (m, 2H, —CH$_2$—), 3.94 (s, 2H, —CH$_2$—), 3.69 (dd, J=11.1, 4.7 Hz, 1H, —CH$_2$—), 3.62 (dd, J=11.1, 6.2 Hz, 1H, —CH$_2$—), 3.16 (t, J=5.4 Hz, 1H, —CH—). MS (FAB): 599 (M+1). [α]

Example 9

(S)—N-(4-(2-chloro-3-phenylbenzyloxy)-5-chloro-2-(pyridin-3-yl-methyleneoxy) benzyl) serine

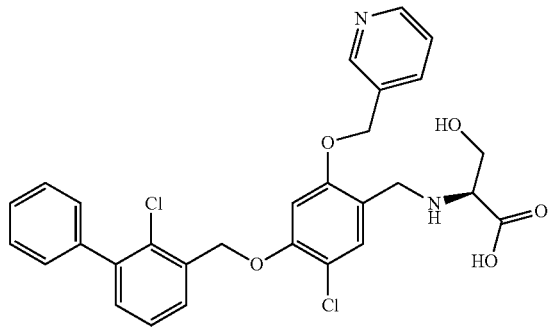 [SMILES: O=C(O)[C@H](CO)NCc1cc(Cl)c(OCc2cccc(-c3ccccc3)c2Cl)cc1OCc1cccnc1]

The procedure was the same as in Example 1, except that 4-(2-chloro-3-phenylbenzyloxy)-5-chloro-(pyridin-3-yl-methyleneoxy) benzaldehyde was used in place of 4-(2-bromo-3-phenylbenzyloxy)-5-chloro-2-(pyridin-3-yl-methyleneoxy) benzaldehyde, and ethyl ester of L-serine was used in place of racemic ethyl ester of serine to afford (S)-ethyl N-(4-(2-chloro-3-phenylbenzyloxy)-5-chloro-2-(pyridin-3-yl-methyleneoxy)benzyl)serinate.

The procedure was the same as in Example 2, except that (S)-ethyl N-(4-(2-chloro-3-phenylbenzyloxy)-5-chloro-2-(pyridin-3-yl-methyleneoxy)benzyl) serinate was used in place of ethyl N-(4-(2-bromo-3-phenylbenzyloxy)-5-chloro-2-(pyridin-3-yl-methyleneoxy)benzyl) serinate to afford (S)—N-(4-(2-chloro-3-phenylbenzyloxy)-5-chloro-2-(pyridin-3-yl-methyleneoxy) benzyl) serine as a white solid. $^1$H NMR (400 MHz, DMSO-d$_6$) δ 8.69 (s, 1H, —ArH), 8.51 (d, J=4.6 Hz, 1H, —ArH), 7.93 (d, J=7.6 Hz, 1H, —ArH), 7.63 (d, J=7.4 Hz, 1H, —ArH), 7.54-7.33 (m, 9H, —ArH), 7.12 (s, 1H, —ArH), 5.31 (s, 2H, —CH$_2$—), 5.25 (m, 2H, —CH$_2$—), 3.91 (s, 2H, —CH$_2$—), 3.66 (dd, J=11.0, 4.0 Hz, 1H, —CH$_2$—), 3.59 (dd, J=11.0, 6.0 Hz, 1H, —CH$_2$—), 3.14 (t, J=4.8 Hz, 1H, —CH—). MS (FAB): 554 (M+1).

Example 10

(S)—N-(4-(2-fluoro-3-phenylbenzyloxy)-5-chloro-2-(pyridin-3-yl-methyleneoxy) benzyl) serine

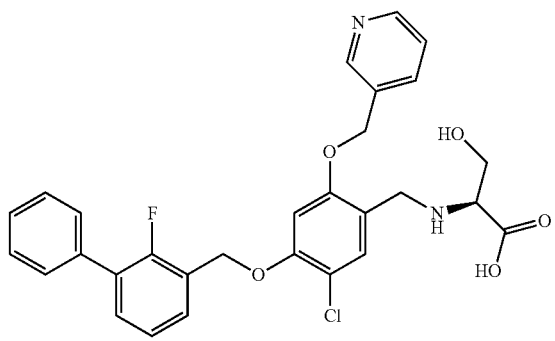 [SMILES: O=C(O)[C@H](CO)NCc1cc(Cl)c(OCc2cccc(-c3ccccc3)c2F)cc1OCc1cccnc1]

The procedure was the same as in Example 1, except that 4-(2-fluoro-3-phenylbenzyloxy)-5-chloro-2-(pyridin-3-yl-methyleneoxy) benzaldehyde was used in place of 4-(2-bromo-3-phenylbenzyloxy)-5-chloro-2-(pyridin-3-yl-methyleneoxy) benzaldehyde, and ethyl ester of L-serine was used in place of racemic ethyl ester of serine to afford (S)-ethyl N-(4-(2-fluoro-3-phenylbenzyloxy)-5-chloro-2-(pyridin-3-yl-methyleneoxy)benzyl) serinate.

The procedure was the same as in Example 2, except that (S)-ethyl N-(4-(2-fluoro-3-phenyl benzyloxy)-5-chloro-2-(pyridin-3-yl-methyleneoxy)benzyl) serinate was used in place of ethyl N-(4-(2-bromo-3-phenylbenzyloxy)-5-chloro-2-(pyridin-3-yl-methyleneoxy)benzyl) serinate to afford (S)—N-(4-(2-fluoro-3-phenylbenzyloxy)-5-chloro-2-(pyridin-3-yl-methyleneoxy) benzyl) serine as a white solid. $^1$H NMR (400 MHz, DMSO-d$_6$) δ 8.72 (dd, J=8.0, 1.9 Hz, 1H, —ArH), 8.56 (dd, J=4.8, 1.5 Hz, 1H, —ArH), 7.97 (d, J=7.9 Hz, 1H, —ArH), 7.72-7.30 (m, 10H, —ArH), 7.16 (d, J=15.1 Hz, 1H, —ArH), 5.35 (d, J=6.7 Hz, 2H, —CH$_2$—), 5.27 (dd, J=15.2, 3.2 Hz, 2H, —CH$_2$—), 3.95 (s, 2H, —CH$_2$—), 3.70 (dd, J=11.2, 4.5 Hz, 1H, —CH$_2$—), 3.63 (dd, J=11.2, 6.2 Hz, 1H, —CH$_2$—), 3.18 (t, J=5.3 Hz, 1H, —CH—). MS (FAB): 538 (M+1).

Example 11

(S)—N-(4-(3-phenylbenzyloxy)-5-chloro-2-(pyridin-3-yl-methyleneoxy)benzyl) serine

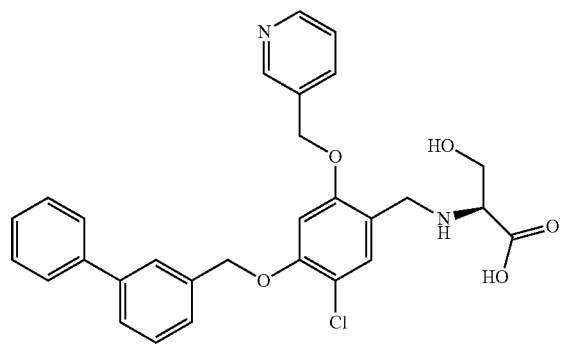 [SMILES: O=C(O)[C@H](CO)NCc1cc(Cl)c(OCc2cccc(-c3ccccc3)c2)cc1OCc1cccnc1]

The procedure was the same as in Example 1, except that 4-(3-phenylbenzyloxy)-5-chloro-2-(pyridin-3-yl-methyleneoxy)benzaldehyde was used in place of 4-(2-bromo-3-phenylbenzyl oxy)-5-chloro-2-(pyridin-3-yl-methyleneoxy) benzaldehyde, and ethyl ester of L-serine was used in place of racemic ethyl ester of serine to afford (S)-ethyl N-(4-(3-phenylbenzyloxy)-5-chloro-2-(pyridin-3-yl-methyleneoxy) benzyl) serinate.

The procedure was the same as in Example 2, except that (S)-ethyl N-(4-(3-phenylbenzyloxy)-5-chloro-2-(pyridin-3-yl-methyleneoxy)benzyl) serinate was used in place of ethyl N-(4-(2-bromo-3-phenylbenzyloxy)-5-chloro-2-(pyridin-3-yl-methyleneoxy)benzyl) serinate to afford (S)—N-(4-(3-phenylbenzyloxy)-5-chloro-2-(pyridin-3-yl-methyleneoxy) benzyl) serine as a white solid. $^1$H NMR (400 MHz, DMSO-d$_6$) δ 8.67 (s, 1H, Ar—H), 8.50 (s, 1H, Ar—H), 7.91 (d, J=5.6 Hz, 1H, Ar—H), 7.75 (s, 1H, Ar—H), 7.61 (d, J=13.2 Hz, 3H, Ar—H), 7.44 (d, J=15.2 Hz, 5H, Ar—H), 7.36 (d, J=8.4 Hz, 2H, Ar—H), 7.09 (s, 1H, Ar—H), 5.29 (s, 2H, —CH$_2$—), 5.19 (m, 2H, —CH$_2$—), 3.90 (s, 2H, —CH$_2$—), 3.69-3.55 (m, 2H, —CH$_2$—), 3.12 (m, 1H, —CH—). MS (FAB): 520 (M+1).

Example 12

N-(4-(2-bromo-3-phenylbenzyloxy)-5-chloro-2-(pyridin-3-yl-methyleneoxy)benzyl) glycine

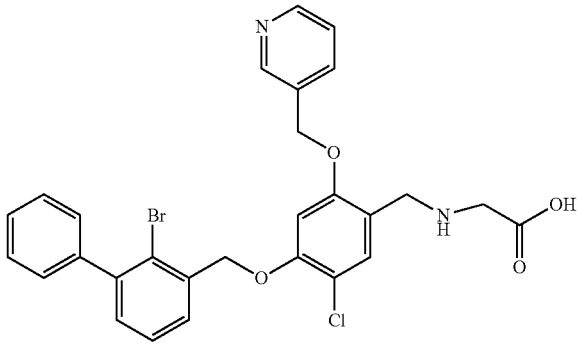 [SMILES: O=C(O)CNCc1cc(Cl)c(OCc2cccc(-c3ccccc3)c2Br)cc1OCc1cccnc1]

(1) 2-bromo-3-phenyltoluene

2-Bromo-3-iodotoluene (350 mg) was placed in 50 ml flask and dioxane/water was added with stirring. And the solution was bubbled with argon for 10 min to remove the dissolved oxygen. Then, phenylboronic acid (172.65 mg), cesium carbonate (961.2 mg) and triphenylphosphine palladium (40.91 mg) were added and the resulting mixture was stirred at 80-100° C. for 12 h under protection of argon. The reaction was stopped. After cooling to room temperature, the mixture was filtered with diatomaceous earth. The filtrate was concentrated under reduced pressure and extracted with water and ethyl acetate for three times. The organic phase was combined, washed with saturated brine and dried by anhydrous $Na_2SO_4$. The solution was filtered and evaporated under reduced pressure to dryness. The residue was purified by silica gel column chromatography (petroleum ether) to give colorless oil (221 mg). $^1$H NMR (400 MHz, DMSO-$d_6$), δ 7.49-7.29 (m, 7H, Ar—H), 7.14 (d, 1H, Ar—H), 2.42 (s, 3H, Ar—$CH_3$).

(2) 2-bromo-3-(bromomethyl)-1,1'-biphenyl

2-Bromo-3-phenyltoluene (234 mg) was weighed and placed in a 100 ml flask and 20 ml of $CCl_4$ was added. After 2-Bromo-3-phenyltoluene was completely dissolved, NBS (178 mg) was added under stirring. And the resulting mixture was heated to 80° C. to reflux. Then benzoyl peroxide (4 mg) was added and another 4 mg of benzoyl peroxide was added after 2 h, and the reaction was continued for another 2 h. The reaction was stopped. The reaction was cooled to room temperature and a suitable amount of water was added and the mixture was extracted with dichloromethane. The organic phase was washed with saturated brine and dried by anhydrous $Na_2SO_4$. The solution was filtered and evaporated under reduced pressure to dryness to give yellow oil (192 mg). The material was used for the next step without further purification.

(3) 2-hydroxy-4-(2-bromo-3-phenylbenzoxy)-5-chlorobenzaldehyde

To anhydrous acetonitrile (6 ml) in 50 ml flask was added 2,4-dihydroxy-5-chlorobenzaldehyde (73.94 mg) and sodium bicarbonate (98.88 mg). After stirring 40 min at room temperature, the solution of 2-bromo-3-(bromomethyl)-1,1'-biphenyl (192 mg) in 8 ml of DMF was slowly added dropwise to the reaction mixture via a constant pressure dropping funnel. The resulting mixture was refluxed until the reaction completed. After cooling to room temperature, the mixture was extracted with water and ethyl acetate. The organic phase was washed with saturated brine, dried over anhydrous sodium sulfate, filtered and evaporated under reduced pressure to dryness. The crude residue was purified by silica gel column chromatography to afford 2-hydroxy-4-(2-bromo-3-phenylbenzoxy)-5-chlorobenzaldehyde (152 mg) as a white solid. $^1$H NMR (500 MHz, DMSO-$d_6$) δ 11.18 (s, 1H, —OH), 10.09 (s, 1H, —CHO), 7.74 (s, 1H, —ArH), 7.66 (d, 1H, —ArH), 7.57 (t, 1H, —ArH), 7.51 (m, 2H, —ArH), 7.46 (d, 1H, —ArH), 7.42 (d, 3H, —ArH), 6.85 (s, 1H, —ArH), 5.37 (s, 2H, —$CH_2$—).

(4) 4-(2-bromo-3-phenylbenzoxy)-5-chloro-2-(pyridin-3-yl-methyleneoxy) benzaldehyde 2-Hydroxy-4-(2-bromo-3-phenylbenzoxy)-5-chlorobenzaldehyde (100 mg) was dissolved in 6 ml of DMF in a 50 ml flask, and then cesium carbonate (127.53 mg) was added. After stirring at room temperature for 15 min, a solution of 3-bromomethyleneoxy pyridine (76.65 mg) in DMF (4 ml) was added dropwise. After the mixture was stirred at 80° C. for 2 h, the reaction was stopped. After cooling to room temperature, the mixture was extracted with water and ethyl acetate. The organic phase was washed with saturated brine, and dried over anhydrous sodium sulfate, then filtrated and evaporated under reduced pressure to dryness. The crude residue was purified by silica gel column chromatography to afford a white solid (60 mg). $^1$H NMR (400 MHz, DMSO-$d_6$) δ 10.14 (s, 1H, —CHO), 8.71 (d, J=1.6 Hz, 1H, —ArH), 8.54 (d, J=4.8 Hz, 1H, —ArH), 7.94 (d, J=7.8 Hz, 1H, —ArH), 7.83 (s, 1H, —ArH), 7.66 (d, J=7.6 Hz, 1H, —ArH), 7.50 (t, J=7.6 Hz, 1H, —ArH), 7.48-7.32 (m, 7H, —ArH), 7.20 (s, 1H, —ArH), 5.42 (s, 2H, —$CH_2$—), 5.41 (s, 2H, —$CH_2$—).

(5)N-(4-(2-bromo-3-phenylbenzyloxy)-5-chloro-2-(pyridin-3-yl-methyleneoxy) benzyl) glycine 4-(2-bromo-3-phenylbenzoxy)-5-chloro-2-(pyridin-3-yl-methyleneoxy) benzaldehyde (80 mg) was dissolved in 5 ml of DMF, and then ethyl glycinate (49 mg, 0.472 mmol) and acetic acid glacial (57 mg) were added. After stirring at room temperature for 20 min, sodium cyanoborohydride (25 mg) was added and the mixture was stirred at 25° C. for 14 h. The reaction was stopped. The mixture was extracted with water and ethyl acetate. The organic phase was washed with saturated brine, and dried over anhydrous sodium sulfate, then filtrated and evaporated under reduced pressure to dryness. The residue was dissolved in ethanol, heated to reflux until the reaction was complete. The mixture was evaporated to dryness. The crude residue was purified by silica gel column chromatography to afford ethyl N-(4-(2-bromo-3-phenylbenzyloxy)-5-chloro-2-(pyridin-3-yl-methyleneoxy)benzyl) glycinate (70 mg) as yellow oil. The product was dissolved in methanol/$H_2O$ (4 ml/1 ml), and then lithium hydroxide monohydrate (20 mg) was added. After stirring at room temperature for 2 h, a few drops of acetic acid were added to the mixture in an ice bath to adjust the pH to acidity. The mixture was filtrated under reduced pressure to afford N-(4-(2-bromo-3-phenylbenzyloxy)-5-chloro-2-(pyridin-3-yl-methyleneoxy)benzyl) glycine (45 mg) as a white solid. $^1$H NMR (400 MHz, DMSO) δ 8.73 (d, J=1.7 Hz, 1H, —ArH), 8.55 (dd, J=4.8, 1.6 Hz, 1H, DMSO), 7.96 (dt, J=7.9, 1.9 Hz, 1H, DMSO), 7.65 (dd, J=7.6, 1.6 Hz, 1H, —ArH), 7.55-7.35 (m, 9H, —ArH), 7.12 (s, 1H, —ArH), 5.33 (s, 2H, —$CH_2$—), 5.29 (s, 2H, —$CH_2$—), 3.91 (s, 2H, —$CH_2$—), 3.11 (s, 2H, —$CH_2$—). MS (FAB): 569 (M+1).

Example 13

N-(4-(2-bromo-3-phenylbenzyloxy)-5-chloro-2-(pyridin-3-yl-methyleneoxy)benzyl) valine

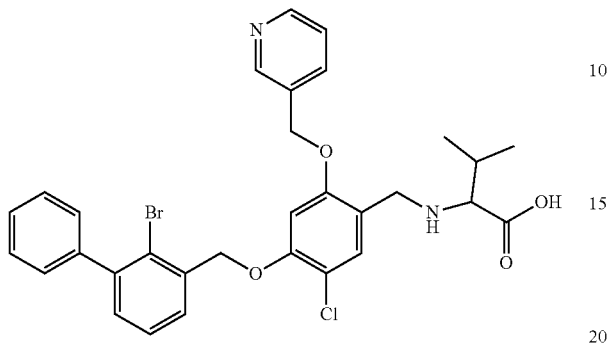

The procedure was the same as in Example 12, except that ethyl ester of valine was used in place of ethyl ester of glycine to afford N-(4-(2-bromo-3-phenylbenzyloxy)-5-chloro-2-(pyridin-3-yl-methyleneoxy)benzyl) valine as a white solid. $^1$H NMR (400 MHz, DMSO) δ 8.69 (s, 1H, —ArH), 8.56 (d, J=3.9 Hz, 1H, —ArH), 7.88 (d, J=7.8 Hz, 1H, —ArH), 7.66 (d, J=7.4 Hz, 1H, —ArH), 7.55-7.33 (m, 9H, —ArH), 7.06 (s, 1H, —ArH), 5.31 (s, 2H, —CH$_2$—), 5.22 (d, J=11.2 Hz, 2H, —CH$_2$—), 3.52 (s, 2H, —CH$_2$—), 2.91 (d, J=6.4 Hz, 1H, —CH—), 1.80 (dq, J=13.2, 6.5 Hz, 1H, —CH—), 0.86 (dd, J=18.9, 6.7 Hz, 6H, —CH$_3$). MS (FAB): 611 (M+1).

Example 14

(E)-3-(4-(2-bromo-3-phenylbenzyloxy)-5-chloro-2-(pyridin-3-yl-methyleneoxy) benzylamino) but-2-enenitrile

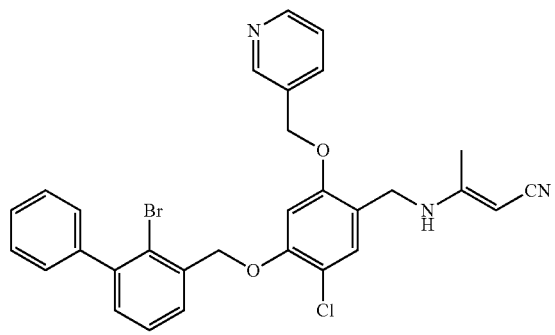 [SMILES: C/C(=C\C#N)NCc1cc(Cl)c(OCc2cccc(-c3ccccc3)c2Br)cc1OCc1cccnc1]

The procedure was the same as in Example 12, except that (E)-3-aminobut-2-enenitrile was used in place of ethyl ester of glycine without hydrolysis to afford (E)-3-(4-(2-bromo-3-phenylbenzyloxy)-5-chloro-2-(pyridin-3-yl-methyleneoxy) benzylamino) but-2-enenitrile as a white solid. $^1$H NMR (400 MHz) δ 8.70 (s, 1H, —ArH), 8.55 (d, J=4.2 Hz, 1H, —ArH), 7.99-7.81 (m, 1H, —ArH), 7.65 (d, J=7.0 Hz, 1H, —ArH), 7.58-7.31 (m, 9H, —ArH), 7.11 (d, J=33.8 Hz, 1H), 6.30 (s, 1H, =CH), 5.28 (d, J=14.1 Hz, 4H, —CH$_2$—), 3.27 (s, 2H, —CH$_2$—), 2.21-1.96 (m, 3H). MS (FAB): 576 (M+1).

Example 15

N,N-bis(2-hydroxyethyl)-4-(2-bromo-3-phenylbenzyloxy)-5-chloro-2-(pyridin-3-yl-methyleneoxy)benzylamine

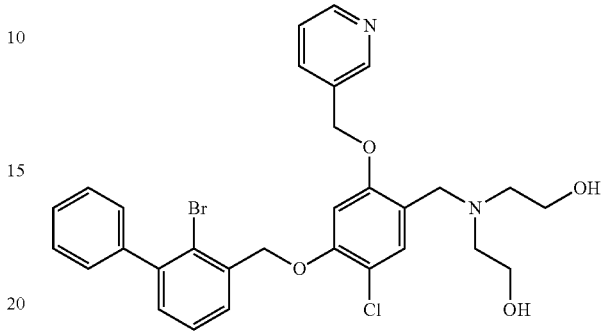

The procedure was the same as in Example 12, except that bis(2-hydroxyethyl)amine was used in place of ethyl ester of glycine without hydrolysis to afford N, N-bis(2-hydroxyethyl)-4-(2-bromo-3-phenylbenzyloxy)-5-chloro-2-(pyridin-3-yl-methyleneoxy)benzylamine as a white solid. $^1$H NMR (400 MHz, DMSO-d$_6$) δ 8.68 (s, 1H, ArH), 8.58-8.51 (m, 1H, ArH), 7.88 (d, J=7.2 Hz, 1H, ArH), 7.65 (d, J=7.6 Hz, 1H, ArH), 7.56-7.32 (m, 9H, ArH), 7.05 (d, J=2.4 Hz, 1H, ArH), 5.29 (s, 2H, —OCH$_2$—), 5.24 (s, 2H, —OCH$_2$—), 4.35 (s, 2H, —OH), 3.58 (s, 2H, —CH$_2$—), 3.41 (br s, 4H, —CH$_2$—), 2.51 (m, 4H, —CH$_2$—, overlapped in solvent peak). MS (FAB): 598 (M+1).

Example 16

N-(2-methanesulfonaminoethyl)-4-(2-bromo-3-phenylbenzyloxy)-5-chloro-2-(pyridin-3-yl-methyleneoxy)benzylamine

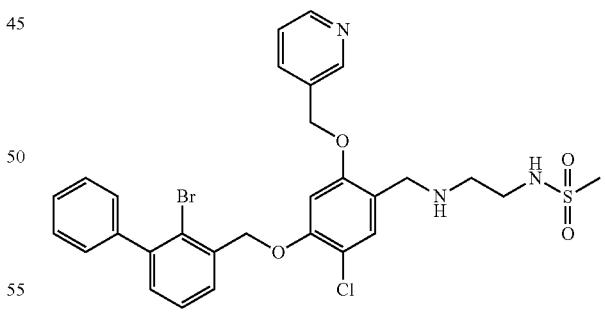

The procedure was the same as in Example 12, except that N-(2-aminoethyl)methanesulfonamide was used in place of ethyl ester of glycine without hydrolysis to afford N-(2-methanesulfonaminoethyl)-4-(2-bromo-3-phenylbenzyloxy)-5-chloro-2-(pyridin-3-yl-methyleneoxy)benzylamine as a white solid. $^1$H NMR (400 MHz, DMSO-d$_6$) δ 8.69 (s, 1H, ArH), 8.55 (d, J=4.4 Hz, 1H, ArH), 7.89 (d, J=7.6 Hz, 1H, ArH), 7.65 (d, J=8.0 Hz, 1H, ArH), 7.56-7.33 (m, 9H, ArH), 7.07 (s, 1H, ArH), 6.95 (s, 1H, —NH—), 5.30 (s, 2H, —OCH$_2$—), 5.25 (s, 2H, —OCH$_2$—), 3.64 (s, 2H, —CH$_2$—), 3.01 (m, 2H, —CH$_2$—), 2.88 (s, 3H, —CH$_3$), 2.59 (t, J=6.4 Hz, 2H, —CH$_2$—). MS (FAB): 631 (M).

Example 17

N-(2-acetylaminoethyl)-4-(2-bromo-3-phenylbenzyloxy)-5-chloro-2-(pyridin-3-yl-methyleneoxy) benzylamine

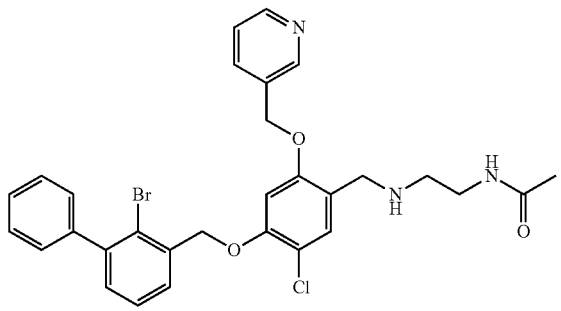 [SMILES: CC(=O)NCCNCc1cc(Cl)c(OCc2cccc(-c3ccccc3)c2Br)cc1OCc1cccnc1]

The procedure was the same as in Example 12, except that N-(2-aminoethyl)acetamide was used in place of ethyl ester of glycine without hydrolysis to afford N-(2-acetylaminoethyl)-4-(2-bromo-3-phenylbenzyloxy)-5-chloro-2-(pyridin-3-yl-methyleneoxy)benzylamine as a white solid. $^1$H NMR (400 MHz, DMSO-d$_6$) δ 8.69 (s, 1H, ArH), 8.55 (d, J=4.0 Hz, 1H, ArH), 7.88 (d, J=8.0 Hz, 1H, ArH), 7.80 (t, J=6.0 Hz, 1H, —NH—), 7.65 (d, J=6.0 Hz, 1H, ArH), 7.57-7.35 (m, 9H, ArH), 7.07 (s, 1H, ArH), 5.30 (s, 2H, —OCH$_2$—), 5.25 (s, 2H, —OCH$_2$—), 3.65 (s, 2H, —CH$_2$—), 3.12 (q, J=6.0 Hz, 2H, —CH$_2$—), 2.54 (t, J=6.4 Hz, 2H, —CH$_2$—), 1.78 (s, 3H). MS (FAB): 595 (M).

Example 18

(E)-3-(4-(2-bromo-3-phenylbenzyloxy)-5-chloro-2-(pyridin-3-yl-methyleneoxy) benzylamino) but-2-enoic acid

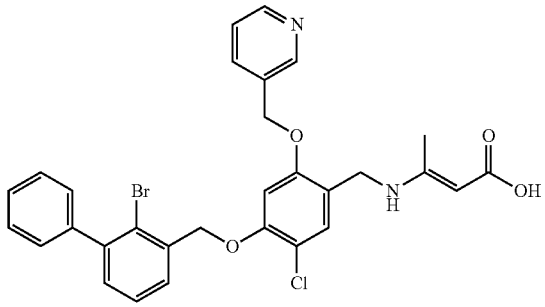 [SMILES: C/C(=C\C(=O)O)NCc1cc(Cl)c(OCc2cccc(-c3ccccc3)c2Br)cc1OCc1cccnc1]

The procedure was the same as in Example 12, except that (E)-3-aminobut-2-enoic acid was used in place of ethyl ester of glycine without hydrolysis to afford (E)-3-(4-(2-bromo-3-phenylbenzyloxy)-5-chloro-2-(pyridin-3-yl-methyleneoxy)benzylamino) but-2-enoic acid as a white solid. $^1$H NMR (400 MHz, DMSO-d$_6$) δ 8.74 (s, 1H, ArH), 8.55 (d, J=4.4 Hz, 1H, ArH), 7.98 (d, J=8.0 Hz, 1H, ArH), 7.65 (dd, J$_1$=7.6 Hz, J$_2$=1.2 Hz, 1H, ArH), 7.55-7.34 (m, 9H, ArH), 7.13 (s, 1H, ArH), 5.33 (s, 2H, —OCH$_2$—), 5.29 (s, 2H, —OCH$_2$—), 3.85 (dd, J$_1$=52.4 Hz, J$_2$=13.2 Hz, 2H), 3.05 (s, 1H, =CH), 1.12 (d, J=6.4 Hz, 3H). MS (FAB): 594 (M+1).

Example 19

2-(4-(2-bromo-3-phenylbenzyloxy)-5-chloro-2-(pyridin-3-yl-methyleneoxy) benzylamino)ethanesulfonic acid

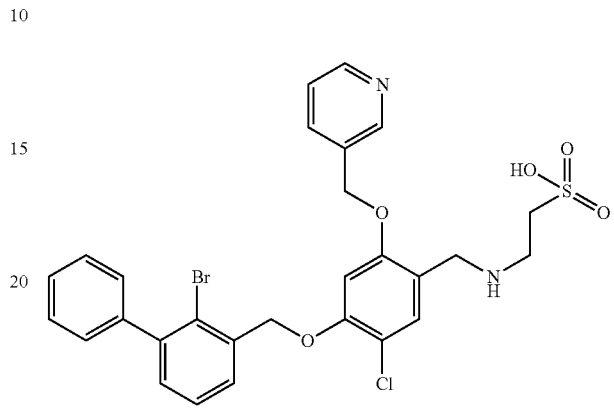

The procedure was the same as in Example 12, except that 2-aminoethanesulfonic acid was used in place of ethyl ester of glycine without hydrolysis to afford 2-(4-(2-bromo-3-phenylbenzyloxy)-5-chloro-2-(pyridin-3-yl-methyleneoxy) benzylamino)ethanesulfonic acid as a white solid. $^1$H NMR (400 MHz, DMSO) δ 8.79 (s, 1H), 8.62 (d, J=4.8 Hz, 1H), 8.42 (d, J=7.2 Hz, 1H), 7.85 (t, J=4.8 Hz, 1H), 7.43 (m, 9H), 7.04 (s, 1H), 5.37 (s, 2H), 5.24 (s, 2H), 4.33 (s, 2H), 3.39 (m, 2H), 2.97 (m, 2H), 2.65 (br, 1H). MS (FAB): 618 (M+1).

Example 20

N-(4-(2-bromo-3-phenylbenzyloxy)-5-chloro-2-(pyridin-3-yl-methyleneoxy)benzyl) leucine

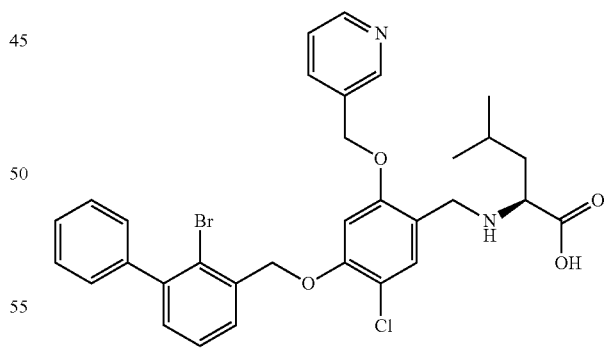

The procedure was the same as in Example 12, except that ethyl ester of leucine was used in place of ethyl ester of glycine to afford N-(4-(2-bromo-3-phenylbenzyloxy)-5-chloro-2-(pyridin-3-yl-methyleneoxy)benzyl) leucine as a white solid. $^1$H NMR (400 MHz, DMSO) δ 8.69 (s, 1H), 8.52 (d, J=4.8 Hz, 1H), 8.42 (d, J=7.2 Hz, 1H), 7.85 (t, J=4.8 Hz, 1H), 7.43 (m, 9H), 7.04 (s, 1H), 5.37 (s, 2H), 5.24 (s, 2H), 3.79 (m, 2H), 3.18 (m, 1H), 1.86 (m, 1H), 1.41 (m, 2H), 0.74 (m, 6H). MS (FAB): 624 (M).

Example 21

N-(4-(2-bromo-3-phenylbenzyloxy)-5-chloro-2-(pyridin-3-yl-methyleneoxy)benzyl) tyrosine

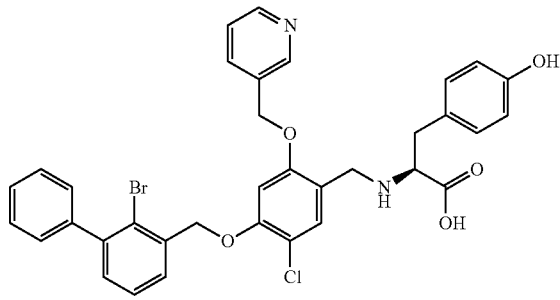 [SMILES: O=C(O)[C@H](Cc1ccc(O)cc1)NCc1cc(Cl)c(OCc2cccc(-c3ccccc3)c2Br)cc1OCc1cccnc1]

The procedure was the same as in Example 12, except that ethyl ester of tyrosine was used in place of ethyl ester of glycine to afford N-(4-(2-bromo-3-phenylbenzyloxy)-5-chloro-2-(pyridin-3-yl-methyleneoxy)benzyl) tyrosine as a white solid. $^1$H NMR (400 MHz, DMSO) δ 8.62 (s, 1H), 8.50 (d, J=3.2 Hz, 1H), 7.81 (t, J=7.6 Hz, 1H), 7.60 (t, J=9.2 Hz, 1H), 7.38 (m, 8H), 7.21 (s, 1H), 7.00 (s, 1H), 6.93 (d, J=8.0 Hz, 2H), 6.59 (d, J=8.0 Hz, 2H), 5.25 (s, 2H), 5.17 (s, 2H), 3.64 (m, 2H), 3.21 (t, J=6.8 Hz, 1H), 2.78 (m, 2H). MS (FAB): 674 (M).

Example 22

N-(4-(2-bromo-3-phenylbenzyloxy)-5-chloro-2-(pyridin-3-yl-methyleneoxy)benzyl) isoleucine

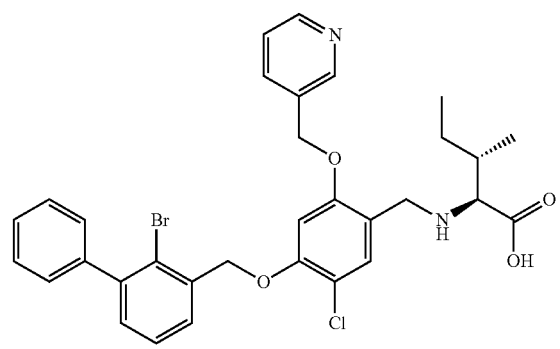 [SMILES: CC[C@H](C)[C@H](NCc1cc(Cl)c(OCc2cccc(-c3ccccc3)c2Br)cc1OCc1cccnc1)C(=O)O]

The procedure was the same as in Example 12, except that ethyl ester of isoleucine was used in place of ethyl ester of glycine to afford N-(4-(2-bromo-3-phenylbenzyloxy)-5-chloro-2-(pyridin-3-yl-methyleneoxy)benzyl) isoleucine as a white solid. $^1$H NMR (400 MHz, DMSO) δ 8.64 (s, 1H), 8.50 (d, J=4.8 Hz, 1H), 8.38 (d, J=7.2 Hz, 1H), 7.82 (t, J=4.8 Hz, 1H), 7.43 (m, 9H), 7.00 (s, 1H), 5.25 (s, 2H), 5.18 (s, 2H), 3.63 (m, 2H), 3.48 (m, 1H), 2.28 (m, 1H), 1.50 (m, 2H), 1.06 (m, 3H), 0.73 (m, 3H). MS (FAB): 624 (M).

Example 23

N-(4-(2-bromo-3-phenylbenzyloxy)-5-chloro-2-(pyridin-3-yl-methyleneoxy)benzyl) asparagine

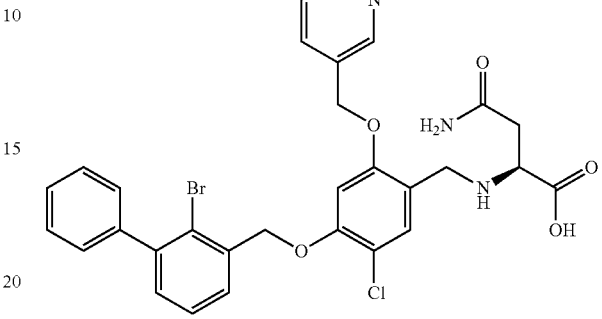

The procedure was the same as in Example 12, except that ethyl ester of asparagine was used in place of ethyl ester of glycine to afford N-(4-(2-bromo-3-phenylbenzyloxy)-5-chloro-2-(pyridin-3-yl-methyleneoxy)benzyl) asparagine as a white solid. $^1$H NMR (400 MHz, DMSO) δ11.96 (s, 1H), 8.72 (s, 1H), 8.52 (d, J=8.0 Hz, 1H), 8.16 (s, 1H), 7.68 (t, J=8.0 Hz, 1H), 7.44 (m, 10H), 7.01 (m, 2H), 5.26 (s, 2H), 5.21 (s, 2H), 3.65 (m, 2H), 3.35 (m, 1H), 2.65 (m, 2H). MS (FAB): 625 (M+1).

Example 24

N-(hydroxyethyl)-4-(2-bromo-3-phenylbenzyloxy)-5-chloro-2-(pyridin-3-yl-methyleneoxy)benzylamine

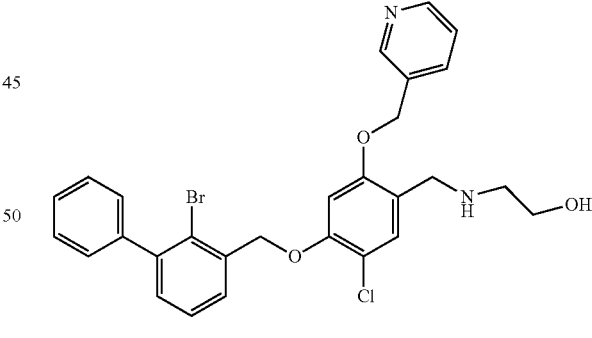

The procedure was the same as in Example 12, except that 2-aminoethan-1-ol was used in place of ethyl ester of glycine without hydrolysis to afford N-(hydroxyethyl)-4-(2-bromo-3-phenylbenzyloxy)-5-chloro-2-(pyridin-3-yl-methyleneoxy)benzylamine as a white solid. $^1$H NMR (400 MHz, DMSO-d$_6$) δ 8.70 (s, 1H, Ar—H), 8.54 (d, J=15.4 Hz, 1H, Ar—H), 7.92 (s, 1H, Ar—H), 7.72-7.25 (m, 10H), 7.11 (s, 1H, Ar—H), 5.30 (s, 2H, —CH$_2$—), 5.28 (s, 2H, —CH$_2$—), 3.89 (m, 2H, —CH$_2$—), 3.54 (s, 2H, —CH$_2$—), 2.76 (s, 2H, —CH$_2$—). MS (FAB): 554 (M+1).

Example 25

N-(4-(2-bromo-3-phenylbenzyloxy)-5-chloro-2-(pyridin-3-yl-methyleneoxy)benzyl) alanine

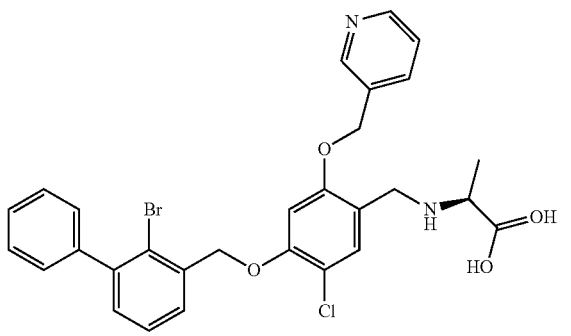 [SMILES: C[C@H](NCc1cc(Cl)c(OCc2cccc(-c3ccccc3)c2Br)cc1OCc1cccnc1)C(=O)O]

The procedure was the same as in Example 12, except that ethyl ester of alanine was used in place of ethyl ester of glycine to afford N-(4-(2-bromo-3-phenylbenzyloxy)-5-chloro-2-(pyridin-3-yl-methyleneoxy)benzyl) alanine as a white solid. $^1$H NMR (400 MHz, DMSO-d$_6$) δ 8.69 (s, 1H, Ar—H), 8.53 (m, 1H, Ar—H), 7.93 (d, J=8.0 Hz, 1H, Ar—H), 7.61 (d, J=8.1 Hz, 1H, Ar—H), 7.53-7.31 (m, 9H, Ar—H), 7.08 (s, 1H, Ar—H), 5.29 (s, 2H, —CH$_2$—), 5.27-5.23 (m, 2H, —CH$_2$—), 3.96-3.77 (m, 2H, —CH$_2$—), 3.12 (m, 1H, —CH—), 1.19 (d, J=7.0 Hz, 3H, —CH$_3$). MS (FAB): 582 (M+1).

Example 26

N-(4-(2-bromo-3-phenylbenzyloxy)-5-chloro-2-(pyridin-3-yl-methyleneoxy)benzyl) proline

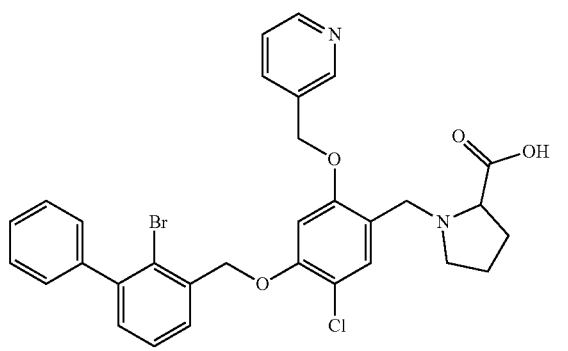 [SMILES: O=C(O)C1CCCN1Cc1cc(Cl)c(OCc2cccc(-c3ccccc3)c2Br)cc1OCc1cccnc1]

The procedure was the same as in Example 12, except that ethyl ester of proline was used in place of ethyl ester of glycine to afford N-(4-(2-bromo-3-phenylbenzyloxy)-5-chloro-2-(pyridin-3-yl-methyleneoxy)benzyl) proline as a white solid. $^1$H NMR (400 MHz, DMSO-d$_6$) δ 8.72 (s, 1H, ArH), 8.56 (d, J=6.0 Hz, 1H, ArH), 7.95 (d, J=8.0 Hz, 1H, ArH), 7.66 (d, J=7.6 Hz, 1H, ArH), 7.5-7.34 (m, 9H, ArH), 7.12 (s, 1H, ArH), 5.35-5.27 (m, 4H, —OCH$_2$—), 3.95 (dd, J$_1$=51.6 Hz, J$_2$=13.2 Hz, 2H, —CH$_2$—), 3.12 (m, 1H, —CH—), 2.67 (m, 1H, —CH$_2$—), 2.07 (m, 1H, —CH$_2$—), 1.89 (m, 1H, —CH$_2$—), 1.78 (m, 1H, —CH$_2$—), 1.68 (m, 1H, —CH$_2$—), 0.84 (m, 1H, —CH$_2$—). MS (FAB): 608 (M).

Example 27

(S)-Sodium N-(4-(2-bromo-3-phenylbenzyloxy)-5-chloro-2-(pyridin-3-yl-methyleneoxy) benzyl) serinate

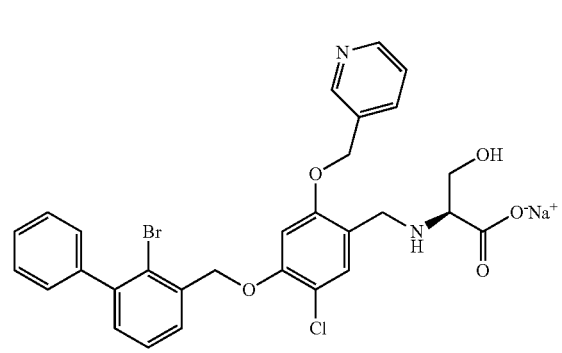

(S)—N-(4-(2-bromo-3-phenylbenzyloxy)-5-chloro-2-(pyridin-3-yl-methyleneoxy) benzyl) serine (299 mg) was dissolved in 1 ml of 0.5 N sodium hydroxide aqueous solution. After being stirred for 30 min at room temperature, absolute ethanol was added to the solution until solids appeared. After being heated to dissolve and cooled to room temperature, the mixture was placed in the refrigerator for freezing. Then the mixture was filtered to afford the product (300 mg) as a white solid. $^1$H NMR (400 MHz, Methanol-d$_4$) δ 8.65 (s, 1H, —ArH), 8.49 (d, 1H, —ArH), 8.04 (d, 1H, —ArH), 7.63 (d, J=8.0 Hz, 1H, —ArH), 7.50-7.34 (m, 8H, —ArH), 7.31 (d, J=7.5 Hz, 1H, —ArH), 6.84 (s, 1H, —ArH), 5.28 (s, 2H, —CH$_2$—), 5.23 (s, 2H, —CH$_2$—), 3.85-3.74 (m, 2H, —CH$_2$—), 3.72 (d, J=4.6 Hz, 1H, —CH$_2$—), 3.67 (m, 1H, —CH$_2$—), 3.15 (t, J=5.6 Hz, 1H, —CH—). MS (FAB): 599 (M+1).

Example 28

(S)-Calcium N-(4-(2-bromo-3-phenylbenzyloxy)-5-chloro-2-(pyridin-3-yl-methyleneoxy) benzyl) serinate

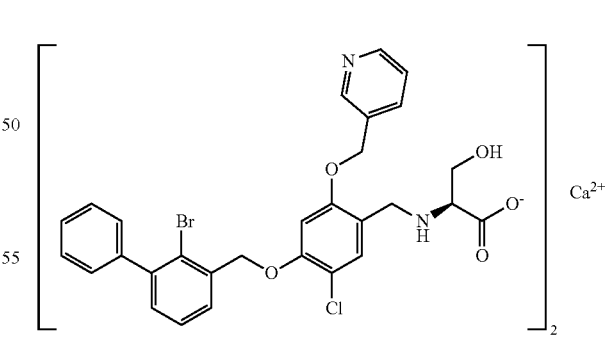

(S)-Sodium N-(4-(2-bromo-3-phenylbenzyloxy)-5-chloro-2-(pyridin-3-yl-methyleneoxy)benzyl) serinate (243 mg) was dissolved in 5 ml of water. Aqueous solution of calcium dichloride (1%, 2.22 ml) was added dropwise while being stirred at room temperature. Then the mixture was stirred overnight, filtered, washed with water, and dried to afford the product (240 mg) as a white solid. MS (FAB): 599 (M+1).

Example 29

(S)-(5-methyl-2-oxo-1,3-dioxol-4-yl)methyl N-(4-(2-bromo-3-phenylbenzyloxy)-5-chloro-2-(pyridin-3-yl-methyleneoxy)benzyl) serinate

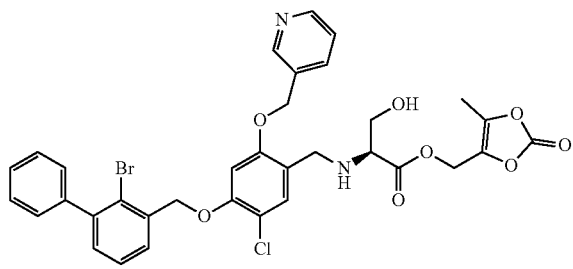 [SMILES: Cc1oc(=O)oc1COC(=O)[C@H](CO)NCc1cc(Cl)c(OCc2cccc(-c3ccccc3)c2Br)cc1OCc1cccnc1]

(S)—N-(4-(2-bromo-3-phenylbenzyloxy)-5-chloro-2-(pyridin-3-yl-methyleneoxy) benzyl) serine (299 mg) and 4-(chloromethyl)-5-methyl-1,3-dioxol-2-one (74 mg) were dissolved in 10 ml of DMF. After a catalytic amount of potassium iodide was added, the mixture was stirred at 30° C. until the reaction was completed. The mixture was poured into a stirred ice-cold saturated aqueous solution of sodium bicarbonate, then filtered, and the solid was washed with water and dried to afford the product (98 mg). MS (FAB): 711 (M+1).

Pharmacological Experiments

1. In vitro activity evaluation: Cisbio PD-1/PD-L1 binding assay kit was applied for the detection method of in vitro enzymology level.

Screening Principles and Methods of PD-1/PD-L1 Small Molecule Inhibitors

1) Principle: PD-1 protein is with HIS tag, and PD-1 ligand PD-L1 is with hFc tag. Eu labeled anti-hFc antibody and XL665 labeled anti-HIS antibody are combined with the above two label proteins respectively. After laser excitation, energy can be transferred from donor Eu to receptor XL665, allowing XL665 to glow. After adding inhibitors (compounds or antibodies), blocking the binding of PD-1 and PD-L1 makes the distance between Eu and XL665 far away, the energy can not be transferred, and XL665 does not glow.

2) Experimental method: The specific method can be referred to Cisbio's PD-1/PD-L1 Kit (item 64CUS000C-2). Reagents should be dispensed in the following order. For 384-well white ELISA plate, 2 µl of diluent or target compound diluted with diluent was added to each well, and then 4 µl of PD-1 protein and 4 µl of PD-L1 protein were added per well, incubated for 15 min at room temperature; and 10 µl of a mixture of anti-Tag1-Eu$^{3+}$ and anti-Tag2-XL665 was added per well and incubated for 1 h to 4 h at room temperature and the fluorescence signals at 665 nm and 620 nm were measured with an Envison instrument. HTRF rate=(665 nm/620 nm)*$10^4$. 8-10 concentrations were detected for each compound and $IC_{50}$ was calculated by Graphpad software.

3) The results of the screening were shown in Table 1.

TABLE 1

Evaluation of the inhibitory activity of the example compounds at molecular level on the interaction between PD-1 and PD-L1:

| Example | $IC_{50}$ (M) |
|---|---|
| 1 | $1.48 \times 10^{-7}$ |
| 4 | $<10^{-13}$ |
| 6 | $8.23 \times 10^{-8}$ |
| 8 | $4.29 \times 10^{-8}$ |
| 9 | $4.01 \times 10^{-8}$ |
| 10 | $1.34 \times 10^{-7}$ |
| 11 | $3.18 \times 10^{-7}$ |
| 12 | $4.11 \times 10^{-8}$ |
| 13 | $2.00 \times 10^{-7}$ |
| 14 | $2.69 \times 10^{-5}$ |
| 15 | $5.10 \times 10^{-8}$ |
| 16 | $1.99 \times 10^{-7}$ |
| 17 | $5.51 \times 10^{-7}$ |
| 18 | $2.33 \times 10^{-9}$ |
| 19 | $1.62 \times 10^{-5}$ |
| 20 | $6.10 \times 10^{-8}$ |
| 21 | $4.06 \times 10^{-7}$ |
| 22 | $4.99 \times 10^{-6}$ |
| 23 | $8.35 \times 10^{-7}$ |
| 24 | $5.38 \times 10^{-8}$ |
| 25 | $5.29 \times 10^{-9}$ |
| 26 | $10^{-12} \sim 10^{-13}$ |

Cisbio HTRF detection showed that the interaction of PD-1 and PD-L1 could be significantly inhibited by the Example 4 compound at the molecular level, with $IC_{50} < 10^{-13}$ mol/L.

2. The Example 4 Compound's Capacity of Relieving the Inhibition of IFNγ by Ligand PD-L1:

The expression level of IFNγ can reflect the proliferative activity of T lymphocytes. Using the extracted human PBMC (peripheral blood mononuclear cell), on the basis that T lymphocyte could be activated by the anti-CD3/anti-CD28 antibody, the ligand PD-L1 was added to the inhibit T lymphocyte, the example compounds' capacity of relieving the inhibition by the PD-L1 was investigated.

The specific procedure is as follows. DAKEWE human lymphocyte separation solution (DKW-KLSH-0100) was used to extract PBMC from human whole blood, and PBMC was inoculated into 96 well plate, with $3 \times 10^5$ cells per well. Human PD-L1 protein (final concentration 5 µg/ml), anti-CD3/anti-CD28 antibody (final concentration 1 µg/ml) and proportional dilution of the Example 4 compound were added respectively. After 72 h, the expression level of IFNγ in the supernatant was detected by Cisbio IFNγ test kit. The experimental results showed that the inhibition of PD-L1 to expression level of IFNγ could be partially relieved by the Example 4 compound (YPD29B) at 10 nM, and the level of $IC_{50}$ was determined as the level of $1.8 \times 10^{-10}$ mol/L by testing different concentrations (FIG. 1).

3. The Efficacy of the Example 4 Compound In Vivo

The methods of pharmacodynamics were as follows:

The method in subcutaneous xenograft tumor was as follows. The cultured specific tumor cells were digested and collected by centrifugation, and washed with sterile physiological saline for two times and then counted. The cell concentration was adjusted to $5 \times 10^6$/ml by physiological saline, and 0.2 ml of cell suspension was inoculated to the right armpit of C57BL/6 or Bablc mice. After inoculation, the animals were randomly divided into two groups in next day. Each group had 6-7 mice. After weighing, the animals were dosed once each day to monitor tumor size. When the tumor size reached to a certain size, the mice was weighed and blood was collected from mice orbit and then the mice were killed by removing the neck. The tumor tissue, thymus tissue and spleen tissue were collected and weighed respectively. Finally, the tumor growth inhibition rate was calculated, and the tumor growth inhibition rate was used to evaluate the level of anti-tumor effect.

The method in B16F10 lung metastasis model was as follows. The cultured B16F10 tumor cells were digested and centrifuged and washed for two times with sterile physiological saline and then counted. And the cell concentration was adjusted to $2.5 \times 10^6$/ml by physiological saline. 0.2 ml of cells were injected into the C57BL/6 mice through the tail vein, and the tumor cells will gather in the lung of the mice. After inoculation, the animals were randomly divided into two groups in next day. Each group had 6-7 mice. After weighing, the animals were dosed once each day. After 3 weeks, the mice were weighed and killed, the lung tissue was collected and weighed, and the number of lung tumors was counted after being fixed by the Bouin's Fluid. Finally, the tumor growth inhibition rate was calculated, and the tumor growth inhibition rate was used to evaluate the level of anti-tumor effect.

The method in Lewis lung cancer hydrothorax model was as follows: The subcutaneous xenograft tumor of Lewis lung cancer was homogenized and washed for two times with sterile physiological saline, and the cell concentration was adjusted to $2.5 \times 10^5$/ml by physiological saline. 0.2 ml of cells were injected into the thoracic cavity of C57BL/6 mice. After inoculation, the animals were randomly divided into two groups in next day. Each group had 6-7 mice. After weighing, the animals were dosed once each day. Animals were sacrificed when the weight of the animals in the control group suddenly dropped. The liquid in thoracic cavity was extracted with syringe and the volume of fluid was recorded.

In the study of the mechanism of the above models, the method of flow cytometry was adopted in measuring the total cell proportion of T cells of various types. The specific steps were as follows. The samples were treated at first. For blood tissue, the orbital blood was taken. The red cell lysate was used to remove the red blood cells, and then the PBS buffer was used for wash. After being washed, the cells were collected. For the tumor and spleen, the tissues were grinded with a homogenizer, and then diluted with PBS buffer, then filtered by 300 meshes of screen. After the number of cells was counted for each sample, $1 \times 10^6$ cells were added into EP tube and stained for flow antibody. After incubation for 1 h on ice, each sample was washed 2 times with PBS buffer. The cell population was analyzed by VERSE flow instrument of BD Company. The total number of cells in tumor tissue was $1 \times 10^5$ and the total number of cells in blood and spleen tissues was $1 \times 10^4$. The ratio of T cells to total number of cells was analyzed after flow cytometry.

(1) Subcutaneous Xenograft Model of High Metastatic Melanoma B16F10

Figure 2:
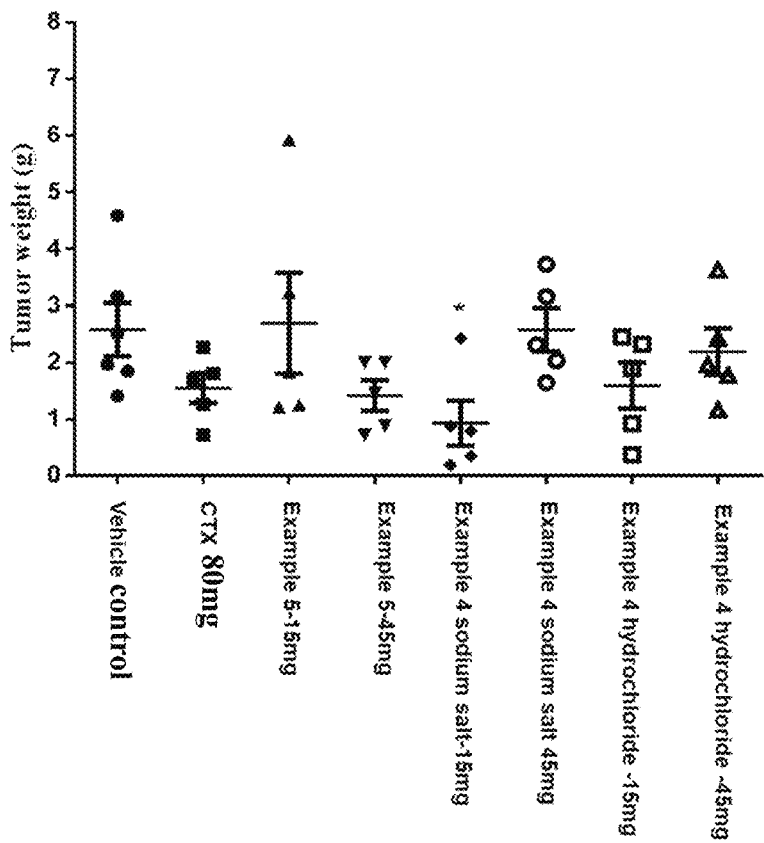
FIG. 2 illustrates the inhibitory effect of Example 5 compound, hydrochloride form of Example 4 compound and sodium salt of Example 4 compound on tumor weight of the high metastatic melanoma B16F10.
Figure 3:
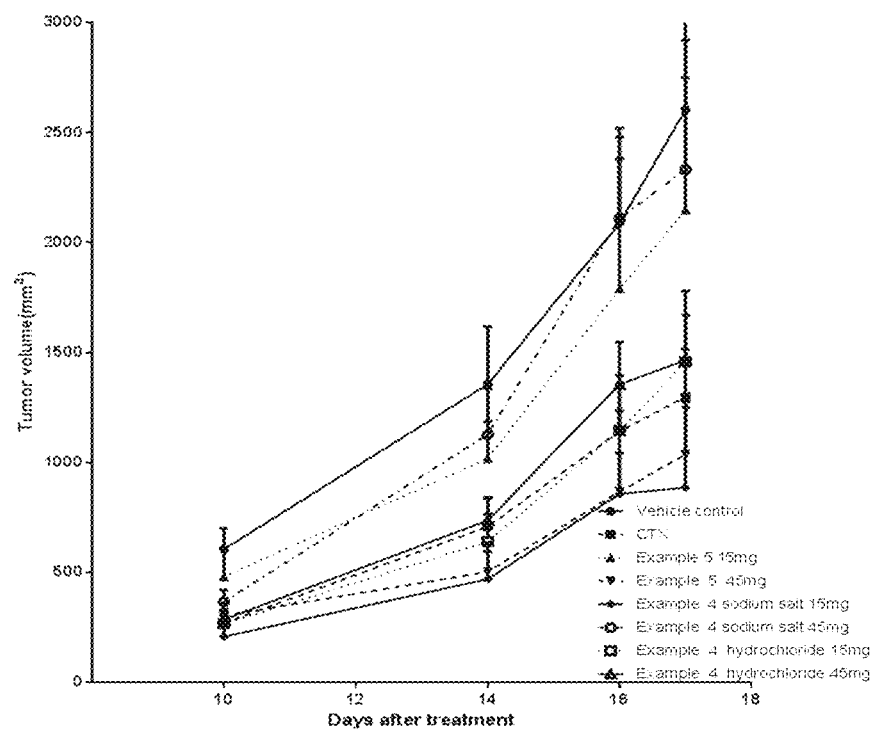
FIG. 3 illustrates the inhibitory effect of Example 5 compound, hydrochloride form of Example 4 compound and sodium salt of Example 4 compound on tumor volume of the high metastatic melanoma B16F10.

For the high metastatic melanoma B16F10, the example compounds (45 mg/kg of Example 5 compound, 15 mg/kg of hydrochloride form of Example 4 compound and 15 mg/kg of sodium salt of Example 4 compound) can significantly inhibit the growth of the subcutaneous tumor, with the respect of tumor volume or weight (FIG. 2, FIG. 3 and Table 2) and the rate of inhibition of tumor weight can be 45.27%, 38.37% and 64.11% respectively.

TABLE 2

Inhibition of Bl6F10 subcutaneous xenograft tumors by Example compounds

| Group | Dose | Number (Begin/End) | Body weight (g) Mean ± SD Begin | End | Tumor weight(g) X ± SD | T/C % (TGI %) |
|---|---|---|---|---|---|---|
| Vehicle Control | | 6/6 | 20.3 ± 1.0 | 23.7 ± 1.7 | 2.58 ± 1.56 | NA |
| Cyclophosphamide (CTX) | 80 mg/kg | 5/5 | 20.3 ± 0.8 | 23.3 ± 1.4 | 1.55 ± 0.59 | 60.00(40.00) |
| Example 5 | 15 mg/kg | 5/5 | 20.4 ± 1.0 | 24.2 ± 2.2 | 2.69 ± 1.99 | 104.26(−4.26) |
| | 45 mg/kg | 5/5 | 20.3 ± 1.0 | 22.6 ± 1.4 | 1.41 ± 0.60 | 54.73(45.27) |
| Example 4 sodium salt | 15 mg/kg | 5/5 | 20.3 ± 0.4 | 21.8 ± 2.1 | 0.93 ± 0.89 | 35.89(64.11)* |
| | 45 mg/kg | 5/5 | 20.4 ± 0.9 | 23.8 ± 1.4 | 2.57 ± 0.85 | 99.77(0.23) |
| Example 4 hydrochloride form | 15 mg/kg | 5/5 | 20.3 ± 0.6 | 22.6 ± 1.4 | 1.59 ± 0.91 | 61.63(38.37) |
| | 45 mg/kg | 5/5 | 20.3 ± 0.7 | 23.1 ± 1.7 | 2.19 ± 0.92 | 84.81(15.19) |

Figure 4:
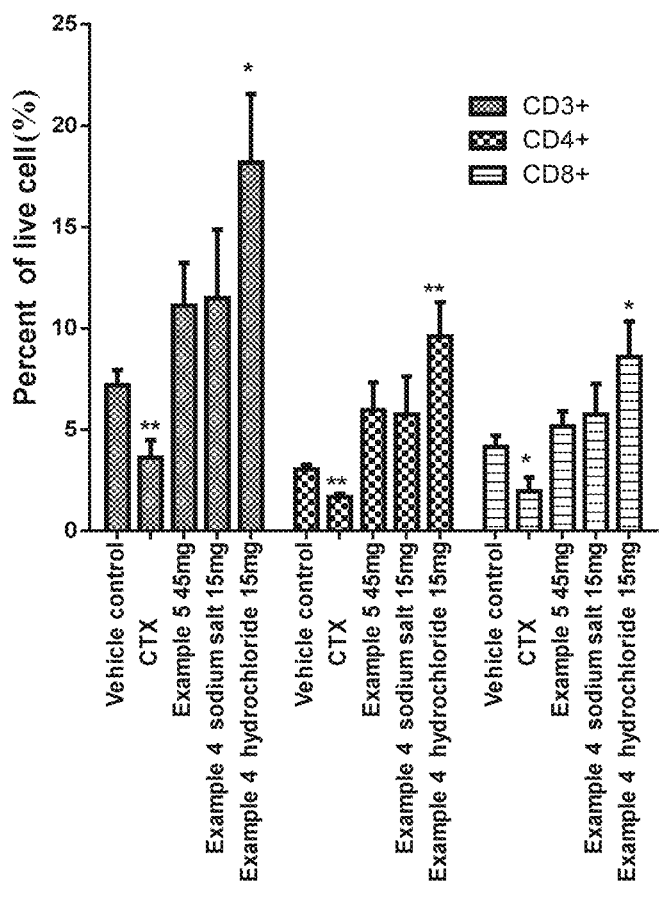
FIG. 4 illustrates the effect of Example 5 compound, hydrochloride form of Example 4 compound and sodium salt of Example 4 compound on the proportion of tumor-infiltrating lymphocytes.
Figure 5:
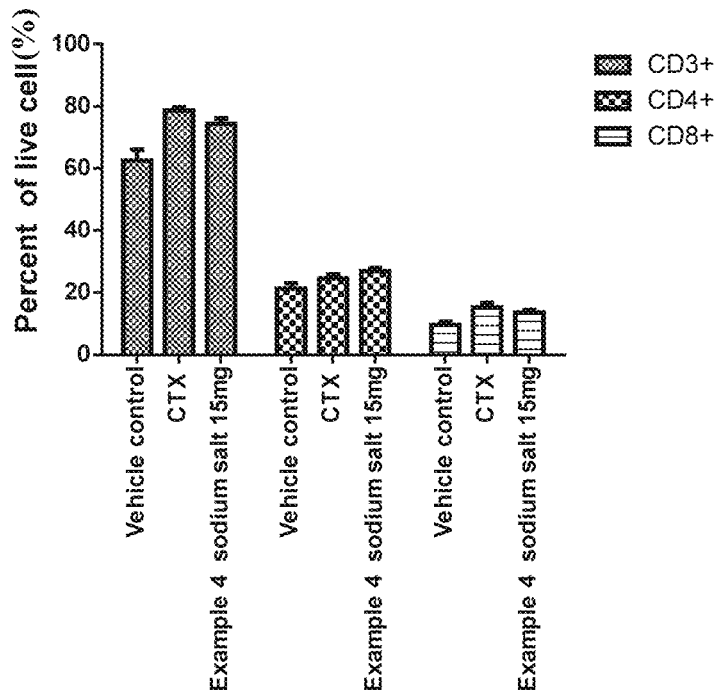
FIG. 5 illustrates the effect of sodium salt of Example 4 compound on the proportion of lymphocytes in the spleen samples.

T/C: Relative tumor proliferation rate
TGI: Tumor growth inhibition rate
NA: Not applicable
*P < 0.05 vs Vehicle control From the analysis of mechanism, it can be seen that Example 5 compound, sodium salt of Example 4 compound and hydrochloride form of Example 4 compound can increase the proportion of tumor-infiltrating lymphocytes (FIG. 4, Table 3) and sodium salt of Example 4 compound can increase the proportion of lymphocytes in the spleen samples (FIG. 5, Table 4).

TABLE 3

Effects of Example 4 and Example 5 on tumor-infiltrating T lymphocytes

| Group | CD3+ (%) | CD4+ (%) | CD8+ (%) |
|---|---|---|---|
| Vehicle control | 6.5 ± 0.8 | 4.8 ± 3.7 | 3.4 ± 0.1 |
| Cyclophosphamide (CTX) | 3.6 ± 1.5 | 1.7 ± 0.4 | 1.4 ± 0.3 |
| Example 5 45 mg | 10.1 ± 4.5 | 9.0 ± 4.7 | 5.2 ± 2.8 |
| Example 4 sodium salt 15 mg | 13.3 ± 6.9 | 7.2 ± 3.4 | 3.9 ± 1.4 |
| Example 4 hydrochloride form 15 mg | 15.2 ± 3.9 | 15.0 ± 10.7 | 9.6 ± 3.6 |

TABLE 4

Effects of sodium salt of Example 4 compound on T lymphocytes in spleen

| Group | CD3+ (%) | CD4+ (%) | CD8+ (%) |
|---|---|---|---|
| Vehicle control | 62.5 ± 7.6 | 21.3 ± 4.0 | 9.6 ± 2.1 |
| Cyclophosphamide (CTX) | 78.6 ± 2.5 | 24.6 ± 2.6 | 15.2 ± 3.1 |
| Example 4 sodium salt 15 mg | 74.3.3 ± 3.5 | 27.0 ± 1.8 | 13.6 ± 1.8 |

(2) Lung Metastasis Model of High Metastatic Melanoma B16F10

Figure 6:
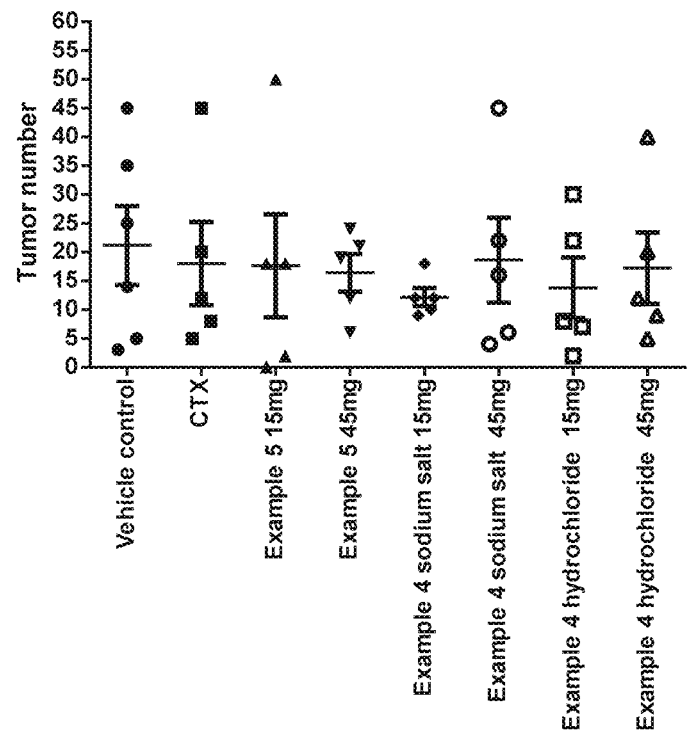
FIG. 6 illustrates the inhibitory effect of Example 5 compound, hydrochloride form of Example 4 compound and sodium salt of Example 4 compound on the number of lung metastases of high metastatic melanoma B16F10.

For metastatic lung cancer models with high metastatic melanoma B16F10, the sodium salt of Example 4 compound can significantly inhibit the number of lung metastases at 15 mg/kg dose (FIG. 6, Table 5).

TABLE 5

Example compounds' inhibition effect on Pulmonary metastasis model of Bl6F10

| Group | Dose | Number (End/Begin) | Body weight(g) Mean ± SD Begin | End | Tumor number T/C % X ± SD (TGI %) |
|---|---|---|---|---|---|
| Vehicle control | | 6/6 | 20.2 ± 0.4 | 21.0 ± 0.3 | 21 ± 15 NA |
| Cyclophosphamide (CTX) | 80 mg/kg | 5/5 | 20.1 ± 0.8 | 21.4 ± 0.5 | 18 ± 14 85.7(14.3) |
| Example 5 | 15 mg/kg | 5/5 | 20.6 ± 0.7 | 20.2 ± 1.5 | 18 ± 18 85.7(14.3) |
|  | 45 mg/kg | 5/5 | 20.5 ± 0.6 | 21.2 ± 0.7 | 16 ± 7 76.2(23.8) |
| Example 4 sodium salt | 15 mg/kg | 5/5 | 20.1 ± 0.9 | 21.5 ± 1.2 | 12 ± 3 57.1(42.3) |
|  | 45 mg/kg | 5/5 | 20.3 ± 0.6 | 21.4 ± 0.3 | 19 ± 15 90.5(9.5) |
| Example 4 hydrochloride form | 15 mg/kg | 5/5 | 20.5 ± 0.6 | 21.3 ± 1.0 | 14 ± 10 66.7(33.3) |
|  | 45 mg/kg | 5/5 | 20.6 ± 1.0 | 21.3 ± 0.4 | 17 ± 12 81.0(19.0) |

T/C: Relative tumor proliferation rate

TGI: Tumor growth inhibition rate

NA: Not applicable

*P < 0.05 vs Vehicle control

Figure 7:
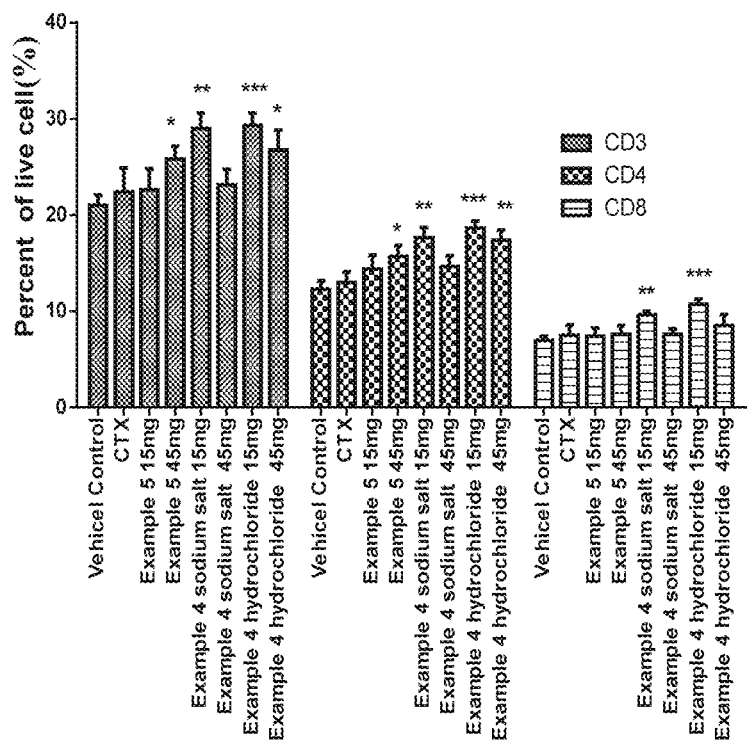
FIG. 7 illustrates the effect of Example 5 compound, hydrochloride form of Example 4 compound and sodium salt of Example 4 compound on the percentage of lymphocyte in mouse blood.

From analysis of the mechanism, it can be seen Example 4 and Example 5 could increase the percentage of lymphocyte in mouse blood (FIG. 7, Table 6).

TABLE 6

Example compounds' effect on the percentage of T ymphocyte in mouse blood

| Group | CD3+ | CD4+ | CD8+ |
|---|---|---|---|
| Vehicle control | 21.0 ± 2.6 | 12.3 ± 2.1 | 7.0 ± 1.1 |
| Cyclophosphamide (CTX) | 22.4 ± 5.5 | 13.0 ± 2.4 | 7.5 ± 2.4 |
| Example 5 15 mg | 22.7 ± 4.8 | 14.4 ± 3.3 | 7.4 ± 1.9 |
| Example 5 45 mg | 25.8 ± 3.0 | 15.7 ± 2.5 | 7.6 ± 1.8 |
| Example 4 sodium salt 15 mg | 29.0 ± 3.7 | 17.8 ± 2.4 | 9.6 ± 0.8 |
| Example 4 sodium salt 45 mg | 23.2 ± 3.6 | 14.7 ± 2.5 | 7.6 ± 1.3 |
| Example 4 hydrochloride 15 mg | 29.3 ± 2.9 | 18.6 ± 1.6 | 10.7 ± 1.3 |
| Example 4 hydrochloride 45 mg | 26.8 ± 4.1 | 17.4 ± 2.0 | 8.5 ± 2.3 |

(3) Subcutaneous Xenograft Model of Mouse Breast Cancer EMT6

Figure 8:
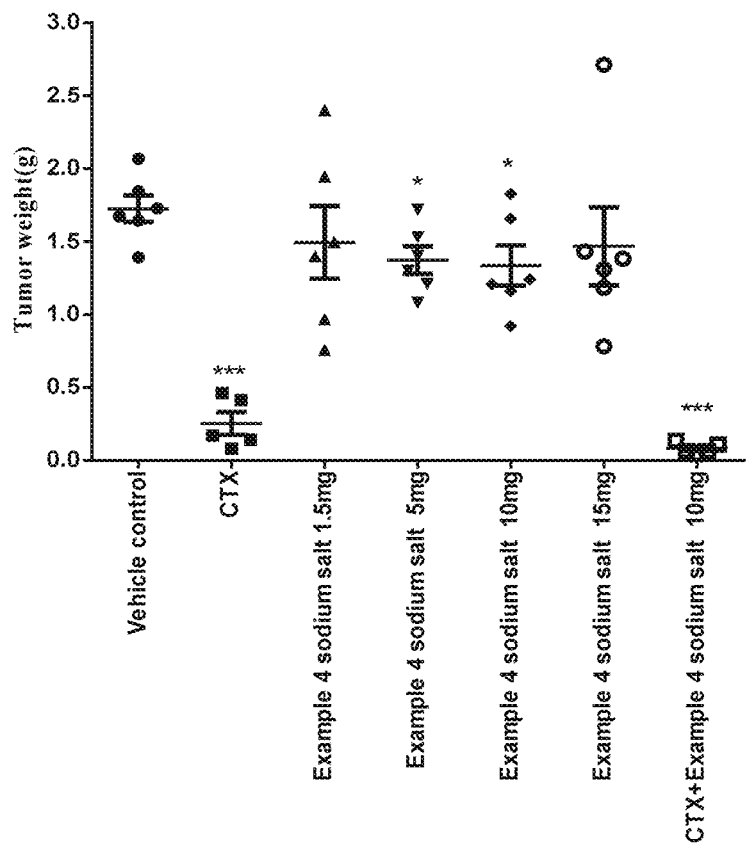
FIG. 8 illustrates the inhibitory effect of sodium salt of Example 4 compound on tumor weight of subcutaneous xenograft of mouse breast cancer EMT6.

For subcutaneous xenograft model of mouse breast cancer EMT6, sodium salt of Example 4 compound has some inhibition effect on mouse breast cancer EMT6. At the dose of 10 mg and 15 mg, sodium salt of Example 4 compound has 20% and 22% inhibition effect respectively (FIG. 8, Table 6). In addition, the combination of sodium salt of Example 4 compound and Cyclophosphamide can significantly increase the tumor growth inhibition rate of Cyclophosphamide from 85% to 95% (FIG. 8, Table 7).

TABLE 7

Example 4 compound's inhibition effect on mouse subcutaneous xenograft of EMT6

| Group | Dose | Number (End/Begin) | Body weight (g) Mean ± SD Begin | End | Tumorweight(g) X ± SD | T/C % (TGI %) |
|---|---|---|---|---|---|---|
| Vehicle control | | 6/6 | 18.4 ± 0.3 | 20.3 ± 0.3 | 1.72 ± 0.22 | NA |
| Cyclophosphamide | 60 mg/kg | 5/5 | 18.4 ± 0.3 | 19.4 ± 0.7* | 0.25 ± 0.17*** | 14.1(85.9)*** |
| Cyclophosphamide + Example 4 sodium salt | 60 mg/kg + 10 mg/kg | 5/5 | 17.8 ± 1.1 | 18.9 ± 0.4*** | 0.08 ± 0.04*** | 4.8(95.2)*** |
| Example 4 sodium salt | 1.5 mg/kg | 6/6 | 18.4 ± 0.9 | 22.0 ± 1.6 | 1.5 ± 0.61 | 86.9(13.1) |
| | 5 mg/kg | 6/6 | 18.4 ± 0.4 | 21.0 ± 1.6 | 1.37 ± 0.23* | 79.8(20.2)* |
| | 10 mg/kg | 6/6 | 18.4 ± 0.6 | 21.6 ± 1.3 | 1.34 ± 0.34* | 77.7(22.3)* |
| | 15 mg/kg | 6/6 | 18.5 ± 0.4 | 22.0 ± 1.1* | 1.47 ± 0.65 | 85.3(14.7) |

Figure 9:
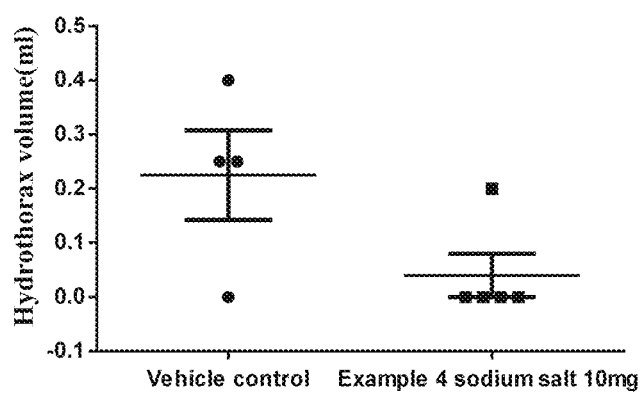
FIG. 9 illustrates the inhibitory effect of sodium salt of Example 4 compound on mouse Lewis lung cancer hydrothorax.
Figure 10:
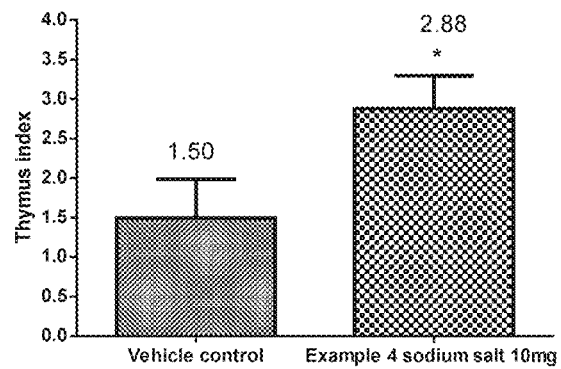
FIG. 10 illustrates sodium salt of Example 4 compound could increase mouse thymus index.

T/C: Relative tumor proliferation rate
TGI: Tumor growth inhibition rate
NA: Not applicable
*P < 0.05 vs Vehicle control (4) Mouse Lewis Lung Cancer Hydrothorax Model Sodium salt of Example 4 compound has inhibition effect on mouse Lewis lung cancer hydrothorax model. The hydrothorax incidence rate in vehicle control group was 75%, whereas at the dose of 10 mg, sodium salt of Example 4 compound can reduce the rate to 33% (Table 8). The mean volume of the hydrothorax of mice was 0.3 ml in the vehicle control group and in the group administrated with sodium salt of Example 4 compound the mouse only had 0.2 ml of hydrothorax (FIG. 9, Table 9). Further, sodium salt of Example 4 compound can significantly increase thymus index (FIG. 10).

TABLE 8

Example 4's effect on hydrothorax incidence rate of Lewis lung cancer

| Vehicle control | Example 4 sodium salt 10 mg |
|---|---|
| 75% | 33% |

TABLE 9

Example 4's effect on hydrothorax volume of Lewis lung cancer

| Vehicle control | Example 4 sodium salt 10 mg |
|---|---|
| 0.3 ml | 0.2 ml |

(5) Subcutaneous Xenograft Model of Mouse Colon Cancer MC38

Figure 11:
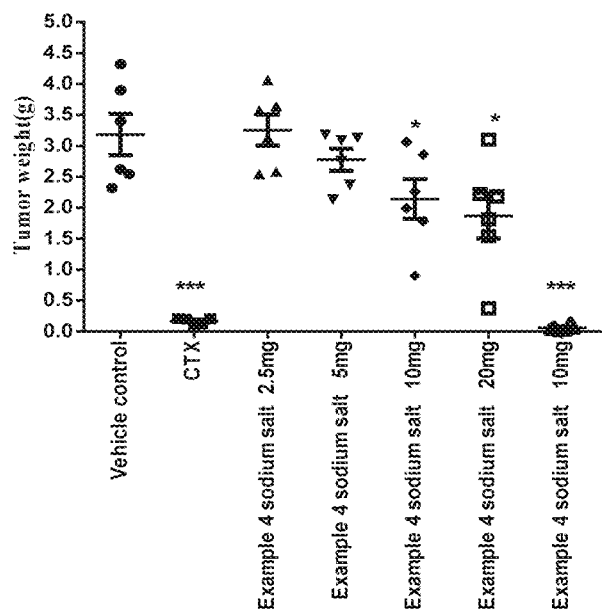
FIG. 11 illustrates the inhibitory effect of sodium salt of Example 4 compound on subcutaneous xenograft of mouse colon cancer MC38.

For subcutaneous xenograft model of mouse colon cancer MC38, sodium salt of Example 4 compound has significant inhibition effect. Furthermore, sodium salt of Example 4 compound has a synergistic antitumor effect on this cancer with Cyclophosphamide (CTX) (FIG. 11, Table 10).

TABLE 10

Example compounds' effect on subcutaneous xenograft model of mouse colon cancer MC38

| Group | Dose | Number (End/begin) | Body weight (g) Mean ± SD Begin | End | Tumor weight(g) Mean ± SD | T/C % (TGI %) |
|---|---|---|---|---|---|---|
| Vehicle control | | 6/6 | 17.9 ± 0.5 | 22.3 ± 1.1 | 3.18 ± 0.82 | NA |
| Cyclophosphamide | 60 mg/kg | 6/6 | 17.9 ± 0.6 | 19.1 ± 0.8*** | 0.17 ± 0.05*** | 5.4(94.6)*** |
| Cyclophosphamide + Example 4 sodium salt | 60 mg/kg + 10 mg | 6/6 | 18.2 ± 0.6 | 18.8 ± 0.8*** | 0.06 ± 0.04*** ## | 1.9(98.1)*** ## |
| Example 4 | 2.5 mg/kg | 6/6 | 18.0 ± 0.4 | 21.9 ± 0.7 | 3.25 ± 0.61 | −2.3(102.3) |
| | 5 mg/kg | 6/6 | 18.2 ± 0.3 | 22.8 ± 0.6 | 2.78 ± 0.44 | 87.3(12.7) |
| | 10 mg/kg | 6/6 | 18.2 ± 0.3 | 21.5 ± 0.8 | 2.14 ± 0.78* | 67.3(32.7)* |
| | 20 mg/kg | 6/6 | 18.2 ± 0.4 | 20.9 ± 1.1 | 1.87 ± 0.90* | 58.8(41.2)* |

T/C: Relative tumor proliferation rate
TGI: Tumor growth inhibition rate
NA: Not applicable
*P < 0.05 vs Vehicle control;
***P < 0.001 vs Vehicle control;
p < 0.01 vs Cyclophosphamide (CTX)

49

4. The Interaction of Example 4 Compound/PD-L1 Antibody with PD-L1 Protein was Tested by Biacore (1) Experimental Principle Surface plasmon is a kind of electromagnetic wave on the surface of metal, produced by the interaction of photon and electron in free vibration. Surface plasmon resonance (SPR) is an optical phenomenon that occurs on the surface of two kinds of media, which can be induced by photon or electron. The phenomenon of total reflection of light from light dense medium into light scattering medium will form evanescent wave into light scattering medium. When the total reflected evanescent wave meets the plasma wave on the metal surface, the resonance may occur, and the energy of reflected light decreases and the resonance peak appears on the reflected light energy spectrum. This resonance is called the surface plasmon resonance. The incident angle of the surface plasmon resonance is called the SPR angle. The SPR biosensor provides a sensitive, real-time, non-label detection technique for monitoring the interaction of molecules. The sensor detects the change of the SPR angle, and SPR is also related to the refractive index of the metal surface. When an analyte is bond on the surface of the chip, it leads to the change of the refractive index of the chip surface, which leads to the change of the SPR angle. This is the basic principle of the real-time detection of intermolecular interaction by the SPR biosensor. In the interaction analysis, the change of SPR angle is recorded on the sensor map in real time.

(2) Experimental Methods

The PD-L1 protein was captured on the Fc4 channel of NTA chip by capture method, and the buffer system was PBS-P+, pH7.4, 0.01% DMSO. A series of concentration of compounds and PD-L1 antibodies were prepared and flowed through the surface of the chip for the determination of interaction.

(3) Experimental Results

TABLE 11

The affinity of Example 4 compound and PD-L1 antibody to PD-L1

| Ligand | Analyte | ka (1/Ms) | kd (1/s) | KD (M) |
|---|---|---|---|---|
| PD-L1 protein | PD-L1 antibody | 2.016E+5 | 1.358E−4 | 6.736E−10 |
| PD-L1protein | Example 4 | 1.390E+6 | 2.815E−5 | 2.025E−11 |

Figure 12:
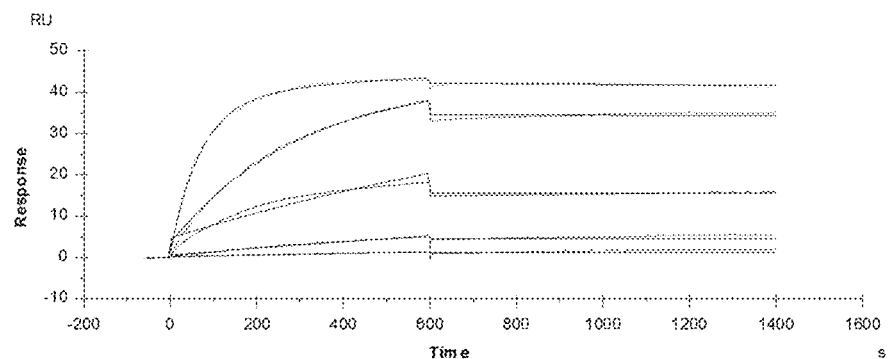
FIG. 12 illustrates the binding of the Example 4 compound to PD-L1.
Figure 13:
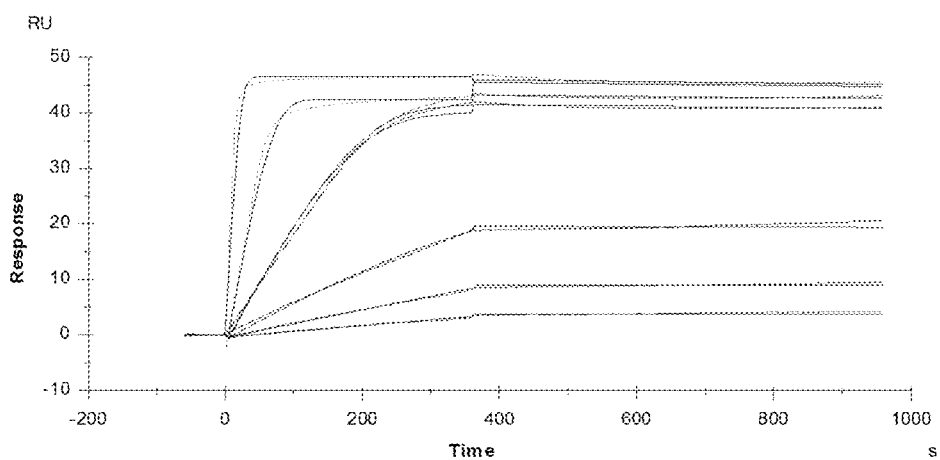
FIG. 13 illustrates the binding of the Example 4 compound to PD-L1.
Figure 14:
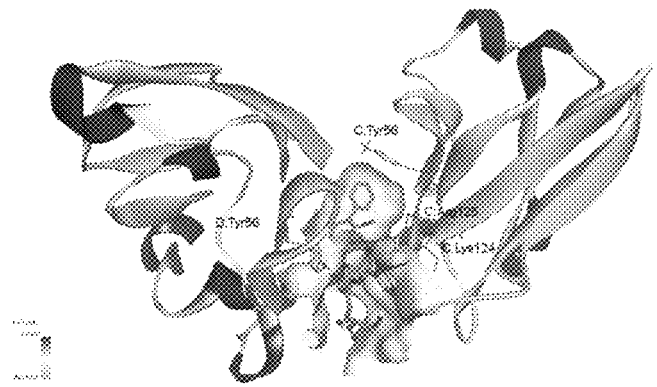
FIG. 14 illustrates Example 4 compound has a stronger ability of binding PD-L1 than that of the antibody of PD-L1.

It was preliminarily determined that the binding protein of the Example 4 is PD-L1 (FIG. 12). Further Biacore experiments confirmed that the combination of Example 4 has a strong ability of binding PD-L1 and the affinity kD value is 2.025E−11 which is even stronger than that of the antibody of PD-L1 (Table 11, FIG. 12-14).

50

What is claimed is:

1. A nicotinyl alcohol ether derivative of Formula (I):

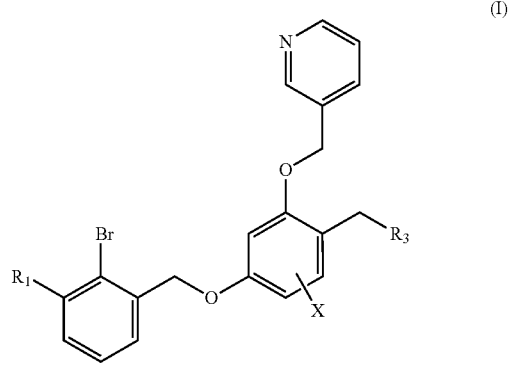

or a stereoisomer or a pharmaceutically acceptable salt thereof, wherein:

$R_1$ is selected from

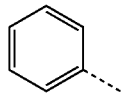

and

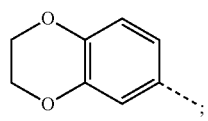

$R_3$ is selected from substituted $C_1$-$C_8$ saturated alkylamino, substituted $C_2$-$C_6$ unsaturated alkylamino, and substituted N-containing $C_2$-$C_6$ heterocycle-1-yl, wherein each is mono-, di-, tri-, or tetra-substituted with substituent(s) selected from hydrogen, fluorine, chlorine, bromine, iodine, hydroxy, $C_1$-$C_5$ alkyl, $C_1$-$C_5$ alkoxy, amino, $C_1$-$C_6$ alkylamino, acetylamino, cyano, ureido (—NH(C═O)NH$_2$), guanidine (—NH(C═NH)NH$_2$), ureido amino (—NH—NH(C═O)NH$_2$), guanidino amino (—NH—NH(C═NH)NH$_2$), sulfonylamino (—NHSO$_3$H), sulfamoyl (—SO$_2$NH$_2$), methanesulfonylamino (—NH—SO$_2$CH$_3$), hydroxyformyl (—COOH), $C_1$-$C_8$ alkoxyl carbonyl, sulfydryl, imidazolyl, thiazolyl, oxazolyl, tetrazolyl,

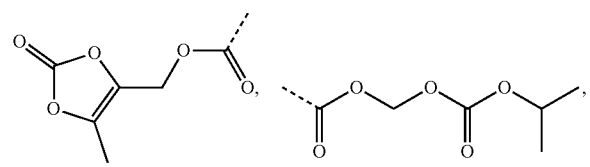

and

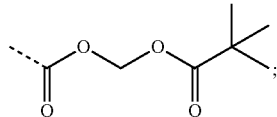

and

X is selected from hydrogen, fluorine, chlorine, bromine, iodine, $C_1$-$C_4$ alkyl, ethenyl, trifluoromethyl, and methoxy.

2. A nicotinyl alcohol ether derivative of claim 1, represented by formula (IA), or a pharmaceutically acceptable salt or a stereoisomer thereof:

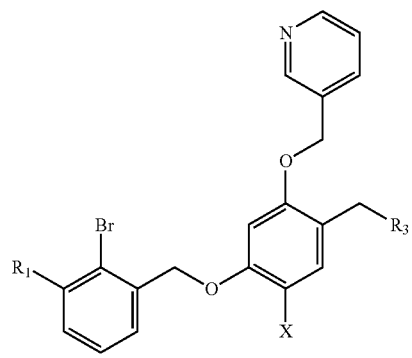 (IA)

wherein:

$R_1$ is selected from

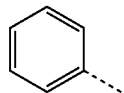

and

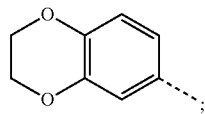

;

$R_3$ is selected from substituted $C_1$-$C_8$ saturated alkylamino, substituted $C_2$-$C_6$ unsaturated alkylamino, and substituted N-containing $C_2$-$C_6$ heterocycle-1-yl, wherein each is mono-, di-, tri-, or tetra-substituted with substituent(s) selected from hydrogen, fluorine, chlorine, bromine, iodine, hydroxy, $C_1$-$C_5$ alkyl, $C_1$-$C_5$ alkoxy, amino, $C_1$-$C_6$ alkylamino, acetylamino, cyano, ureido (—NH(C=O)NH$_2$), guanidino (—NH(C=NH)NH$_2$), ureido amino (—NH—NH(C=O)NH$_2$), guanidino amino (—NH—NH(C=NH)NH$_2$), sulfonylamino (—NHSO$_3$H), sulfamoyl (—SO$_2$NH$_2$), methanesulfonylamino (—NH—SO$_2$CH$_3$), hydroxyformyl (—COOH), $C_1$-$C_8$ alkoxyl carbonyl, sulfydryl, imidazolyl, thiazolyl, oxazolyl, tetrazolyl,

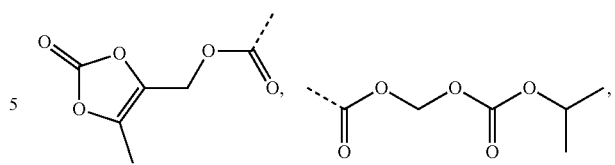

and

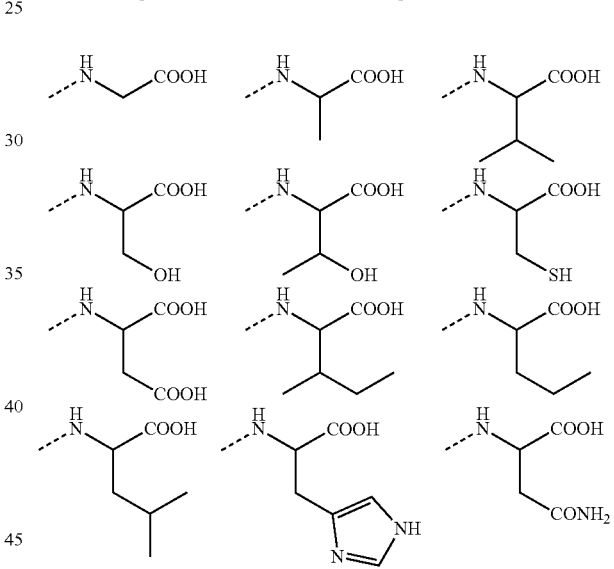

and

X is selected from hydrogen, fluorine, chlorine, bromine, iodine, $C_1$-$C_4$ alkyl, ethenyl, trifluoromethyl, and methoxy.

3. A nicotinyl alcohol ether derivative of claim 2, or a pharmaceutically acceptable salt, or a stereoisomer thereof, wherein $R_3$ is of one of the following formulae:

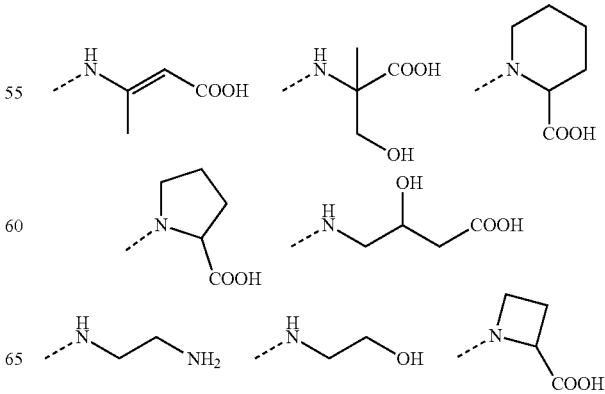

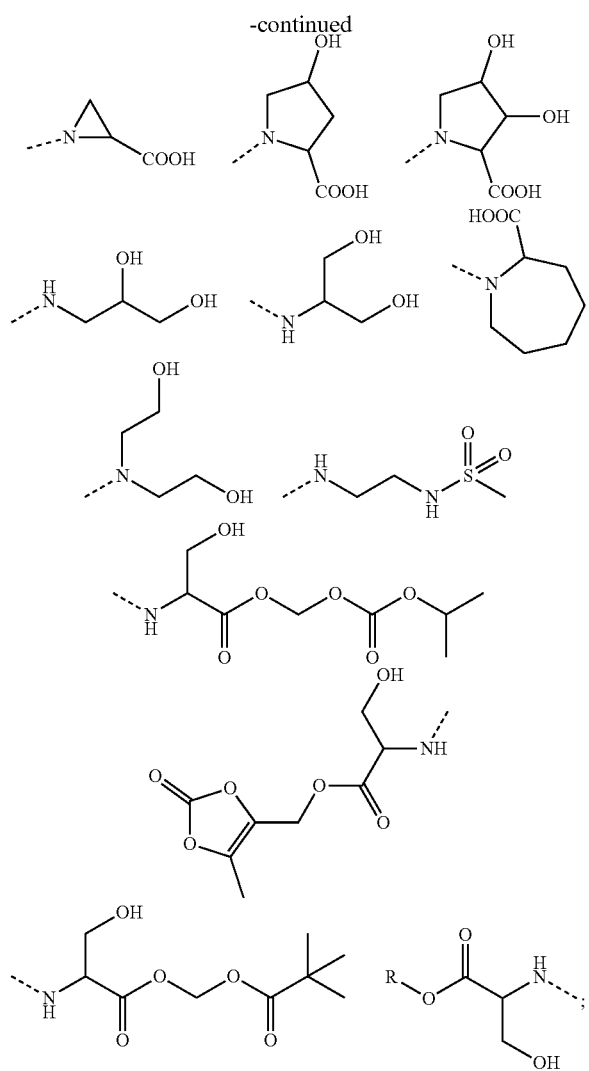

wherein R is selected from methyl, ethyl, propyl, isopropyl, butyl, pentyl, hexyl, heptyl, and octyl; and X is selected from hydrogen, fluorine, chlorine, bromine, methyl, ethenyl, and trifluoromethyl.

4. A nicotinyl alcohol ether derivative of claim 2, represented by formula (IA-1), or a pharmaceutically acceptable salt or a stereoisomer thereof:

(IA-1)

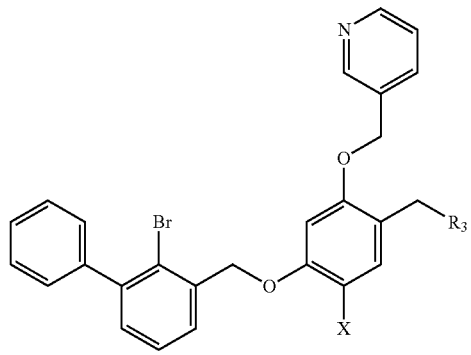

wherein:
R$_3$ is selected from substituted C$_1$-C$_8$ saturated alkylamino, substituted C$_2$-C$_6$ unsaturated alkylamino, and substituted N-containing C$_2$-C$_6$ heterocycle-1-yl, wherein each is mono-, di-, tri-, or tetra-substituted with substituent(s) selected from hydrogen, fluorine, chlorine, bromine, iodine, hydroxy, C$_1$-C$_5$ alkyl, C$_1$-C$_5$ alkoxy, amino, C$_1$-C$_6$ alkylamino, acetylamino, cyano, ureido (—NH(C=O)NH$_2$), guanidino (—NH(C=NH)NH$_2$), ureido amino (—NH—NH(C=O)NH$_2$), guanidino amino (—NH—NH(C=NH)NH$_2$), sulfonylamino (—NHSO$_3$H), sulfamoyl (—SO$_2$NH$_2$), methanesulfonylamino (—NH—SO$_2$CH$_3$), hydroxyformyl (—COOH), C$_1$-C$_8$ alkoxyl carbonyl, sulfydryl, imidazolyl, thiazolyl, oxazolyl, tetrazolyl,

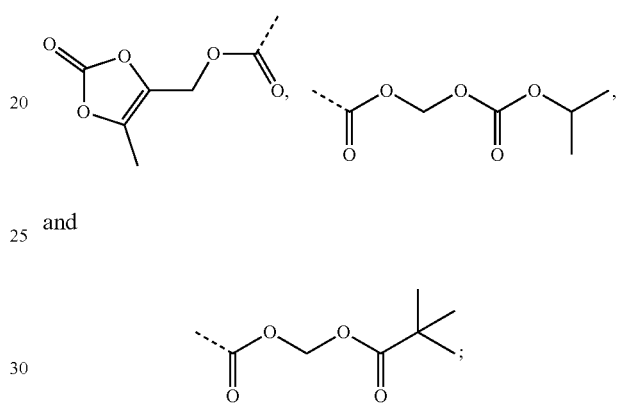

and

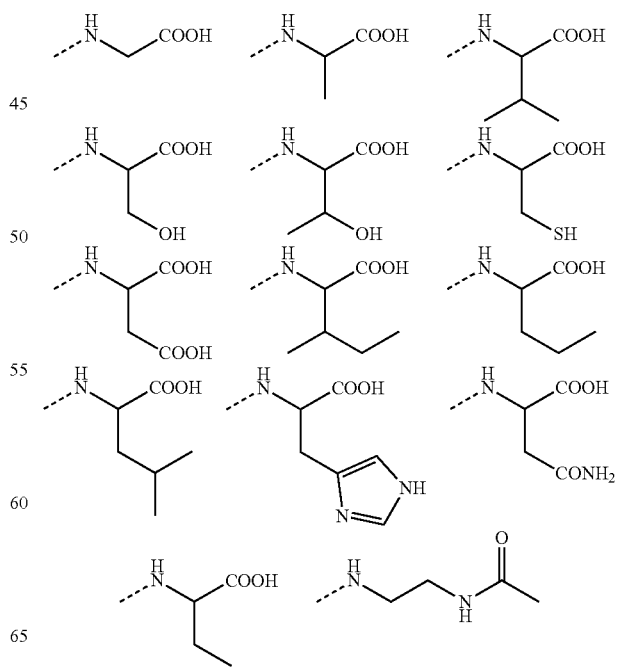

and
X is selected from hydrogen, fluorine, chlorine, bromine, iodine, C$_1$-C$_4$ alkyl, ethenyl, trifluoromethyl, and methoxy.

5. A nicotinyl alcohol ether derivative of claim 4, or a pharmaceutically acceptable salt, or a stereoisomer thereof, wherein R$_3$ is of one of the following formulae:

-continued

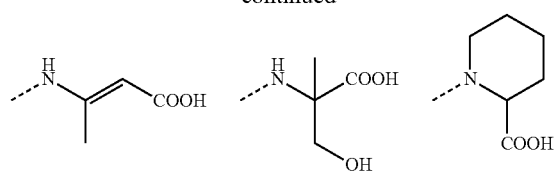
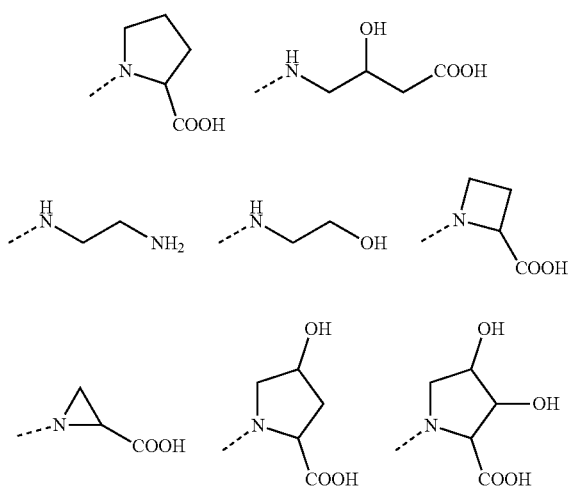
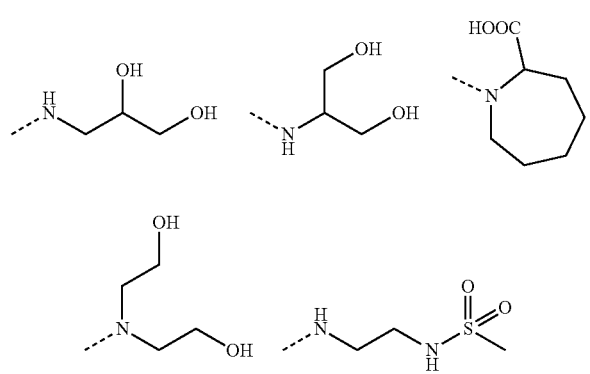
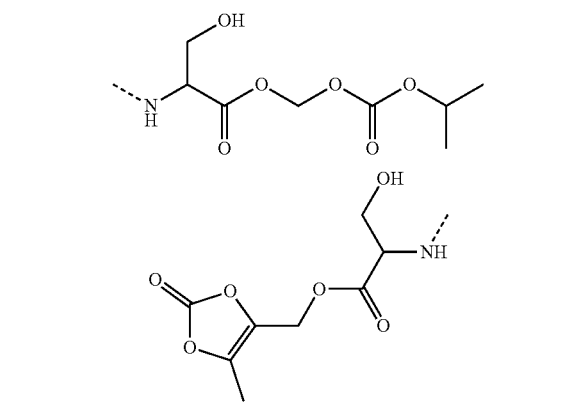
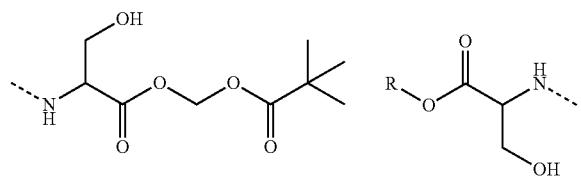

wherein R is selected from methyl, ethyl, propyl, isopropyl, butyl, pentyl, hexyl, heptyl, and octyl; and X is selected from hydrogen, fluorine, chlorine, bromine, methyl, ethenyl, and trifluoromethyl.

6. A nicotinyl alcohol ether derivative of claim 2, represented by formula (IA-2), or a pharmaceutically acceptable salt or a stereoisomer thereof:

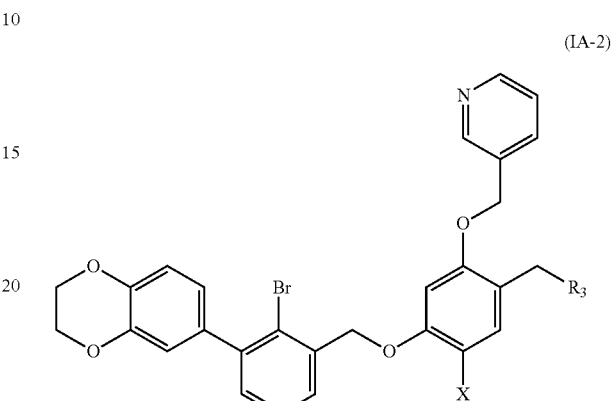

(IA-2)

wherein:

$R_3$ is selected from substituted $C_1$-$C_8$ saturated alkylamino, substituted $C_2$-$C_6$ unsaturated alkylamino, and substituted N-containing $C_2$-$C_6$ heterocycle-1-yl, wherein each is mono-, di-, tri-, or tetra-substituted with substituent(s) selected from hydrogen, fluorine, chlorine, bromine, iodine, hydroxy, $C_1$-$C_5$ alkyl, $C_1$-$C_5$ alkoxy, amino, $C_1$-$C_6$ alkylamino, acetylamino, cyano, ureido (—NH(C=O)NH$_2$), guanidino (—NH(C=NH)NH$_2$), ureido amino (—NH—NH(C=O)NH$_2$), guanidino amino (—NH—NH(C=NH)NH$_2$), sulfonylamino (—NHSO$_3$H), sulfamoyl (—SO$_2$NH$_2$), methanesulfonylamino (—NH—SO$_2$CH$_3$), hydroxyformyl (—COOH), $C_1$-$C_8$ alkoxyl carbonyl, sulfydryl, imidazolyl, thiazolyl, oxazolyl, tetrazolyl,

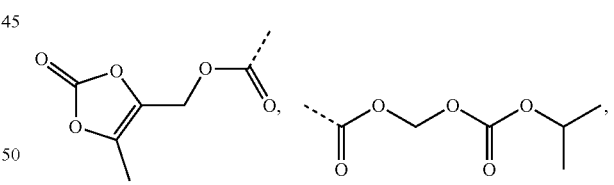

and

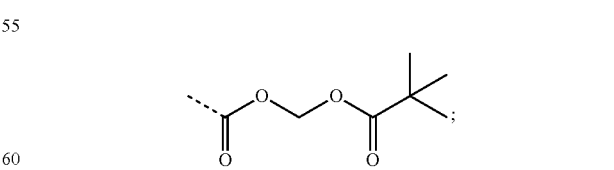

and

X is selected from hydrogen, fluorine, chlorine, bromine, iodine, $C_1$-$C_4$ alkyl, ethenyl, trifluoromethyl, and methoxy.

7. A nicotinyl alcohol ether derivative of claim 6, or a pharmaceutically acceptable salt, or a stereoisomer thereof, wherein $R_3$ is of one of the following formulae:

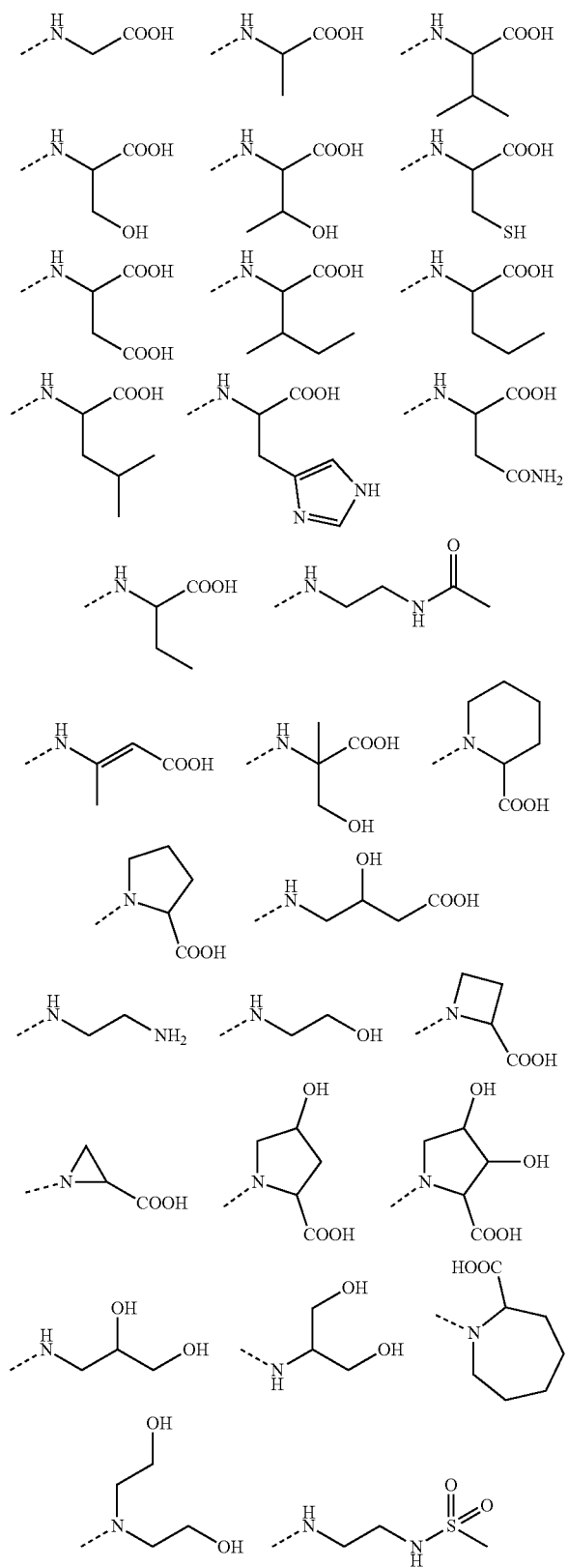

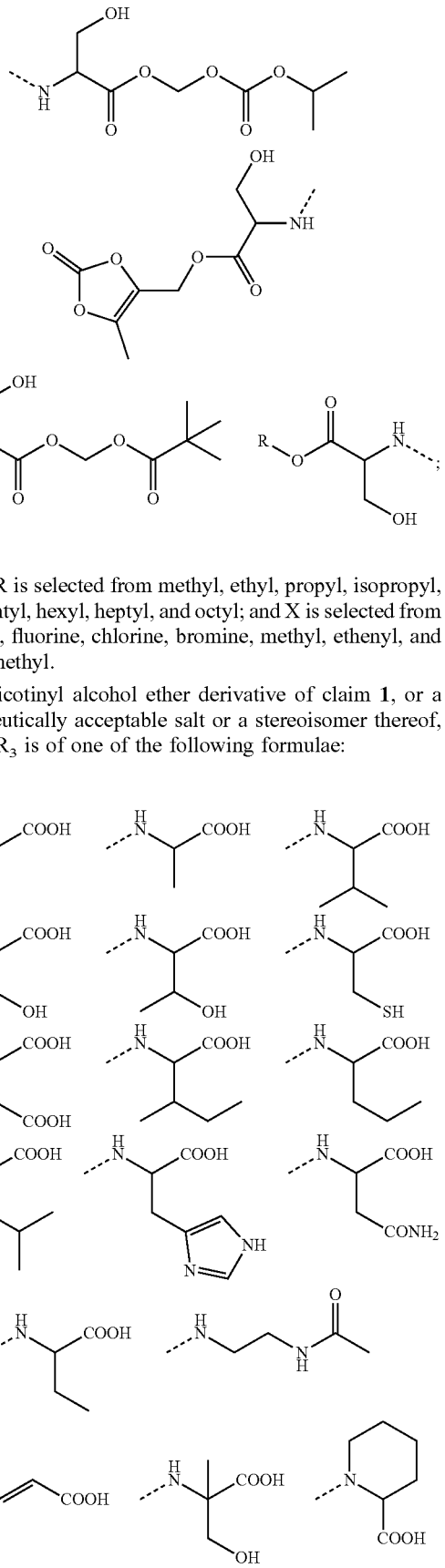

wherein R is selected from methyl, ethyl, propyl, isopropyl, butyl, pentyl, hexyl, heptyl, and octyl; and X is selected from hydrogen, fluorine, chlorine, bromine, methyl, ethenyl, and trifluoromethyl.

8. A nicotinyl alcohol ether derivative of claim 1, or a pharmaceutically acceptable salt or a stereoisomer thereof, wherein $R_3$ is of one of the following formulae:

-continued

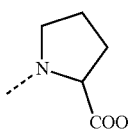 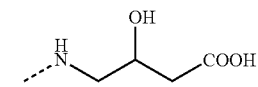

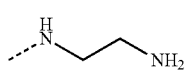 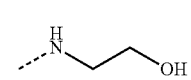 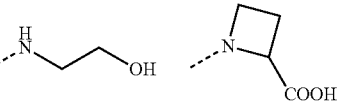

 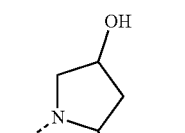 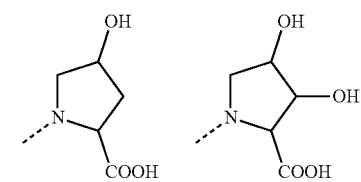

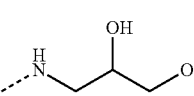 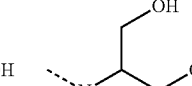 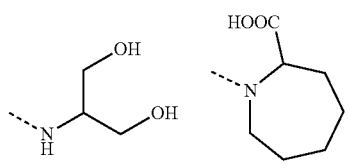

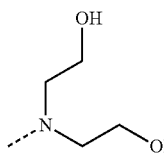 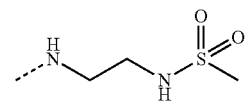

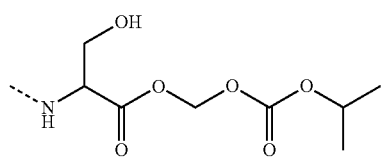

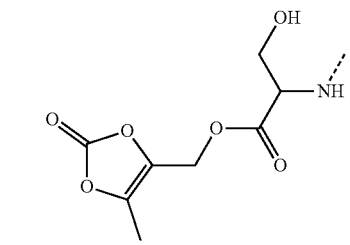

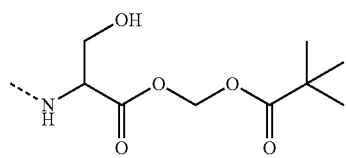 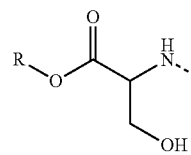

wherein R is selected from methyl, ethyl, propyl, isopropyl, butyl, pentyl, hexyl, heptyl, and octyl; and X is selected from hydrogen, fluorine, chlorine, bromine, methyl, ethenyl, and trifluoromethyl.

9. A nicotinyl alcohol ether derivative of claim 1, or a pharmaceutically acceptable salt or a stereoisomer thereof, wherein the compound is selected from:

Ethyl N-(4-(2-bromo-3-phenylbenzyloxy)-5-chloro-2-(pyridin-3-yl-methyleneoxy)benzyl) serinate dihydrochloride

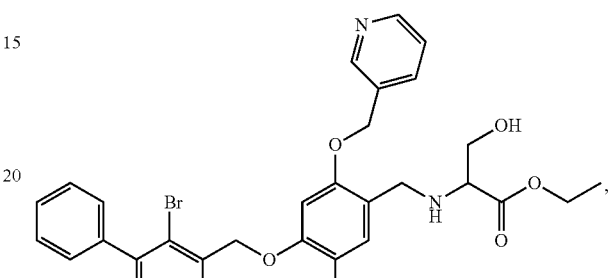

N-(4-(2-bromo-3-phenylbenzyloxy)-5-chloro-2-(pyridin-3-yl-methyleneoxy)benzyl) serine

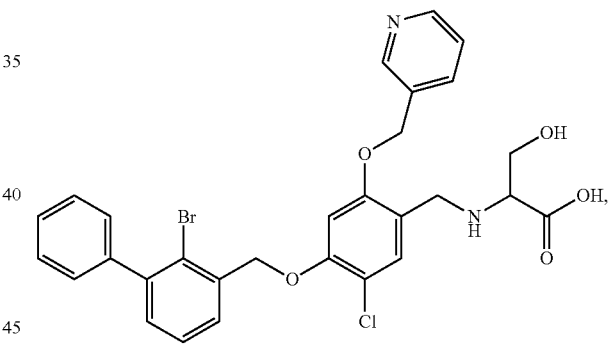

(S)-Ethyl N-(4-(2-bromo-3-phenylbenzyloxy)-5-chloro-2-(pyridin-3-yl-methyleneoxy) benzyl)serinate

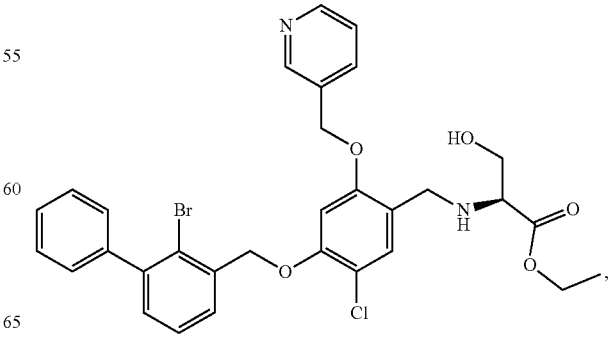

| 61 | 62 |

(S)—N-(4-(2-bromo-3-phenylbenzyloxy)-5-chloro-2-(pyridin-3-yl-methyleneoxy) benzyl) serine (R)-Ethyl N-(4-(2-bromo-3-phenylbenzyloxy)-5-chloro-2-(pyridin-3-yl-methyleneoxy)benzyl) serinate

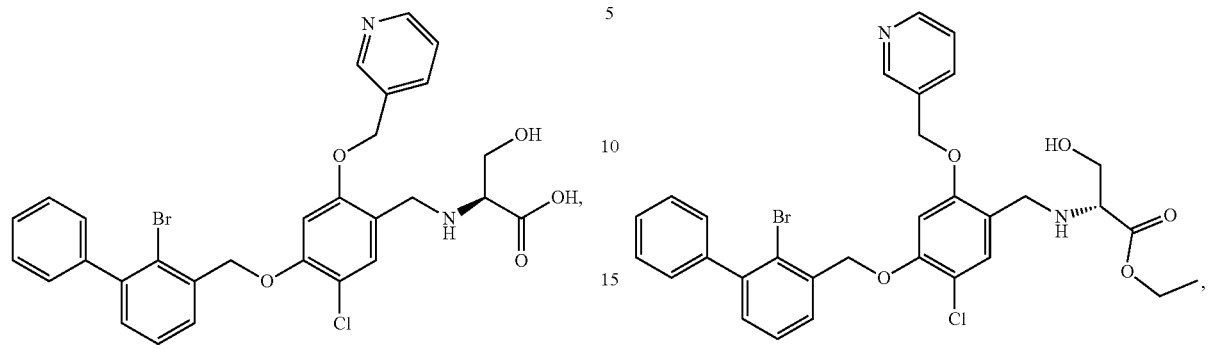

(S)-Ethyl N-(4-(2-bromo-3-phenylbenzyloxy)-5-chloro-2-(pyridin-3-yl-methyleneoxy)benzyl) serinate dihydrochloride (R)—N-(4-(2-bromo-3-phenylbenzyloxy)-5-chloro-2-(pyridin-3-yl-methyleneoxy) benzyl) serine

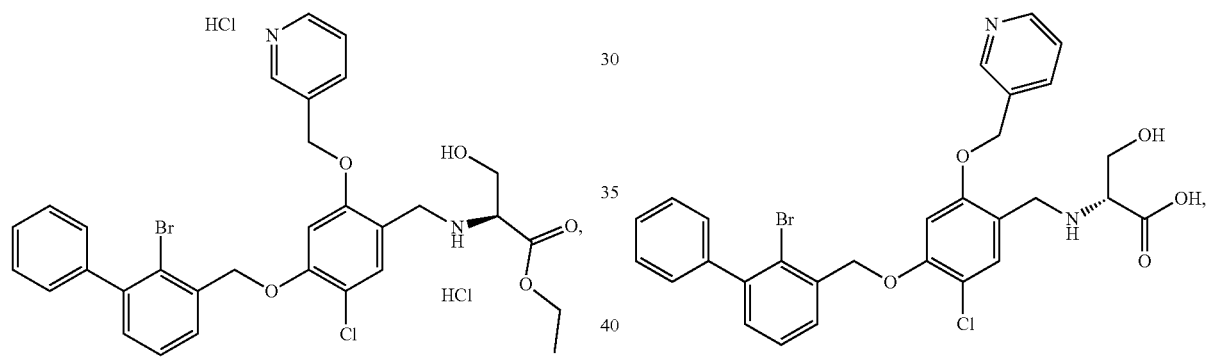

(S)-isopropyl N-(4-(2-bromo-3-phenylbenzyloxy)-5-chloro-2-(pyridin-3-yl-methyleneoxy)benzyl) serinate dihydrochloride N-(4-(2-bromo-3-phenylbenzyloxy)-5-chloro-2-(pyridin-3-yl-methyleneoxy)benzyl) glycine

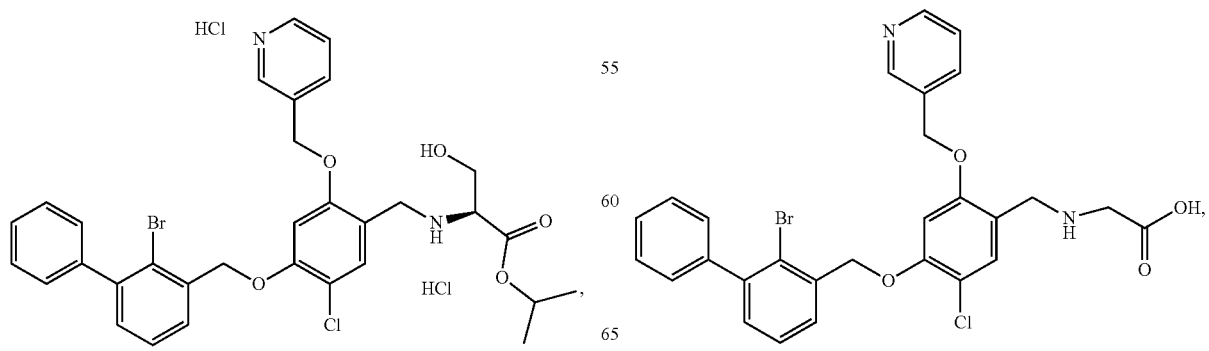

63

N-(4-(2-bromo-3-phenylbenzyloxy)-5-chloro-2-(pyridin-3-yl-methyleneoxy)benzyl) valine

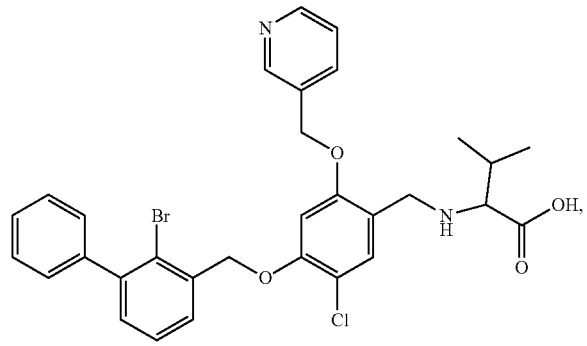 [SMILES: CC(C)C(NCc1cc(Cl)c(OCc2cccc(-c3ccccc3)c2Br)cc1OCc1cccnc1)C(=O)O]

(E)-3-(4-(2-bromo-3-phenylbenzyloxy)-5-chloro-2-(pyridin-3-yl-methyleneoxy) benzylamino) but-2-enenitrile

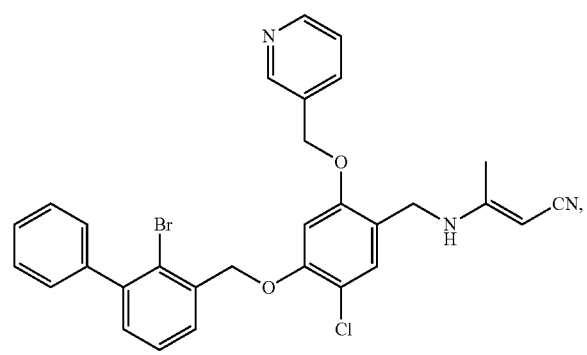 [SMILES: C/C(=C\C#N)NCc1cc(Cl)c(OCc2cccc(-c3ccccc3)c2Br)cc1OCc1cccnc1]

N,N-bis(hydroxyethyl)-4-(2-bromo-3-phenylbenzyloxy)-5-chloro-2-(pyridin-3-yl-methyleneoxy) benzylamine

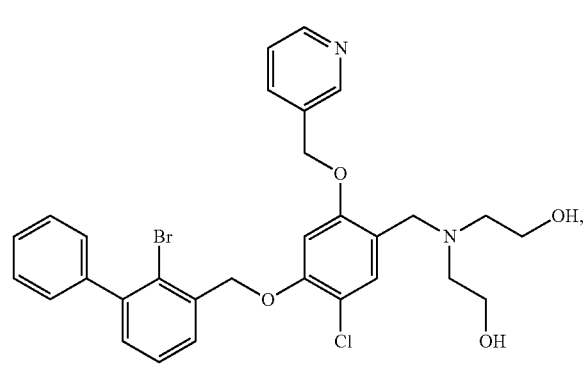 [SMILES: OCCN(CCO)Cc1cc(Cl)c(OCc2cccc(-c3ccccc3)c2Br)cc1OCc1cccnc1]

64

N-(2-methanesulfonaminoethyl)-4-(2-bromo-3-phenylbenzyloxy)-5-chloro-2-(pyridin-3-yl-methyleneoxy) benzylamine

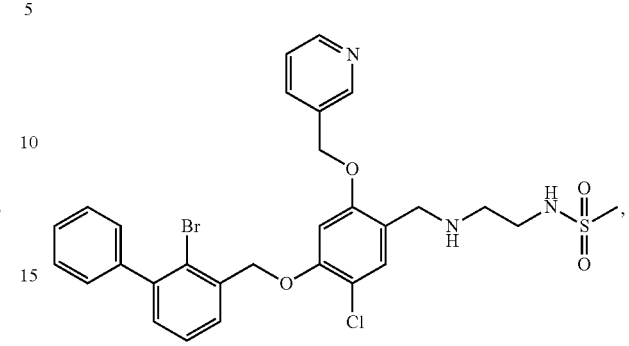

N-(2-acetylaminoethyl)-4-(2-bromo-3-phenylbenzyloxy)-5-chloro-2-(pyridin-3-yl-methyleneoxy) benzylamine

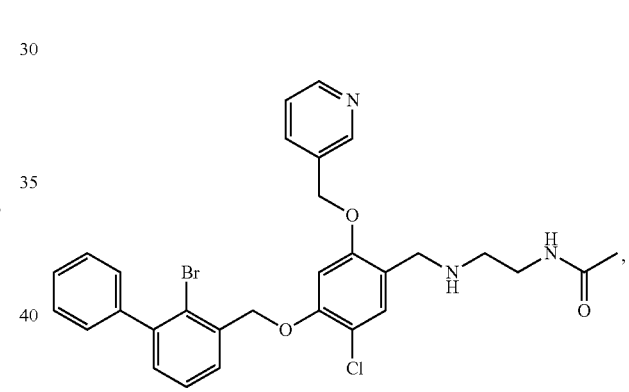

(E)-3-(4-(2-bromo-3-phenylbenzyloxy)-5-chloro-2-(pyridin-3-yl-methyleneoxy) benzylamino) hut-2-enoic acid

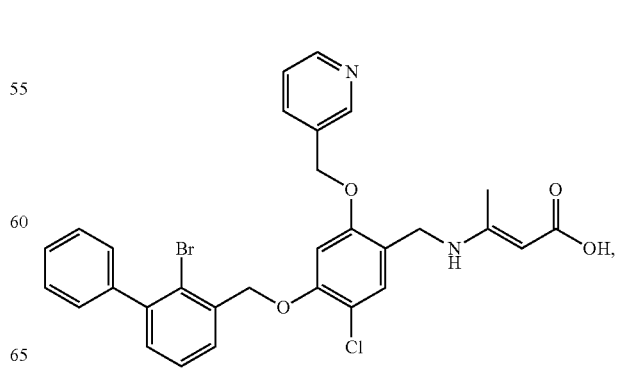

65

2-(4-(2-bromo-3-phenylbenzyloxy)-5-chloro-2-(pyridin-3-yl-methyleneoxy) benzylamino) ethanesulfonic acid

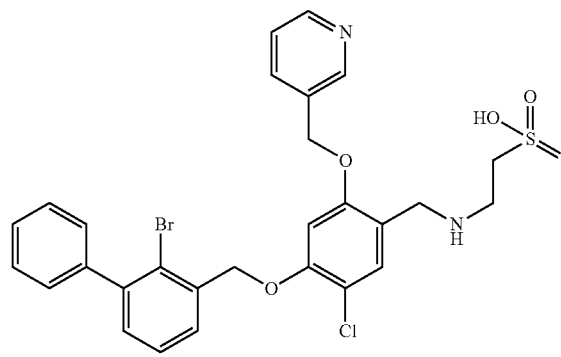

N-(4-(2-bromo-3-phenylbenzyloxy)-5-chloro-2-(pyridin-3-yl-methyleneoxy)benzyl) leucine

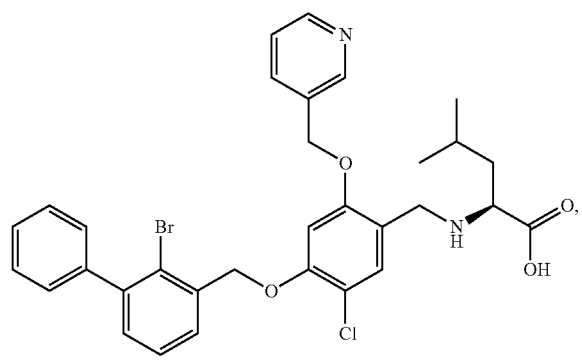 [SMILES: CC(C)C[C@H](NCc1cc(Cl)c(OCc2cccc(-c3ccccc3)c2Br)cc1OCc1cccnc1)C(=O)O]

N-(4-(2-bromo-3-phenylbenzyloxy)-5-chloro-2-(pyridin-3-yl-methyleneoxy)benzyl) tyrosine

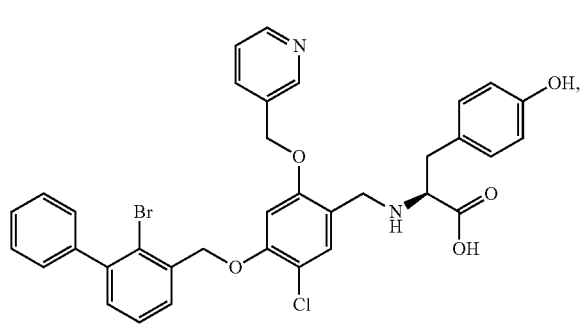 [SMILES: O=C(O)[C@H](Cc1ccc(O)cc1)NCc1cc(Cl)c(OCc2cccc(-c3ccccc3)c2Br)cc1OCc1cccnc1]

66

N-(4-(2-bromo-3-phenylbenzyloxy)-5-chloro-2-(pyridin-3-yl-methyleneoxy)benzyl) isoleucine

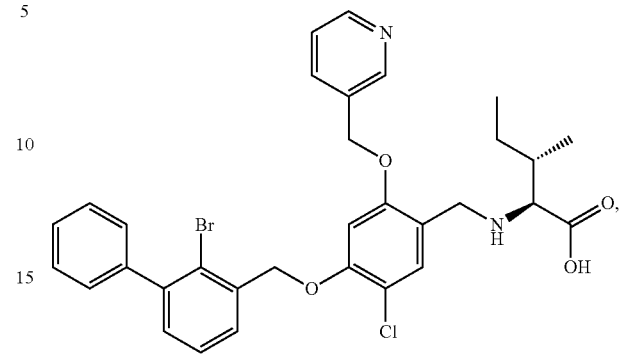

N-(4-(2-bromo-3-phenylbenzyloxy)-5-chloro-2-(pyridin-3-yl-methyleneoxy) benzyl) asparagine

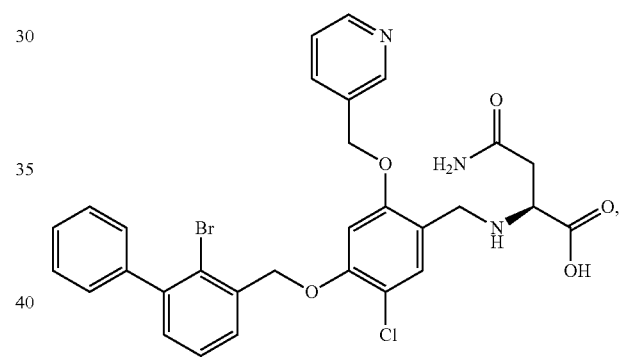

N-(hydroxyethyl)-4-(2-bromo-3-phenylbenzyloxy)-5-chloro-2-(pyridin-3-yl-methyleneoxy) benzylamine

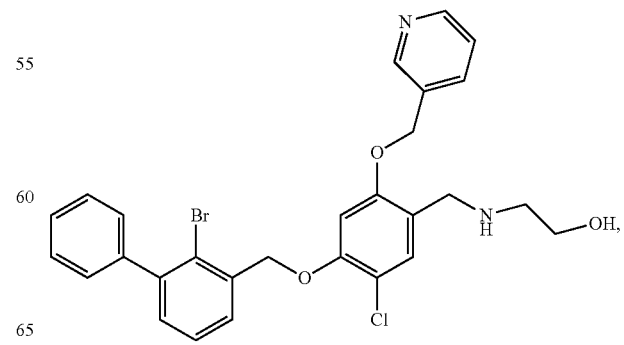

N-(4-(2-bromo-3-phenylbenzyloxy)-5-chloro-2-(pyridin-3-yl-methyleneoxy)benzyl) alanine

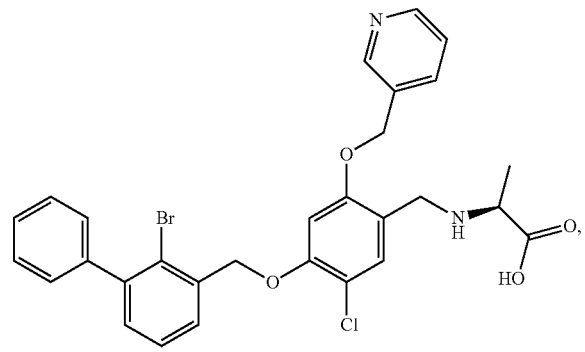 [SMILES: C[C@H](NCc1cc(Cl)c(OCc2cccc(-c3ccccc3)c2Br)cc1OCc1cccnc1)C(=O)O]

N-(4-(2-bromo-3-phenylbenzyloxy)-5-chloro-2-(pyridin-3-yl-methyleneoxy)benzyl) proline

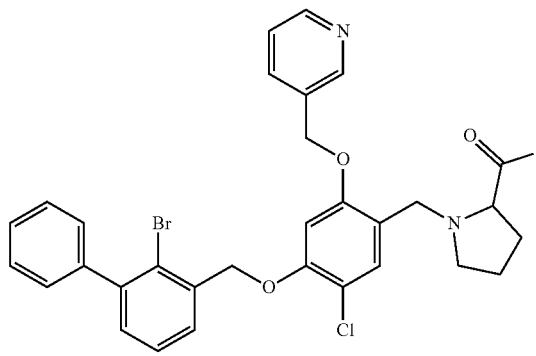

(S)-Sodium N-(4-(2-bromo-3-phenylbenzyloxy)-5-chloro-2-(pyridin-3-yl-methyleneoxy)benzyl) serinate

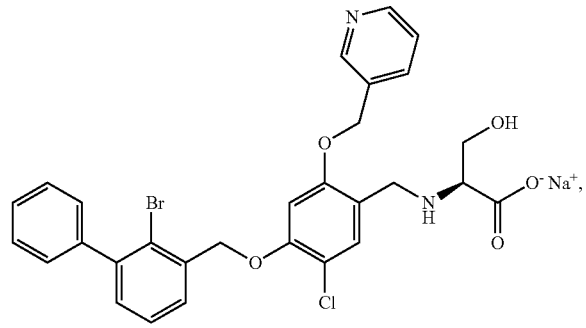

(S)-Calcium N-(4-(2-bromo-3-phenylbenzyloxy)-5-chloro-2-(pyridin-3-yl-methyleneoxy)benzyl) serinate

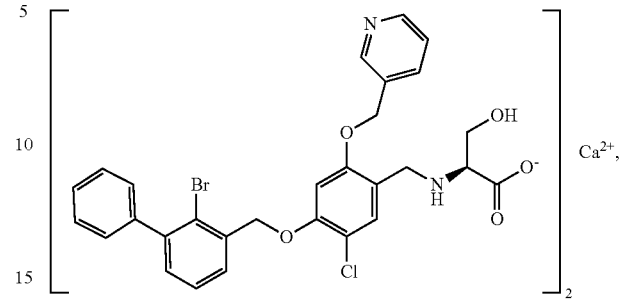

and (S)-(5-methyl-2-oxo-1,3-dioxol-4-yl)methyl N-(4-(2-bromo-3-phenylbenzyloxy)-5-chloro-2-(pyridin-3-yl-methyleneoxy) benzyl) serinate

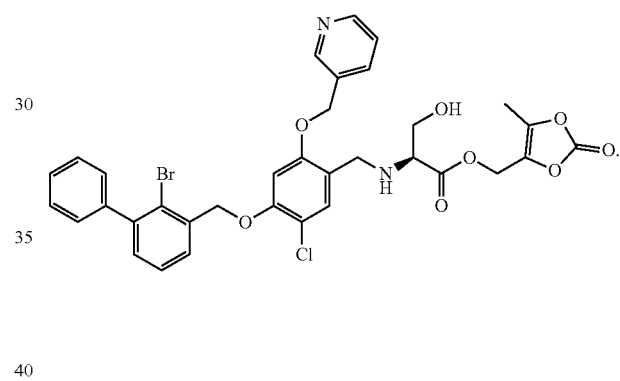

10. A nicotinyl alcohol ether derivative of claim 1, or a stereoisomer or a pharmaceutically acceptable salt thereof, wherein the pharmaceutically acceptable salt comprises a salt formed with an inorganic acid, a salt formed with an organic acid, alkali metal ion salt, alkaline earth metal ion salt or a salt formed with organic base which provides a physiologically acceptable cation, and an ammonium salt.

11. A nicotinyl alcohol ether derivative of claim 10, or a stereoisomer or a pharmaceutically acceptable salt thereof, wherein the inorganic acid is selected from hydrochloric acid, hydrobromic acid, phosphoric acid, and sulfuric acid; the organic acid is selected from methanesulfonic acid, p-toluenesulfonic acid, trifluoroacetic, citric acid, maleic acid, tartaric acid, fumaric acid, citric acid, and lactic acid; the alkali metal ion is selected from lithium ion, sodium ion, and potassium ion; the alkaline earth metal ion is selected from calcium ion and magnesium ion; and the organic base which provides a physiologically acceptable cation is selected form methylamine, dimethylamine, trimethylamine, piperidine, morpholine, and tris(2-hydroxyethyl) amine.

12. A pharmaceutical composition, characterized in that it comprises a nicotinyl alcohol ether derivative of claim 1, or a stereoisomer or a pharmaceutically acceptable salt thereof, as an active ingredient, and one or more pharmaceutically acceptable carriers or excipients.

13. A pharmaceutical composition, characterized in that it comprises a nicotinyl alcohol ether derivative of claim 9, or a stereoisomer or a pharmaceutically acceptable salt thereof, as an active ingredient, and one or more pharmaceutically acceptable carriers or excipients.

14. A process for the preparation of a nicotinyl alcohol ether derivative of claim 1, or a stereoisomer, or a pharmaceutically acceptable salt thereof, comprising the following steps:

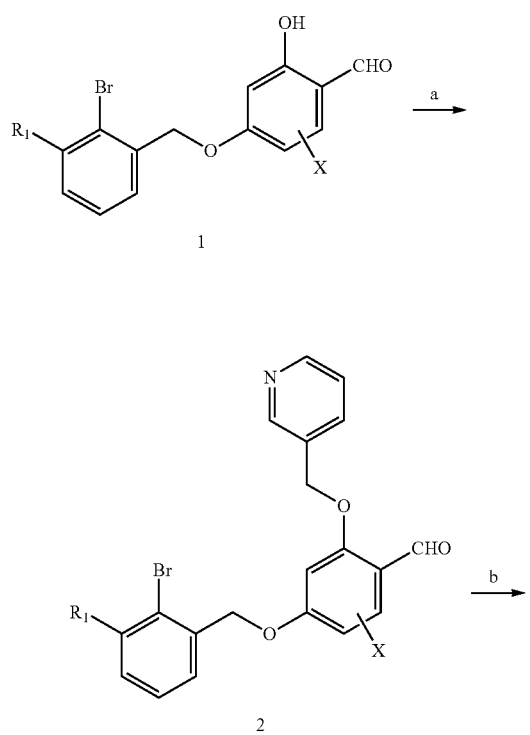

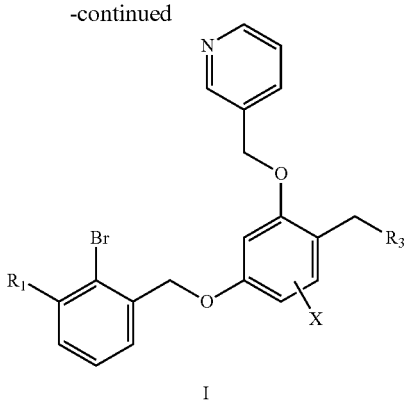

(a) 2-hydroxy-4-(2-bromo-3-R1 benzyloxy)-X-substituted benzaldehyde 1 as a starting material is reacted with pyridin-3-yl-methylene halide under basic conditions to obtain an aldehyde-containing intermediate compound 2; and (b) the aldehyde-containing intermediate compound 2 as the starting material is condensed with an amino group- or an imino group-containing $HR_3$ and the resultant product is reduced to obtain a target compound I;

wherein $R_1$, $R_3$ and X each is defined as claim 1.

15. A method for treating a disease associated with the PD-1/PD-L1 signaling pathway in a subject in need of such treatment comprising administering to the subject an effective amount of a nicotinyl alcohol ether derivative of claim 1, or a stereoisomer thereof, or a pharmaceutically acceptable salt thereof; wherein the disease is selected from the group consisting of melanoma, lung cancer, breast cancer, and colon cancer.

16. A method for treating a disease associated with the PD-1/PD-L1 signaling pathway in a subject in need of such treatment comprising administering to the subject an effective amount of the nicotinyl alcohol ether derivative of claim 9, or a stereoisomer thereof, or a pharmaceutically acceptable salt thereof; wherein the disease is selected from the group consisting of melanoma, lung cancer, breast cancer, and colon cancer.

* * * * *